US011834519B2

(12) United States Patent
Tagaya et al.

(10) Patent No.: US 11,834,519 B2
(45) Date of Patent: *Dec. 5, 2023

(54) COMPOSITIONS AND METHODS FOR MODULATING γ-C-CYTOKINE ACTIVITY

(71) Applicant: BIONIZ THERAPEUTICS, INC., La Jolla, CA (US)

(72) Inventors: Yutaka Tagaya, Rockville, MD (US); Nazli Azimi, San Juan Capistrano, CA (US)

(73) Assignee: BIONIZ THERAPEUTICS, INC., La Jolla, CA (US)

(*) Notice: Subject to any disclaimer, the term of this patent is extended or adjusted under 35 U.S.C. 154(b) by 762 days.

This patent is subject to a terminal disclaimer.

(21) Appl. No.: 16/294,733

(22) Filed: Mar. 6, 2019

(65) Prior Publication Data

US 2019/0194255 A1 Jun. 27, 2019

Related U.S. Application Data

(63) Continuation of application No. 15/474,312, filed on Mar. 30, 2017, now Pat. No. 10,227,382, which is a continuation of application No. 14/852,240, filed on Sep. 11, 2015, now Pat. No. 9,675,672, which is a continuation of application No. 13/980,305, filed on Jul. 17, 2013, now Pat. No. 9,133,244, and a continuation of application No. 13/868,725, filed on Apr. 23, 2013, now Pat. No. 9,133,243, which is a continuation of application No. 13/589,017, filed as application No. PCT/US2012/021566 on Jan. 17, 2012, now Pat. No. 8,455,449, said application No. 13/589,017 is a continuation of application No. PCT/US2012/021566, filed on Jan. 17, 2012.

(60) Provisional application No. 61/527,049, filed on Aug. 24, 2011, provisional application No. 61/433,890, filed on Jan. 18, 2011.

(51) Int. Cl.

| | |
|---|---|
| *C12N 15/63* | (2006.01) |
| *C07K 7/08* | (2006.01) |
| *A61Q 19/00* | (2006.01) |
| *C07K 14/52* | (2006.01) |
| *C12N 15/00* | (2006.01) |
| *C07K 7/06* | (2006.01) |
| *A61K 8/64* | (2006.01) |
| *A61K 38/20* | (2006.01) |
| *A61Q 3/00* | (2006.01) |
| *A61Q 7/00* | (2006.01) |
| *A61Q 19/08* | (2006.01) |
| *A61K 47/64* | (2017.01) |
| *C07K 14/54* | (2006.01) |
| *A61K 38/10* | (2006.01) |
| *A61K 38/00* | (2006.01) |

(52) U.S. Cl.
CPC .............. *C07K 7/08* (2013.01); *A61K 8/64* (2013.01); *A61K 38/20* (2013.01); *A61K 47/642* (2017.08); *A61K 47/643* (2017.08); *A61Q 3/00* (2013.01); *A61Q 7/00* (2013.01); *A61Q 19/00* (2013.01); *A61Q 19/004* (2013.01); *A61Q 19/08* (2013.01); *C07K 7/06* (2013.01); *C07K 14/52* (2013.01); *C07K 14/54* (2013.01); *C12N 15/00* (2013.01); *A61K 38/00* (2013.01); *A61K 38/10* (2013.01)

(58) Field of Classification Search
CPC . C07K 7/08; C07K 7/06; C07K 14/52; C07K 14/54; A61K 47/643; A61K 47/642; A61K 8/64; A61K 38/20; A61K 38/00; A61K 38/10; A61Q 3/00; A61Q 7/00; A61Q 19/00; A61Q 19/004; A61Q 19/08
See application file for complete search history.

(56) References Cited

U.S. PATENT DOCUMENTS

| | | | |
|---|---|---|---|
| 4,518,584 A | 5/1985 | Mark et al. | |
| 5,700,913 A | 12/1997 | Taniguchi et al. | |
| 5,795,966 A | 8/1998 | Grabstein et al. | |
| 6,013,480 A | 1/2000 | Grabstein et al. | |
| 6,028,186 A | 2/2000 | Tasset et al. | |

(Continued)

FOREIGN PATENT DOCUMENTS

| | | |
|---|---|---|
| CN | 1478098 A | 2/2004 |
| CN | 1703423 A | 11/2005 |

(Continued)

OTHER PUBLICATIONS

Seffernick et al. (J. Bacteriol., 2001, 183: 2405-2410). (Year: 2001).*

(Continued)

*Primary Examiner* — Catherine S Hibbert

(74) *Attorney, Agent, or Firm* — Knobbe, Martens, Olson & Bear LLP

(57) ABSTRACT

The γc-family cytokines, Interleukin-2 (IL-2), Interleukin-4 (IL-4), Interleukin-7 (IL-7), Interleukin-9 (IL-9), Interleukin-15 (IL-15), and Interleukin-21 (IL-21), are associated with important human diseases, such as leukemia, autoimmune diseases, collagen diseases, diabetes mellitus, skin diseases, degenerative neuronal diseases and graft-versus-host disease (GvHD). Thus, inhibitors of γc-cytokine activity are valuable therapeutic and cosmetic agents as well as research tools. Peptide and/or peptide derivative antagonists based on the consensus γc-subunit binding site to inhibit γc-cytokine activity are described. Also described are peptide and/or peptide derivative antagonists exhibiting Simul-Block activity, and inhibiting the activity of multiple γc-cytokine family members.

18 Claims, 10 Drawing Sheets

Specification includes a Sequence Listing.

(56) References Cited

U.S. PATENT DOCUMENTS

| | | | |
|---|---|---|---|
| 6,127,387 A | 10/2000 | Huang et al. | |
| 6,168,783 B1 | 1/2001 | Grabstein et al. | |
| 6,261,559 B1 | 7/2001 | Levitt et al. | |
| 6,307,024 B1 | 10/2001 | Novak et al. | |
| 6,323,027 B1 | 11/2001 | Burkly et al. | |
| 6,686,178 B2 | 2/2004 | Novak et al. | |
| 6,770,745 B2 | 8/2004 | Burkly et al. | |
| 6,793,919 B2 | 9/2004 | Mohler | |
| 6,797,263 B2 | 9/2004 | Strom et al. | |
| 6,811,780 B2 | 11/2004 | Furfine et al. | |
| 6,838,433 B2 | 1/2005 | Serlupo-Crescenzi | |
| 6,955,807 B1 | 10/2005 | Shanafelt et al. | |
| 7,105,653 B2 | 9/2006 | Shanafelt et al. | |
| 7,148,333 B2 | 12/2006 | Cox, III | |
| 7,192,578 B2 | 3/2007 | Levitt et al. | |
| 7,235,240 B2 | 6/2007 | Grabstein et al. | |
| 7,314,623 B2 | 1/2008 | Grusby et al. | |
| 7,347,995 B2 | 3/2008 | Strom et al. | |
| 7,423,123 B2 | 9/2008 | Boisvert et al. | |
| 7,473,765 B2 | 1/2009 | Novak et al. | |
| 7,632,814 B2 | 12/2009 | Hazlehurst et al. | |
| 7,645,449 B2 | 1/2010 | Stassi et al. | |
| 7,700,088 B2 | 4/2010 | Levitt et al. | |
| 7,731,946 B2 | 6/2010 | Grusby et al. | |
| 7,785,580 B2 | 8/2010 | Pan et al. | |
| 7,786,072 B2 | 8/2010 | Verdine et al. | |
| 7,910,123 B2 | 3/2011 | McKay | |
| 7,959,908 B2 | 6/2011 | Nelson et al. | |
| 8,110,180 B2 | 2/2012 | Novak et al. | |
| 8,211,420 B2 | 7/2012 | Bondensgaard | |
| 8,455,449 B2 | 6/2013 | Tagaya | |
| 8,512,946 B2 | 8/2013 | Mirkin et al. | |
| 9,133,243 B2 | 9/2015 | Tagaya | |
| 9,133,244 B2 | 9/2015 | Tagaya | |
| 9,675,672 B2 | 6/2017 | Tagaya | |
| 9,951,105 B2 | 4/2018 | Tagaya | |
| 9,959,384 B2 | 5/2018 | Azimi et al. | |
| 10,030,058 B2 | 7/2018 | Azimi | |
| 10,030,059 B2 | 7/2018 | Azimi | |
| 10,227,382 B2 | 3/2019 | Tagaya | |
| 10,358,477 B2 | 7/2019 | Jacques et al. | |
| 10,808,009 B2 | 10/2020 | Tagya et al. | |
| 10,854,312 B2 | 12/2020 | Azimi et al. | |
| 11,400,134 B2 | 8/2022 | Azimi | |
| 11,462,297 B2 | 10/2022 | Azimi et al. | |
| 2002/0114781 A1 | 8/2002 | Strom et al. | |
| 2003/0049798 A1 | 3/2003 | Carter et al. | |
| 2003/0108549 A1 | 6/2003 | Carter et al. | |
| 2004/0009150 A1* | 1/2004 | Nelson | A61P 37/02 424/85.2 |
| 2004/0126900 A1 | 7/2004 | Barry | |
| 2004/0136954 A1 | 7/2004 | Grusby et al. | |
| 2005/0124044 A1 | 6/2005 | Cunningham et al. | |
| 2006/0008848 A1 | 1/2006 | Verdine et al. | |
| 2006/0034892 A1 | 2/2006 | Ueno | |
| 2006/0039902 A1 | 2/2006 | Young et al. | |
| 2006/0236411 A1 | 10/2006 | Dreher et al. | |
| 2006/0263857 A1 | 11/2006 | Lefrancois et al. | |
| 2007/0048266 A1* | 3/2007 | Nelson | A61P 1/04 424/85.2 |
| 2007/0048831 A1 | 3/2007 | Sprecher et al. | |
| 2007/0122413 A1 | 5/2007 | Sivakumar et al. | |
| 2008/0038275 A1 | 2/2008 | Martin | |
| 2008/0108552 A1 | 5/2008 | Hazlehurst et al. | |
| 2008/0166338 A1 | 7/2008 | Leonard | |
| 2009/0136511 A1 | 5/2009 | Santos Savio et al. | |
| 2009/0148403 A1 | 6/2009 | Bosivert et al. | |
| 2009/0253864 A1 | 10/2009 | Peschke et al. | |
| 2009/0258357 A1 | 10/2009 | Ruben | |
| 2010/0099742 A1 | 4/2010 | Stassi | |
| 2010/0135958 A1 | 6/2010 | Hwu | |
| 2010/0196309 A1 | 8/2010 | Bondensgaard et al. | |
| 2010/0266531 A1 | 10/2010 | Hsieh | |
| 2011/0081327 A1 | 4/2011 | Nicolette | |
| 2011/0091515 A1 | 4/2011 | Zilberman | |
| 2011/0142833 A1 | 6/2011 | Young | |
| 2011/0245090 A1 | 10/2011 | Abbas | |
| 2011/0311475 A1 | 12/2011 | Borte | |
| 2012/0329728 A1 | 12/2012 | Tagaya | |
| 2013/0052127 A1 | 2/2013 | Sasaki et al. | |
| 2013/0095102 A1 | 4/2013 | Levin | |
| 2013/0217858 A1 | 8/2013 | Bioniz | |
| 2016/0000877 A1 | 1/2016 | Bionz | |
| 2016/0306918 A1 | 10/2016 | Azimi | |
| 2017/0051015 A1 | 2/2017 | Bionz | |
| 2017/0101452 A1 | 4/2017 | Azimi | |
| 2017/0204153 A1 | 7/2017 | Tagaya | |
| 2017/0240607 A1 | 8/2017 | Bioniz | |
| 2018/0125941 A1 | 5/2018 | Greve | |
| 2018/0237475 A1 | 8/2018 | Tagaya | |
| 2018/0258174 A1 | 9/2018 | Mortier et al. | |
| 2018/0349550 A1 | 12/2018 | Azimi et al. | |
| 2019/0070263 A1 | 3/2019 | Azimi | |
| 2020/0347128 A1 | 11/2020 | Tagaya et al. | |
| 2020/0399316 A1 | 12/2020 | Tagaya et al. | |
| 2021/0082537 A1 | 3/2021 | Azimi et al. | |
| 2021/0324029 A1 | 10/2021 | Doerr et al. | |
| 2023/0060637 A1 | 3/2023 | Azimi | |
| 2023/0197187 A1 | 6/2023 | Azimi et al. | |

FOREIGN PATENT DOCUMENTS

| | | |
|---|---|---|
| CN | 103501805 A | 1/2014 |
| CN | 103501805 B | 9/2018 |
| EP | 1525213 B1 | 4/2005 |
| EP | 2665486 A1 | 11/2013 |
| JP | 2004-525076 | 8/2004 |
| JP | 2005-508179 | 3/2005 |
| WO | WO 8702990 A1 | 5/1987 |
| WO | WO 2000/72864 A1 | 12/2000 |
| WO | WO 2003040313 A1 | 9/2003 |
| WO | WO 03/087320 A2 | 10/2003 |
| WO | WO 2003/103589 A2 | 12/2003 |
| WO | WO 2004084835 A2 | 10/2004 |
| WO | WO 2005014642 A2 | 2/2005 |
| WO | WO 2005030196 A2 | 4/2005 |
| WO | WO 2005067956 A2 | 7/2005 |
| WO | WO 2005/105830 A1 | 11/2005 |
| WO | WO 2005112983 A2 | 12/2005 |
| WO | WO 2006105538 A2 | 5/2006 |
| WO | WO 2006111524 A2 | 10/2006 |
| WO | WO 2006113331 A1 | 10/2006 |
| WO | WO 2008049920 A2 | 2/2008 |
| WO | WO 2009108341 A1 | 3/2009 |
| WO | WO 2009100035 A2 | 8/2009 |
| WO | WO 2009132821 A1 | 11/2009 |
| WO | WO 2010/011313 A2 | 1/2010 |
| WO | WO 2010039533 A2 | 4/2010 |
| WO | WO 2010/054667 A1 | 5/2010 |
| WO | WO 2010076339 A1 | 7/2010 |
| WO | WO 2010103038 A1 | 9/2010 |
| WO | WO 2010133828 A1 | 11/2010 |
| WO | WO 2011/008260 A1 | 1/2011 |
| WO | WO 2011070214 A2 | 6/2011 |
| WO | WO 2011133948 A1 | 10/2011 |
| WO | WO 2012006585 A2 | 1/2012 |
| WO | WO 2012012531 A2 | 1/2012 |
| WO | WO 2012/099886 | 7/2012 |
| WO | WO 2012/175222 A1 | 12/2012 |
| WO | WO 2015/089217 A2 | 6/2015 |
| WO | WO 2015/089217 A3 | 6/2015 |
| WO | WO 2017/062685 A1 | 4/2017 |
| WO | WO 2018/187499 A1 | 10/2018 |

OTHER PUBLICATIONS

Witkowski et al. (Biochemistry, 1999, 38: 11643-11650). (Year: 1999).*

Antony, et al., "Interleukin-2-Dependent Mechanisms of Tolerance and Immunity In Vivo," J. Immunol. 176: 5255-5266, 2006.

Azimi, N., "Human T Cell Lymphotropic Virus Type I Tax Protein Trans-Activates Interleukin 15 Gene Transcription Through an NF-kappaB Site," Proc. Natl. Acad. Sci. USA 95:2452-2457, 1998.

(56) References Cited

OTHER PUBLICATIONS

Azimi, N., "Involvement of IL-15 In The Pathogenesis of Human T Lymphotropic Virus Type-I-Associated Myelopathy/Tropical Spastic Paraparesis: Implications for Therapy with a Monoclonal Antibody Directed to the IL-2/15Rbeta Receptor," J. Immunol. 163:4064-4072, 1999.

Azimi, N., et al., "How Does Interleukin 15 Contribute to the Pathogenesis of HTLV Type-1 Associated Myelopathy/Tropical Spastic Paraparesis?" AIDS Res. Hum. Retroviruses 16:1717-1722, 2000.

Azimi, N., et al., "IL-15 Plays a Major Role in the Persistence of Tax-specific CD8 Cells in HAM/TSP patients," Proc. Natl. Acad. Sci. 98:14559-14564, 2001.

Bazan, J.F., "Hematopoietic Receptors and Helical cytokines," Immunol. Today 11:350-354, 1990.

Bernard, et al Identification of an Interleukin-15α Receptor-binding Site on Human Interleukin-15*, The Journal of Biological Chemistry (2004)279:24313-24322.

Bettini, M., and D.A. Vignali, "Regulatory T Cells and Inhibitory Cytokines in Autoimmunity," Curr. Opin. Immunol. 21:612-618, 2009.

Bodd, M., et al., "HLA-DQ2-Restricted Gluten-Reactive T cells Produce IL-21 but not IL-17 or IL-22," Mucosal Immunol. 3:594-601, 2010.

Bonsch, et al, Species-specific Agonist/Antagonist Activities of Human Interleukin-4 Variants Suggest Distinct Ligand Binding Properties of Human and Murine Common Receptor γ Chain*, The Journal of Biological Chemistry (1995) 270:8452-8457.

De Rezende, L.C., et al., "Regulatory T Cells as a Target for Cancer Therapy," Arch. Immunol. Ther. Exp. 58:179-190, 2010.

Decision of Rexamination in Chinese Application 201280010348.8.

Definition of composite from www.merriam-sebster.com/dictionary/composite, pp. 1-5. Accessed Feb. 17, 2015.

Definition of derivative from http://cancerweb.ncl.ac.uk/omd/about.html, pp. 1-5. Accessed Jul. 7, 2005.

Dubois, S., et al., "IL-15R alpha Recycles and Presents IL-15 In Trans to Neighboring Cells," Immunity 17:537-547, 2002.

Extended EP Search report dated May 22, 2014 for PCT/US2012/021566.

Fehniger, T.A., "Fatal Leukemia in Interleukin 15 Transgenic Mice Follows Early Expansions in Natural Killer and Memory Phenotype $CD8_+$ T Cells," J. Exp. Med. 193:219-231, 2001.

Final Office Action dated Feb. 24, 2015 for U.S. Appl. No. 13/868,725.

Final Office Action dispatched Nov. 29, 2016 for JP Patent Application 2013-550541.

Fisher, A.G. et al., "Lymphoproliferative disorders in an IL-7 transgenic mouse line," Leukemia 2, pp. 66-68, 1993.

Gong, J.H. et al., Characterization of a human cell line (NK-92) with phenotypical and functional characteristics of activated natural killer cells. Leukemia 8, pp. 652-658, 1994.

Hennighausen, L., and G.W. Robinson, "Interpretation of Cytokine Signaling Through the Transcription Factors STAT5A and STAT5B," Genes Dev. 22:711-721, 2008.

Hodge, D.L., et al., "IL-2 and IL-12 Alter NK Cell Responsiveness to IFN-Gamma-Inducible Protein 10 by Down-Regulating CXCR3 Expression, J. Immun. 168:6090-6098, 2002.

International Preliminary Report on Patentability dated Jul. 23, 2013 for PCT/US2012/021566.

International Preliminary Report on Patentability dated Jun. 14, 2016 for PCT/US2012/062870.

International Search Report and Written Opinion dated Jan. 17, 2017 for PCT/US2016/055845.

International Search Report and Written Opinion of the International Searching Authority in International Application No. PCT/US2012/021566 dated May 10, 2012.

International Search Report dated Jun. 26, 2015 for PCT/US14/69597.

Klingemann, H.G. et al., "A cytotoxic NK-cell line (NK-92) for ex vivo purging of leukemia from blood," Blood Marrow Transplant 2, 1996, pp. 68-75.

Krause, C.D. and S. Pestka, "Evolution of the Class 2 Cytokines and Receptors, and Discovery of New Friends and Relatives," Pharmacol. and Therapeutics 106:299-346, 2005.

Kundig, T.M. et al. "Immune Responses of the interleukin-2-deficient mice," Science 262, pp. 1059-1061, 1993.

Le Buanec, H., et al., "Control of Allergic Reactions in Mice by an Active Anti-Murine IL-4 Immunization," Vaccine 25:7206-7216, 2007.

Littman, D.R., and A.Y. Rudensky, "Th17 and Regulatory T Cells in Mediating and Restraining Inflammation," Cell 140(6):845-858, 2010.

Miyagawa, F., et al., "IL-15 Serves as a Costimulator in Determining the Activity of Autoreactive CD8 T Cells in an Experimental Mouse Model of Graft-Versus-Host-Like Disease," J. Immunol. 181:1109-1119, 2008.

NCBI Accession No. ABF82250, Accessed Aug. 11, 2014.
NCBI Accession No. BAA96385, Accessed Aug. 11, 2014.
NCBI Accession No. NP_999580, Accessed Aug. 11, 2014.
NCBI Accession No. ACT78884, Accessed Aug. 11, 2014.
NCBI Accession No. NP_999288, Accessed Aug. 11, 2014.

Noguchi, M., et al., "Interleukin 2 Receptor Gamma Chain Mutation Results in X-linked Severe Combined Immunodeficiency in Humans," Cell 73:147-157, 1993.

Notice of Acceptance dated Oct. 19, 2016 for AU Application 2012207456.

Notice of Allowance dated Feb. 19, 2013 for U.S. Appl. No. 13/589,017.

Notice of Allowance dated Feb. 6, 2017 for U.S. Appl. No. 14/852,240.

Notice of Allowance dated May 11, 2015 for U.S. Appl. No. 13/868,725.

Notice of Allowance dated May 4, 2015 for U.S. Appl. No. 13/980,305.

Notice of Allowance dated Dec. 15, 2017 in U.S. Appl. No. 15/179,900.

Notice of Allowance dated Dec. 19, 2017 for U.S. Appl. No. 15/103,804.

Notification of Re-examination dated Mar. 24, 2017 for CN Patent Application 201280010348.8.

O'Shea, J.J., "Targeting the Jak/STAT Pathway for Immunosuppression," Ann. Rheum. Dis. 63:(Suppl. II):ii67-71, 2004.

Office Action dated Aug. 18, 2014 for U.S. Appl. No. 13/868,725.
Office Action dated Aug. 3, 2017for U.S. Appl. No. 15/103,804.
Office Action dated Aug. 8, 2017for U.S. Appl. No. 15/585,666.
Office Action dated Jan. 26, 2016 for JP Patent Application 2013-550541.
Office Action dated Jul. 2, 2014 for corresponding CN Application 201280010348.8.
Office Action dated Jul. 24, 2017 in U.S. Appl. No. 15/179,900.
Office Action dated Jul. 4, 2016 for Chinese Patent Application No. 201280010348.8.
Office Action dated Nov. 12, 2014 for U.S. Appl. No. 13/980,305.
Office Action dated Oct. 26, 2016 in EP Patent Application No. 12736203.6.
Office Action dated Oct. 18, 2014 for U.S. Appl. No. 13/868,725.
Office Action dated Oct. 22, 2015 for AU Application 2012207456.
Office Action dated Oct. 27, 2015 for Chinese Patent Application No. 201280010348.8.
Office Action dated Sep. 6, 2016 for U.S. Appl. No. 14/852,240.
Office Action dated Apr. 28, 2015 for Chinese Patent Application No. 201280010348.8.
Office Action dated Oct. 23, 2017 in U.S. Appl. No. 15/287,517.

Oh, U., and S. Jacobson, "Treatment of HTLV-I-Associated Myelopathy / Tropical Spastic Paraparesis: Towards Rational Targeted Therapy," Neurol. Clin. 26:781-785, 2008.

Orzaez, M., et al., "Peptides and Peptide Mimics as Modulators of Apoptotic Pathways," Chem. Med. Chem. 4:146-160, 2009.

Paul, W.E., "Pleiotropy and Redundancy: T Cell-Derived Lymphokines in the Immune Response," Cell 57:521-524, 1989.

Pesu, M., "Jak3, Severe Combined Immunodeficiency, and a New Class of Immunosuppressive Drugs," Immunol. Rev. 203:127-142, 2005.

(56) References Cited

OTHER PUBLICATIONS

Pesu, M., Laurence, et al., "Therapeutic Targeting of Janus Kinases," Immunol. Rev. 223:132-142, 2008.
Restriction Requirement dated Feb. 28, 2017 for U.S. Appl. No. 15/179,900.
Restriction Requirement dated Jun. 24, 2014 for U.S. Appl. No. 13/980,305.
Restriction Requirement dated Mar. 24, 2017 for U.S. Appl. No. 15/103,804.
Restriction Requirement dated May 9, 2014 for U.S. Appl. No. 13/868,725.
Restriction Requirement dated Jul. 25, 2017 in U.S. Appl. No. 15/287,517.
Rochman, Y., et al., "New Insights into the Regulation of T Cells by Gamma C Family Cytokines," Nat. Rev. Immunol. 9:480-490, 2009.
Sakaguchi, S., et al., "Regulatory T Cells and Immune Tolerance," Cell 133:775-787, 2008.
Sato, N., et al., "Development of an IL-15-Autocrine CD8 T-cell Leukemia in IL-15 Transgenic mice requires the cis-expression of IL-15R apha," Blood , 2011.
Sugamura, K., et al., "The Common Gamma-Chain for Multiple Cytokine Receptors," Adv. Immunol. 59:225-277, 1995.
Sugamura, K., et al., "The Interleukin-2 Receptor Gamma Chain: Its Role in the Multiple Cytokine Receptor Complexes and T Cell Development in XSCID," Annu. Rev. Immunol. 14:179-205, 1996.
Supplementary European Search Report dated May 22, 2014 for European Application No. 12784848.9.
Tagaya, Y., "Memory CD8 T Cells Now Join 'Club 21," J. Leuk. Biol. 87:13-15, 2010.
Tagaya, Y., et al., "Identification of a Novel Receptor/Signal Transduction Pathway for IL-15/T in Mast Cells," Embo J. 15:4928-4939, 1996.
Takai, K et al., The Wheat-Germ Cell-Free Expression System, Curr. Pharm. Biotechnol. 11, pp. 272-278, 2010.
Takeshita, T., et al., "Cloning of the Gamma Chain of the Human IL-2 Receptor," Science 257:379-382, 1992.
Tanaka, T., et al., "A Novel Monoclonal Antibody Against Murine IL-2 Receptor Beta-Chain. Characterization of Receptor Expression in Normal Lymphoid Cells and EL-4 Cells," J. Immunol. 147:2222-2228, 1991.
Waldmann, T.A., Anti-Tac (daclizumab, Zenapax) in the Treatment of Leukemia, Autoimmune Diseases, and in the Prevention of Allograft Rejection: A 25-Year Personal Odyssey, J. Clin. Immunol. 27:1-18, 2007.
Water is naturally occurring from www.biology-online.org/dictionary/Water, pp. 1-3, Accesssed Apr. 24, 2014.
Final Office Action dated Dec. 13, 2017 for U.S. Appl. No. 15/585,666.
Hines, L et at. Interleukin 15, partial [synthetic construct]. NCBI PDS Accession No. AAX36174, interleukin 15, partial [synthetic construct]. Submitted Jan. 5, 2005; downloaded from the internet <https://www.ncbi.nlm.nih.gov/protein/60811495/> on Dec. 14, 2016, p. 1.
International Preliminary Report on Patentability dated Apr. 10, 2018 for PCT/US2016/055845.
International Search Report and Written Opinion dated Aug. 23, 2018 for PCT/US2018/026125.
Notification of Allowance dated May 31, 2018 for CN Patent Application 201280010348.8.
Notice of Allowance dated Mar. 26, 2018 in U.S. Appl. No. 15/287,517.
Notice of Allowance dated Mar. 26, 2018 in U.S. Appl. No. 15/585,666.
Office Action dated Oct. 4, 2017 in European Patent Application No. 12736203.6.
Office Action dated Nov. 22, 2017 in Canadian Application No. 2,824,51.
Office Action dated Feb. 9, 2018 in Australian Application No. 2017200489.
Office Action dated Feb. 20, 2018 for JP Patent Application 2013-550541.
Office Action dated May 8, 2018 in JP Patent Application No. 2017-90501.
Abadie et al., "IL-15: A central regulator of celiac disease immunopathology". Immunol Rev. (2014) 260(1): 221-234.
Aringer et al., "Serum interleukin-15 is elevated in systemic lupus erythematosus", Rheumatology (2001) 40(8):876-881.
Asano et al., "Molecular scanning of interleukin-21 gene and genetic susceptibility to type 1 diabetes." Hum Immunol. (2007) 68(5):384-391.
Atwa et al., "T-helper 17 cytokines (interleukins 17, 21, 22, and 6, and tumor necrosis factor-$\alpha$) in patients with alopecia areata: association with clinical type and severity". Int J Dermatol. (2016) 55(6):666-672.
Awwad et al., "Overview of Antibody Drug Delivery". Pharmaceutics (2018) 10(3): 83.
Baranda et al., "IL-15 and IL-15R in leucocytes from patients with systemic lupus erythematosus." Rheumatology (2005) 44(12): 1507-1513.
Ben Ahmed et al., "IL-15 renders conventional lymphocytes resistant to suppressive functions of regulatory T cells through activation of the phosphatidylinositol 3-kinase pathway". J Immunol. (2009) 182(11):6763-6770.
Benahmed et al., "Inhibition of TGF-beta signaling by IL-15: a new role for IL-15 in the loss of immune homeostasis in celiac disease". Gastroenter. (2007) 132(3):994-1008.
Blaser et al., "Donor-derived IL-15 is critical for acute allogeneic graft-versus-host disease". Blood (2005) 105(2): 894-901.
Blažek et al., "The production and application of single-chain antibody fragments". Folia Microbiol. (2003) 48(5): 687-698.
Bobbala et al., "Interleukin-15 plays an essential role in the pathogenesis of autoimmune diabetes in the NOD mouse", Diabetologia (2012) 55: 3010-3020.
Borrego et al., "Recognition of human histocompatibility leukocyte antigen (HLA)-E complexed with HLA class I signal sequence-derived peptides by CD94/NKG2 confers protection from natural killer cell-mediated lysis". J Exp Med. (1998) 187(5): 813-818.
Botti et al., "Psoriasis, from pathogenesis to therapeutic strategies: IL-21 as a novel potential thereapeutic target". Curr Pharm Biotechnol. (2012) 13(10): 1861-1867.
Broux et al., "IL-15 amplifies the pathogenic properties of CD4+ CD28- T cells in multiple sclerosis". J Immunol. (2015) 194(5): 2099-2109.
Brumbaugh et al., "Clonotypic differences in signaling from CD94 (kp43) on NK cells lead to divergent cellular responses". J Immunol. (1996) 157(7): 2804-2812.
Bubier et al., "A critical role for IL-21 receptor signaling in the pathogenesis of systemic lupus erythematosus in BXSB-Yaa mice." Proc Natl Acad Sci U S A (2009) 106(5):1518-1523.
Bucher et al., "IL-21 blockade reduces graft-versus-host disease mortality by supporting inducible T regulatory cell generation". 2009 114:5375-84.
Cantoni et al., "The activating form of CD94 receptor complex: CD94 covalently associates with the Kp39 protein that represents the product of the NKG2-C gene". Eur J Immunol. (1998) 28: 327-338.
Caruso et al., "Involvement of interleukin-21 in the epidermal hyperplasia of psoriasis". Nature Med. (2009) 15(()): 1013-1015.
Caruso et al., "Pathogenic role of interleukin-21 in psoriasis." Cell Cycle (2009) 8: 3629-3630.
Chen et al., "Insulin-dependent diabetes induced by pancreatic betacell expression of IL-15 and IL-15R alpha", Proc Natl Acad Sci U S A (2013) 110:13534-13539.
Chen et al., "Induction of autoimmune diabetes in non-obese diabetic mice requires interleukin-21-dependent activation of autoreactive CD8$^+$ T cells". Clin Exp Immunol. (2013) 173(2): 184-194.
Chik et al., "Elevated serum interleukin-15 level in acute graft-versus-host disease after hematopoietic cell transplantation." J Pediatr Hematol Oncol. (2003) 25(12): 960-964.
Cox et al., "Immunoassay methods", in Assay Guidance Manual [Internet], G.S. Sittampalam, N.P. Coussens, H. Nelson, et al. [Eds.]

(56) References Cited

OTHER PUBLICATIONS (Bethesda, MD: Eli Lilly & Company and the National Center for Advancing Translational Sciences); 2004 Edition.
D'Auria et al., "Increased serum interleukin-15 levels in bullous skin diseases: correlation with disease intensity". Arch Dermatol Res. (1999) 291 : 354-356.
De Nitto et al., "Involvement of interleukin-15 and interleukin-21, two gamma-chain-related cytokines, in deiac disease", World J Gastroenter. (2009) 15:4609-4614.
De Nitto et al. "Interleukin-21 triggers effector cell responses in the gut." World J Gastroenterol. (2010) 16(29):3638-3641.
DePaolo et al., "Co-adjuvant effects of retinoic acid and IL-15 induce inflammatory immunity to dietary antigens". Nature (2011) 471(7337): 220-224.
Di Sabatino A. et al., "Epithelium derived interleukin 15 regulates intraepithelial lymphocyte Th1 cytokine production, cytotoxicity, and survival in coeliac disease", Gut (2006) 55(4):469-477.
Fang et al., "Prophylactic effects of interleukin-2 receptor antagonists against graft-versus-host disease following unrelated donor peripheral blood stem cell transplantation". Biol Blood Marrow Transplant. (2012) 18(5): 754-762.
Ferreira et al., "IL-21 production by CD4+ effector T cells and frequency of circulating follicular helper T cells are increased in type 1 diabetes patients", Diabetologia (2015) 58: 781-790.
Fina et al., "Interleukin 21 contributes to the mucosal T helper cell type 1 resonse in coeliac disease". Gut (2008) 57(7):887-892.
Frenzel et al., "Designing Human Antibodies by Phage Display". Transfus Med Hemother. (2017) 44(5): 312-318.
Fuentes-Duculan et al., "Biomarkers of alopecia areata disease activity and response to corticosteroid treatment". Exp Dermatol. (2016) 4:282-286.
Garrity et al., "The activating NKG2D receptor assembles in the membrane with two signaling dimers into a hexameric structure". Proc Natl Acad Sci. (2005) 102(21): 7641-7646.
Ghalamfarsa et al., "IL-21 and IL-21 receptor in theimmunopathogenesis of multiple sclerosiS", J Immunotoxicol. (2016) 13(3):274-285.
Gilhar et al., "Alopecia areata animal models illuminate autoimmune pathogenesis and novel immunotherapeutic strategies". Autoimmun Rev. (2016) 15(7): 726-735.
Gonzalez-Alvaro et al., "Increased serum levels of interleukin-15 in rheumatoid arthritis with long-term disease." Clin Exp Rheumatol. (2003) 21(5):639-642.
Grando et al., "Mediators of inflammation in blister fluids from patients with pemphigus vulgaris and bullous pemphigoid". 1989 Arch Dermatol. (1989) 125:925-930.
Groh et al., "Stimulation of T cell autoreactivity by anomalous expression of NKG2D and its MIC ligands in rheumatoid arthritis". Proc Natl Acad Sci U S A. (2003) 100(16):9452-9457.
Guo-Qiang et al., "Guided selection methods through chain shuffling". Methods Mol Biol. (2009) 562(10): 133-142.
Habib T. et al., "IL-21: a novel IL-2-family lymphokine that modulates B, T, and natural killer cell responses", J Allergy Clin Immunol. (2003) 112(6):1033-1045.
Hammers et al., "Antibody Phage Display: Technique and Applications". J Invest Dermatol. (2014) 134(2): e17; 13 pages.
Harada et al., "Production of interleukin-7 and interleukin-15 by fibroblast-like synoviocytes from patients with rheumatoid arthritis." Arthritis Rheum. (1999) 42(7):1508-1516.
He et al., "Elevated serum levels of interleukin 21 are associated with disease severity in patients with psoriasis." Br J Dermatol. (2012) 167: 191-193.
Hessian P.A. et al., "Cytokine profile of the rheumatoid nodule suggests that it is a Th1 granuloma." Arthritis Rheum. (2003) 48(2):334-338.
Hippen et al., "Blocking IL-21 signaling ameliorates xenogeneic GVHD induced by human lymphocytes". Blood (2012) 119(2): 619-628.

Hodge et al., "IL-2 and IL-12 alter NK cell responsiveness to IFN-gamma-inducible protein 10 by down-regulating CXCR3 expression". J Immunol. (2002) 168(12): 6090-6098.
Hong et al., Regulatory and pro-inflammatory phenotypes of myelin basic protein-autoreactive T cells in multiple sclerosis. Int Immunol. (2009) 21(12): 1329-1340.
Hüe et al., "A direct role for NKG2D/MICA interaction in villous atrophy during celiac disease." Immunity (2004) 21(3): 367-377.
Jabri B. et al., "Selective expansion of intraepithelial lymphocytes expressing the HLA-E-specific natural killer receptor CD94 in celiac disease", Gastroenter. (2000) 118:867-879.
Jagielska et al., "Follow-up study of the first genome-wide association scan in alopecia areata: IL13 and KIAA0350 as susceptibility loci supported with genome-wide significance." J Invest Dermatol. (2012) 132:2192-2197.
Jespers et al., "Guiding the selection of human antibodies from phage display repertoires to a single epitope of an antigen". Biotechnology (1994) 12: 899-903.
Jespersen et al., "BepiPred-2.0: improving sequence-based B-cell epitope prediction using conformational epitopes". Nucleic Acids Res. (2017) 45(W1): W24-W29.
Kang et al., Rational Design of Interleukin-21 Antagonist through Selective Elimination of the C Binding Epitope, J Biol Chem. (2010) 285(16): 12223-12231.
Kivisäkk et al., "IL-15 mRNA expression is up-regulated in blood and cerebrospinal fluid mononuclear cells in multiple sclerosis (MS)", Clin Exp Immunol. (1998) 111(1):193-197.
Kluczyk et al., "The "two-headed" peptide inhibitors of interleukin-1 action," Peptides, (200), 21: 1411-1420.
Köhler et al., "Continuous cultures of fused cells secreting antibody of predefined specificity". Nature (1975) 256(5517): 495-497.
Kooy-Winkelaar et al., "CD4 T-cell cytokines synergize to induce proliferation of malignant and nonmalignant innate intraepithelial lymphocytes", Proc Natl Acad Sci U S A (2017)114(6):E980-989.
Kuczynski et al., "IL-15 is elevated in serum patients with type 1 diabetes mellitus." Diabetes Res Clin Pract. (2005) 69(3):231-236.
Laffleur et al., "Production of human or humanized antibodies in mice". Methods Mol Biol. (2012) 901:149-159.
Lazetic et al., "Human natural killer cell receptors involved in MHC class I recognition are disulfide-linked heterodimers of CD94 and NKG2 subunits". J Immunol. (1996) 157(11): 4741-4745.
Liu et al., "IL-15 is highly expressed in inflammatory bowel disease and regulates local T cell-dependent cytokine production." J Immunol. (2000) 164(7):3608-3615.
Lonberg et al., "Human antibodies from transgenic mice". Int Rev Immunol. (1995) 13: 65-93.
Maiuri L. et al., "Interleukin 15 Mediates Epithelial Changes in Celiac Desease", Gastroenter. (2000) 119:996-1006.
McInnes et al., "Interleukin-15 mediates T cell-dependent regulation of tumor necrosis factor-α production in rheumatoid arthritis." Nature Med. (1997) 3(2): 189-195.
Mention J-J. et al., "Interleukin 15: a key to disrupted intraepithelial lymphocyte homeostasis and lymphomagenesis in celiac disease", Gastroenter. (2003) 125(3):730-745.
Meresse et al., "Coordinated induction by IL15 of a TCR-independent NKG2D signaling pathway converts CTL into lymphokine-activated killer cells in celiac disease." Immunity (2004) 21(3):357-366.
Meresse et al., "The cytokine interleukin 21: a new player in coeliac disease ?. " Gut (2008) 57(7): 879-881.
Mingari et al., "HLA class I-specific inhibitory receptors in human T lymphocytes: interleukin 15-induced expression of CD94/NK62A in superantigen- or alloantigen-activated CD8+ T cells". Proc Natl Acad Sci. (1998) 95(3): 1172-1177.
Monteleone et al., "Interleukin-21 enhances T-helper cell type I signaling and interferon-γ production in Crohn's disease", Gastroenterology (2005) 128(3): 687-694.
Monteleone et al., "Characterization of IL-17A—Producing cells in celiac disease mucosa", J Immunol. (2010) 184: 2211-2218.
Nakou et al., "Interleukin-21 is increased in active systemic lupus erythematosus patients and contributes to the generation of plasma B cells." Clin Exp Rheumatol. (2013) 31(2):172-179.

(56) References Cited

OTHER PUBLICATIONS

Nohra et al., RGMA and IL21R show association with experimental inflammation and multiple sclerosis. Genes & Immunity, (2010) 11(4): 279-293.
Nowak E.C. et al., "IL-9 as a mediator of Th17-driven inflammatory disease", J Exp Med. (2009) 206:1653-1660.
Oppenheimer-Marks et al., "Interleukin 15 is produced by endothelial cells and increases the transendothelial migration of T cells In vitro and in the SCID mouse-human rheumatoid arthritis model In vivo." J Clin Invest (1998) 101(6):1261-1272.
Padlan E.A., "A possible procedure for reducing the immunogenicity of antibody variable (domains while preserving their ligand-binding properties". Mol Immunol. (1991) 28(4-5): 489-498.
Pashenkov et al., "Levels of interleukin-15-expressing blood mononuclear cells are elevated in multiple sclerosis", Scand J Immunol. (1999) 50(3):302-308.
Petukhova et al., "Genome-wide association study in alopecia areata implicates both innate and adaptive immunity." Nature (2010) 466(7302):113-117.
Price-Troska et al., Inhibiting IL-2 Signaling and the Regulatory T-Cell Pathway Using Computationally Designed Peptides, Invest New Drugs, (2018) 37(1): 9-16.
Recher et al., "IL-21 is the primary common γ chain-binding cytokine required for human B-cell differentiation in vivo". Blood (2011) 118(26): 6824-6835.
Richmond et al., "Antibody blockade of IL-15 signaling has the potential to durably reverse vitiligo". Sci Transl Med. (2018) 10(450).
Riechmann et al., "Reshaping human antibodies for therapy". Nature (1988) 332: 323-327.
Roguska et al., "Humanization of murine monoclonal antibodies through variable domain resurfacing". Proc Natl Acad Sci. (1994) 91(3): 969-973.
Rückert R. et al., "Interleukin-15 stimulates macrophages to activate $CD4_+$ T cells: a role in the pathogenesis of rheumatoid arthritis?", Immunology (2009) 126(1):63-73.
Saha et al., "Prediction of continuous B-cell epitopes in an antigen using recurrent neural network". Proteins (2006) 65: 40-48.
Saikali et al., "Contribution of astrocyte-derived IL-15 to CD8 T cell effector functions in multiple sclerosis", J Immunol. (2010) 185(10):5693-5703.
Sarra M. et al., "IL-15 positively regulates IL-21 production in celiac disease mucosa", Mucosal Immunol. (2013) 6(2):244-255.
Sawalha et al., "Genetic association of interleukin-21 polymorphisms with systemic lupus erythematosus", Ann Rheum Dis. (2008) 67(4):458-461.
Schaller et al., "Interleukin-2 receptor expression and interleukin-2 production in bullous pemphigoid". Arch Dermatol Res. (1990) 282(4): 223-226.
Schneider et al., "B cell-derived IL-15 enhances CD8 T cell cytotoxicity and is increased in multiple sclerosis patients", J Immunol. (2011) 187(8):4119-4128.
Schumacher et al., "Severe combined immunodeficiencies of the common g-chain/JAK3 signaling pathway." Isr. Med. Assoc. J. (2002) 4: 131-135.
Shultz et al., "Humanized mice for immune system investigation: progress, promise and challenges". Nat Rev Immunol. (2012) 12(11): 786-798.
Sonntag et al., "Chronic graft-versus-host-disease in CD34(+)-humanized NSG mice is associated with human susceptibility HLA haplotypes for autoimmune diseases". J Autoimmun. (2015) 62: 55-66.
Studnicka et al., "Human-engineered monoclonal antibodies retain full specific binding activity by preserving non-CDR complementarity-modulating residues". Protein Eng (1994) 7: 805-814.
Suarez-Farinas et al., "Alopecia areata profiling shows TH1, TH2, and IL-23 cytokine activation without parallel TH17/TH22 skewing." J Allergy Clin Immunol. (2015) 136(5): 1277-1287.

Sushama et al., "Cytokine profile (IL-2, IL-6, IL-17, IL-22, and TNF-alpha) in vitiligo—New insight into pathogenesis of disease". J Cosmet Dermatol. (2019) 18(1): 337-341.
Tang et al., "Cytosolic PLA2 is required for CTL-mediated immunopathology of celiac disease via NKG2D and IL-15." J Exp Med. (2009) 206(3): 707-719.
Terrier et al., "Interleukin 21 Correlates with T Cell and B Cell Subset Alterations in Systemic Lupus Erythematosus", J Rheumatol. (2012) 39(9):1819-1828.
Tomimatsu et al., "Antigen-specific in vitro immunization: a source for human monoclonal antibodies". Methods Mol Biol. (2014) 1060 (Chapter 15): 297-307.
Tzartos et al., "IL-21 and IL-21 Receptor Expression in Lymphocytes and Neurons in Multiple Sclerosis Brain", Am J Pathol. (2011) 178(2):794-802.
Vainer et al., "Colonic expression and synthesis of interleukin 13 and interleukin 15 in inflammatory bowel disease", Cytokine (2000) 12(10):1531-1536.
Vaknin-Dembinsky et al., "Membrane bound IL-15 is increased on CD14 monocytes in early stages of MS", J Neuroimmunol. (2008) 195(1-2):135-139.
Van Heel et al., "A genome-wide association study for celiac disease identifies risk variants in the region harboring IL2 and IL21." Nat Genet. (2007) 39(7): 827-829.
Vaughan et al., "Human Antibodies with Sub-nanomolar Affinities Isolated from a Large Non-immunized Phage Display Library". Nature (1996) 14(3): 309-314.
Villadsen et al., "Resolution of psoriasis upon blockade of IL-15 biological activity in a xenograft mouse model". J Clin Invest. (2003) 112: 1571-1580.
Waldmann, T.A., "The biology of IL-15: implications for cancer therapy and the treatment of autoimmune disorders." J Investig Dermatol Symp Proc. (2013) 16(1):S28-S30.
Walensky L.D. et al., "Hydrocarbon-Stapled Peptides: Principles, Practice, and Progress", Miniperspective; J Med Chem. (Aug. 2014) 57(15):6275-6288.
Williams et al., "Humanising Antibodies by CDR Grafting.", in: Antibody Engineering, eds R. Kontermann and S. Dübel (Springer—Berlin, Heidelberg); (2010) Chapter 21: 319-339.
Witkowski A. et al., "Conversion of a beta-Ketoacyl Synthase to a Malonyl Decarboxylase by Replacement of the Active-Site Cysteine with Glutamine", Biochem. (1999) 38:11643-11650.
Xing et al., "Alopecia areata is driven by cytotoxic T lymphocytes and is reversed by JAK inhibition." Nat Med. (2014) 9:1043-1049.
Xing et al., "Interleukin-21 induces migration and invasion of fibroblast-like synoviocytes from patients with rheumatoid arthritis", Clin Exp Immunol. (May 2016) 184(2):147-158.
Xing et al., "Interleukin-21 Induces Proliferation and Proinflammatory Cytokine Profile of Fibroblast-like Synoviocytes of Patients with Rheumatoid Arthritis", Scand J Immunol. (Jan. 2016) 83(1):64-71.
Yano et al., "Interleukin 15 induces the signals of epidermal proliferation through ERK and PI 3-kinase in a human epidermal keratinocyte cell line, HaCaT." Biochem Biophys Res Comm. (2003) 301(4): 841-847.
Yao et al., "SVMTriP: A Method to Predict Antigenic Epitopes Using Support Vector Machine to Integrate Tri-Peptide Similarity and Propensity". PLoS One (2012) 7(9): e45152.
Zanzi et al., "IL-15 interferes with suppressive activity of intestinal regulatory T cells expanded in Celiac disease." Am J Gastroenter (2011) 106(7): 1308-1317.
Zeng et al., "Synergy of IL-21 and IL-15 in regulating CD8+ T cell expansion and function." J Exp Med. (2005) 201(1): 139-148.
Notice of Acceptance dated Jan. 14, 2019 in Australian Application No. 2017200489.
Office Action dated Jun. 6, 2020 in Australian Application No. 2019202527.
Office Action regarding National Genetic Patrimony/Traditional Knowledge, dated Feb. 11, 2020, in Brazilian Application No. 1120130180463.
Office Action dated Dec. 19, 2019 for Canadian Patent Application No. 2824515.

(56) References Cited

OTHER PUBLICATIONS

Extended European Search Report dated Feb. 10, 2020 in European Application No. 19206731.2.
Office Action dated Jun. 23, 2020 in Japanese Application No. 2017-090501.
Office Action dated Sep. 29, 2020 in Japanese Application No. 2019-152602.
Office Action dated May 27, 2020 in Australian Application No. 2020201174.
Office Action dated Feb. 4, 2020 in in Canadian Application No. 3000207.
Office Action dated Mar. 27, 2020 for European Application No. 16854367.6.
Office Action dated May 19, 2020 in JP Patent Application No. 2018-517887.
International Search Report and Written Opinion dated Aug. 14, 2020 for PCT/US2020/030772.
Extended European Search Report dated Oct. 15, 2020 for Application No. 18780544.5.
Restriction Requirement dated Apr. 25, 2016 for U.S. Appl. No. 14/852,240.
Notice of Allowance dated Feb. 26, 2020 in U.S. Appl. No. 15/957,806.
Notice of Allowance dated Jun. 5, 2020 in U.S. Appl. No. 15/957,806.
Office Action dated Sep. 9, 2019 for U.S. Appl. No. 15/964,717.
Office Action dated Feb. 26, 2020 for U.S. Appl. No. 15/964,717.
Notice of Allowance dated Jul. 29, 2020 for U.S. Appl. No. 15/964,717.
Restriction Requirement dated Apr. 30, 2020 in U.S. Appl. No. 15/767,133.
Office Action dated Sep. 4, 2020 in U.S. Appl. No. 15/767,133.
Aoi et al., "IL-15 prevents allergic rhinitis through reactivation of antigen-specific CD8+ cells". J Aller Clin Immunol. (2006) 117(6): 1359-1366.
Boraschi et al., "Cytokine Receptors—Interleukin 2 Receptor Gamma—An overview", in Encyclopedia of Endocrine Diseases, (2004); downloaded from https://www.sciencedirect.com/topics/medicine-and-dentristry/interleukin-2-receptor-gamma; 2 pages.
Cagdas et al., "Genomic spectrum and phenotypic heterogeneity of human IL-21 receptor deficiency". J Clin Immunol. (Apr. 2021) 41: 1272-1290.
Crane et al., "Exercise-stimulated interleukin-15 is controlled by AMPK and regulates skin metabolism and aging." Aging Cell (2015) 14(4): 625-634.
Enose-Akahata et al., "Clinical trial of a humanized anti-IL-2/IL-15 receptor β chain in HAM/TSP." Ann Clin Translation Neurol. (2019) 6(8): 1383-1394.
Hiromura et al., "IL-21 Administration into the nostril alleviates murine allergic rhinitis". J Immunol. (2007) 179(10): 7157-7165.
Huang et al., "Nuclear factor-κB-dependent reversal of aging-induced alterations in T cell cytokines." Faseb J. (2008) 22(7): 2142-2150.
Mayo Clinic. "Hay Fever—Symptoms and Causes", Mayo Foundation for Medical Research (MFMER) © 1998-2021; 4 pages.
Nata et al., "Targeting the binding interface on a shared receptor subunit of a cytokine family enables the inhibition of multiple member cytokines with selectable target spectrum." Journal of Biological Chemistry (2015) 290(37): 22338-22351.
Nozuma et al., "Human T-lymphotropic virus type 1 (HTLV-1) and cellular immune response in HTLV-1-associated myelopathy/tropical spastic paraparesis." J NeuroVirol. (Jul. 2020) 26: 652-663.
Pepper et al., "Different routes of bacterial infection induce long-lived TH 1 memory cells and short-lived TH 17 cells." Nature Immunol.gy 11.1 (2010): 83-89.
Rajaei et al., "Role of IL-21 in HTLV-1 infections with empfasis on HTLV-1-associated myelopathy/tropical spastic paraparesis (HAM/TSP)." Med Microbiol Immunol. (2017) 206(3): 195-201.
Venkateshaiah et al., "Regulatory effects of IL-15 on allergen-induced airway obstruction". J Aller Clin Immunology 141.3 (2018): 906-917.

Wu et al., "IL-21 alleviates allergic asthma in DOCK8-knockout mice". Biochem Biophys Res Commun. (2018) 501(1): 92-99.
Office Action dated Oct. 21, 2021 in U.S. Appl. No. 15/767,133.
Office Action dated Apr. 23, 2019 in JP Patent Application No. 2017-90501.
Office Action dated Jun. 4, 2019 in JP Patent Application No. 2018-517887.
Office Action dated Aug. 16, 2019 for U.S. Appl. No. 15/957,806.
Yampolsky, L. et al., The Exchangeability of Amino Acids in Proteins, Genetics, 170, pp. 1459-1472, (2005).
Examination Report dated Nov. 14, 2018 in Australian Patent Application No. 2016334085.
Extended European Search Report dated Mar. 28, 2019 in European Patent Application No. 16854367.6.
Notice of Allowance dated Oct. 22, 2018 for U.S. Appl. No. 15/474,312.
Olosz, F. et al. Structural Basis for Binding Multiple Ligands by the Common Cytokine Receptor [gamma] -chain, Journal of Biological Chemistry, vol. 277, No. 14, pp. 12047-12052, (2002).
Office Action dated Jun. 22, 2018 for U.S. Appl. No. 15/474,312.
Office Action dated Nov. 23, 2018 in Canadian Application No. 2,824,51.
Office Action dated Nov. 26, 2018 in European Patent Application No. 12736203.6.
Office Action dated Jan. 31, 2019 in Canadian Patent Application No. 3,000,207.
Restriction Requirement dated Jan. 26, 2018 for U.S. Appl. No. 15/474,312.
Restriction Requirement dated Mar. 22, 2019 for U.S. Appl. No. 15/957,806.
Restriction Requirement dated Apr. 8, 2019 for U.S. Appl. No. 15/964,717.
Notice of Acceptance dated Jun. 11, 2021 for Australian Patent Application No. 2019202527.
Office Action dated Feb. 26, 2021 for Chinese Patent Application No. 201810863447.X.
Office Action dated Aug. 17, 2021 in Japanese Application No. 2019-152602.
Office Action dated Mar. 18, 2021 in Australian Application No. 2020201174.
Office Action dated May 12, 2021 in Australian Patent Application No. 2018250210.
Office Action dated Jul. 22, 2021 in U.S. Appl. No. 16/294,733.
Office Action dated Feb. 11, 2021 in U.S. Appl. No. 15/767,133.
Notice of Allowance dated Jul. 5, 2019 for EP Patent Application No. 12736203.6.
Office Action dated Sep. 25, 2019 for KR Patent Application No. 10-2018-7013183.
Office Action dated Oct. 28, 2019 for AU Patent Application No. 2016334085.
Ciszewski et al., Identification of a γc receptor antagonist that prevents reprogramming of human tissue-resident cytotoxic T cells by IL15 and IL21. Gastroenterol. (Feb. 1, 2020) 158(3): 625-637.
Office Action dated Jan. 29, 2021 in Canadian Application No. 2824515.
Office Action dated Sep. 24, 2021 in Chinese Application No. 201810863447.X.
Office Action dated Feb. 19, 2021 in European Application No. 19206731.2.
Office Action dated Feb. 23, 2021 in in Canadian Application No. 3000207.
Office Action dated Dec. 24, 2020 in Chinese Application No. 201680058779.X.
Office Action dated Sep. 17, 2021 in Chinese Application No. 201680058779.X.
Examination Report dated Dec. 9, 2020 in India Application No. 201817014941.
Office Action dated Feb. 8, 2022 in Japanese Patent Application No. 2019-554995.
International Search Report and Written Opinion dated Dec. 21, 2021 for PCT/US2021/038512.
Office Action dated Dec. 24, 2021 for U.S. Appl. No. 17/012,724.

(56) References Cited

OTHER PUBLICATIONS

Biology Online, "Codon", Definition from https://www.biologyonline.com/dictionary/codon; accessed May 26, 2022 (Year: 2022) 12 pages.
Gillies et al., "Bi-functional cytokine fusion proteins for gene therapy and antibody-targeted treatment of cancer". Cancer Immunol Immunother. (2002) 51: 449-460.
NCBI Reference Sequence: XP_012498189 Predicted: interleukin-15 [Propithecus coquereli], Jun. 1, 2015.
Abboud et al., Severe cytokine release syndrome after T cell-replete peripheral blood Haploidentical donor transplantation is associated with poor survival and anti-IL-6 therapy is safe and well tolerated. Biol Blood Marrow Transpl. Oct. 1, 2016;22(10):1851-1860.
Abdel-Hakeem M.S., Viruses teaching Immunology: Role of LCMV model and human viral infections in immunological discoveries. Viruses. Jan. 27, 2019;11(2):106 in 19 pages.
Abe R., Immunological Response in Stevens-Johnson Syndrome and Toxic Epidermal Necrolysis. J Dermatol. Jan. 2015;42(1):42-48.
Adusumilli et al., Regional delivery of mesothelin-targeted CAR T cell therapy generates potent and long-lasting CD4-dependent tumor immunity. Science Transl. Med. Nov. 5, 2014;6(261):261ra151 in 31 pages.
Agostini et al., Role of IL-15, IL-2, and their receptors in the development of T cell Alveolitis in pulmonary sarcoidosis. J Immunol. Jul. 15, 1996;157(2):910-918.
Agostini et al., New Pathogenetic Insights into the Sarcoid Granuloma. Curr Opin Rheumatol. Jan. 1, 2000;12(1):71-76.
Agouridakis et al., Association between Increased Levels of IL-2 and IL-15 and Outcome in Patients with Early Acute Respiratory Distress Syndrome. Eur J Clin Invest. Nov. 2002;32(11):862-867.
Allison et al., Association of interleukin-15-induced peripheral immune activation in persons coinfected with hepatitis C virus and HIV. J Infect Dis.Aug. 1, 2009;200(4):619-623.
Anonymous: "Equillium®—EQ101: A multi-specific cytokine inhibitor to treat alopecia areata". Presentation 6th Annual Dermatology Drug Development Summit; Equillium, Inc.; Nov. 1-3, 2022; 23 pages.
Antin et al., Cytokine dysregulation and acute graft-versus-host disease. Blood. Dec. 15, 1992;80(12):2964-2968.
Arras et al., Interleukin-9 reduces lung Fibrosis and type 2 immune polarization induced by silica particles in a murine model. Am J Resp Cell Mol Biol. Apr. 1, 2001;24(4):368-375.
Assier et al., NK Cells and Polymorphonuclear Neutrophils Are Both Critical for IL-2-Induced Pulmonary Vascular Leak Syndrome. J Immunol. Jun. 15, 2004;172(12):7661-7668.
Bae et al., Immune Response during Adverse Events after 17D-Derived Yellow Fever Vaccination in Europe. J Infect Dis. Jun. 1, 2008;197(11):1577-1584.
Baird et al., Multiplex immunoassay analysis of cytokines in idiopathic inflammatory myopathy. Arch Pathol Lab Med. Feb. 2008;132(2):232-238.
Baize et al., Early and Strong Immune Responses Are Associated with Control of Viral Replication and Recovery in Lassa Virus-Infected Cynomolgus Monkeys. J Virol. 2009; 83:5890-903.
Banadyga et al., The Cytokine Response Profile of Ebola Virus Disease in a Large Cohort of Rhesus Macaques Treated with Monoclonal Antibodies. Open Forum Infect Dis. 2019; 6:ofz046 in 6 pages.
Baraut et al., Relationship between cytokine profiles and clinical outcomes in patients with systemic sclerosis. Autoimmun Rev. 2010; 10:65-73.
Barnes et al., The Cytokine Network in Asthma and Chronic Obstructive Pulmonary Disease. J Clin Invest. 2008; 118:3546-3556.
Becker et al., Interleukin 15 Is Required for Proliferative Renewal of Virus-Specific Memory CD8 T Cells. J Exp Med. 2002; 195:1541-1548.
Belani et al., T Cell Activation and Cytokine Production in Anti-CD3 Bispecific Antibody Therapy. J Hematother. 1995; 4:395-402.

Belhadjer et al., Acute heart failure in multisystem inflammatory syndrome in children (MIS-C) in the context of global SARS-COV-2 pandemic. Circulation in press Aug. 4, 2020;142:429-436.
Bequignon et al., Pathogenesis of chronic rhinosinusitis with nasal polyps: Role of IL-6 in airway epithelial cell dysfunction. J Transl Med. 2020 ;18:136 in 12 pages.
Biber et al., Administration of two macrophage-derived interferon γ-inducing factors (IL-12 and IL-15) induces a lethal systemic inflammatory response in mice that is dependent on natural killer cells but does not require interferon-γ. Cell Immunol. Mar. 1, 2002;216(1-2):31-42.
Bixler et al., The Role of Cytokines and Chemokines in Filovirus Infection. Viruses 2015; 7:5489-5507.
Björkström et al., Rapid Expansion and Long-Term Persistence of Elevated NK Cell Numbers in Humans Infected with Hantavirus. J Exp Med. 2010; 208:13-21.
Blackwell et al., Sepsis and Cytokines: Current Status. Br J Anaesth. 1996; 77:110-7.
Blaser et al., Trans-Presentation of Donor-Derived Interleukin 15 Is Necessary for the Rapid Onset of Acute Graft-versus-Host Disease but Not for Graft-versus-Tumor Activity. Blood. 2006; 108:2463-2469.
Bonifant et al., Toxicity and Management in CAR T-Cell Therapy. Mol Ther Oncolytics. 2016; 3:16011 in 7 pages.
Boumba et al., Cytokine mRNA expression in the labial salivary gland tissues from patients with primary Sjögrens Syndrome. Br J Rheumatol. 1995; 34:326-333.
Braun et al., NK Cell Activation in Human Hantavirus Infection Explained by Virus-Induced IL-15/IL15Ra Expression. PLoS Pathog. 2014; 10:e1004521 in 12 pages.
Brisse et al., Hemophagocytic Lymphohistiocytosis (HLH): A Heterogeneous Spectrum of Cytokine- Driven Immune Disorders. Cytokine Growth Factor Rev. 2015; 26:263-280.
Brudno et al. Toxicities of Chimeric Antigen Receptor T Cells: Recognition and Management. Blood. 2016; 127:3321-3330.
Bruminhent et al., Acute Interstitial Pneumonia (Hamman-Rich Syndrome) as a Cause of Idiopathic Acute Respiratory Distress Syndrome. Case Rep Med. 2011; 2011:628743 in 5 pages.
Buchweitz et al., Time-Dependent Airway Epithelial and Inflammatory Cell Responses Induced by Influenza Virus A/PR/8/34 in C57BL/6 Mice. Toxicol Pathol. 2007; 35:424-435.
Cahill et al. Circulating Factors in Trauma Plasma Activate Specific Human Immune Cell Subsets. Injury 2020; 51:819-829.
Caproni et al., Expression of Cytokines and Chemokine Receptors in the Cutaneous Lesions of Erythema Multiforme and Stevens-Johnson Syndrome/Toxic Epidermal Necrolysis. Br J Dermatol. 2006; 155:722-728.
Carding et al., Activation of Cytokine Genes in T Cells during Primary and Secondary Murine Influenza Pneumonia. J Exp Med. 1993; 177:475-482.
Carey et al., Neutrophil Activation, Vascular Leak Toxicity, and Cytolysis during Interleukin-2 Infusion in Human Cancer. Surgery. 1997; 122:918-926.
Cerar et al., Diagnostic value of cytokines and chemokines in Lyme neuroborreliosis. Clin Vaccine Immunol. 2013; 20:1578-1584.
Channappanavar et al., Pathogenic Human Coronavirus Infections: Causes and Consequences of Cytokine Storm and Immunopathology. Semin Immunopathol. Jul. 2017;39(5):529-539.
Chaturvedi et al., Cytokine Cascade in Dengue Hemorrhagic Fever: Implications for Pathogenesis. FEMS Immunol Med Microbiol. Jul. 1, 2000;28(3):183-188.
Chen et al., Cellular Immune Responses to Severe Acute Respiratory Syndrome Coronavirus (SARS- CoV) Infection in Senescent BALB/c Mice: CD4+ T Cells Are Important in Control of SARS-CoV Infection. J Virol. Feb. 1, 2010;84(3):1289-1301.
Chen et al., Elevated Cytokine Levels in Tears and Saliva of Patients with Primary Sjögren's Syndrome Correlate with Clinical Ocular and Oral Manifestations. Sci Rep. May 13, 2019;9(1):7319 in 10 pages.
Chi et al., Cytokine and Chemokine Levels in Patients Infected with the Novel Avian Influenza A (H7N9) Virus in China. J Infect Dis. Dec. 15, 2013;208(12):1962-1967.

(56) References Cited

OTHER PUBLICATIONS

Chien et al., Temporal Changes in Cytokine/Chemokine Profiles and Pulmonary Involvement in Severe Acute Respiratory Syndrome. Respirology. Nov. 2006;11(6):715-722.
Chiotos et al., Multisystem Inflammatory Syndrome in Children during the COVID-19 pandemic: A Case Series. J Pediatr Infect Dis Soc. Jul. 2020;9(3):393-398.
Chung et al., Recent Advances in the Genetics and Immunology of Stevens-Johnson Syndrome and Toxic Epidermal Necrosis. J Dermatol Sci. Jun. 1, 2012;66(3):190-196.
Cicardi et al., The Systemic Capillary Leak Syndrome: Appearance of Interleukin-2-Receptor-Positive Cells during Attacks. Ann Intern Med. Sep. 15, 1990;113(6):475-477.
Ciccia et al., Difference in the expression of IL-9 and IL-17 correlates with different histological pattern of vascular wall injury in giant cell arteritis. Rheumatology. Sep. 1, 2015;54:1596-1604.
Clay et al., Severe acute respiratory syndrome—Coronavirus Infection in Aged Nonhuman Primates is Associated with Modulated Pulmonary and Systemic Immune Responses. Immun Ageing. Dec. 2014; 11(1):1-6.
Cron et al., Cytokine Storm Syndrome. 2019 Cham: Springer International Publishing; TOC (17 pages).
D'Elia et al., Targeting the "cytokine storm" for therapeutic benefit. Clin Vaccine Immunol. Mar. 2013;20(3):319-327.
De Maria et al., CD3+4-8-WT31-(T Cell Receptor y+) Cells and Other Unusual Phenotypes Are Frequently Detected among Spontaneously Interleukin 2-Responsive T Lymphocytes Present in the Joint Fluid in Juvenile Rheumatoid Arthritis. A Clonal Analysis. Eur J Immunol. 1987; 17:1815-1819.
De Paepe et al., Scanning for Therapeutic Targets within the Cytokine Network of Idiopathic Inflammatory Myopathies. Int J Mol Sci. Aug. 11, 2015;16(8):18683-18713.
Dolinger et al., Pediatric Crohn's Disease and Multisystem Inflammatory Syndrome in Children (MIS- C) and COVID-19 Treated with Infliximab. J Pediatr Gastroenterol Nutr. May 5, 2020;71(2):153-155.
Dong et al., IL-9 Induces Chemokine Expression in Lung Epithelial Cells and Baseline Airway Eosinophilia in Transgenic Mice. Eur J Immunol. Jul. 1999;29(7):2130-2139.
Duan et al. Regulatory mechanisms, prophylaxis and treatment of vascular leakage following severe trauma and shock. Milit. Med Res. Dec. 2017;4(1):11 in 11 pages.
Endo et al., Two types of septic shock classified by the plasma levels of cytokines and endotoxin. 1992 Circ Shock. Dec. 1, 1992;38(4):264-274.
Engelmann et al., Pathophysiologic and Transcriptomic Analyses of Viscerotropic Yellow Fever in a Rhesus Macaque Model. PLoS Negl Trop Dis. 2014 8:e000329 in 16 pages.
Ermler et al.,RNA Helicase Signaling Is Critical for Type I Interferon Production and Protection against Rift Valley Fever Virus during Mucosal Challenge. J Virol. May 1, 2013;87(9):4846-4860.
Fadeel et al., Induction of Apoptosis and Caspase Activation in Cells Obtained from Familial Haemophagocytic Lymphohistiocytosis Patients. Br J Haematol. Aug. 1999;106(2):406-145.
Falasca et al., Molecular Mechanisms of Ebola Virus Pathogenesis: Focus on Cell Death. Cell Death Differ. Aug. 2015;22(8):1250-1259.
Faulkner et al., The Mechanism of Superantigen-Mediated Toxic Shock: Not a Simple Th1 Cytokine Storm. J Immunol. Nov. 15, 2005;175(10):6870-6877.
Forrester et al., TCR Expression of Activated T Cell Clones in the Lungs of Patients with Pulmonary Sarcoidosis. J Immunol. Nov. 1, 1994;153(9):4291-4302.
Fox et al., Cytokine MRNA Expression in Salivary Gland Biopsies of Sjögren's Syndrome. J Immunol. Jun. 1, 1994;152(11):5532-553.
Friberg et al., Protective versus Pathologic Pre-Exposure Cytokine Profiles in Dengue Virus Infection. PLoS Negl Trop Dis. Dec. 17, 2018;12(12):e0006975 in 15 pages.
Frohna et al., "B-102: Results from a First-in-human Study with BNZ-1, a novel, selective inhibitor of IL-2, IL-9, and IL-15 at the common gamma-chain receptor, in clinical development for the treatment of HAM/TSP and T-cell malignancies". 19th Int'l Meeting of the Institute of Human Virology—Jan. 1, 2018; Abstract; 1 page.
Frohna et al., "LB1517 Clinical effects of BNZ-1, a selective inhibitor of IL-2/IL-9/IL15 in development for alopecia areata". J Invest Dermatol. Sep. 2018; Abstract p. B9-B10.
Funke et al., Capillary Leak Syndrome Associated with Elevated IL-2 Serum Levels after Allogeneic Bone Marrow Transplantation. Ann Hematol. Jan. 1994;68(1):49-52.
Gogishvili et al., Rapid regulatory T-cell response prevents cytokine storm in CD28 superagonist treated mice. PLoS One. Feb. 27, 2009;4(2):e4643 in 9 pages.
Gono et al., Cytokine profiles in polymyositis and dermatomyositis complicated by rapidly progressive or chronic interstitial lung disease. Rheumatology. Dec. 1, 2014;53(12):2196-2203.
Gourh et al., Polymorphisms in TBX21 and STAT4 increase the risk of systemic sclerosis: Evidence of possible gene-gene interaction and alterations in Th1/Th2 cytokines. Arthritis Rheum. Dec. 2009;60(12):3794-3806.
Guo et al., Coronavirus Disease 2019 (COVID-19) and Cardiovascular Disease: A Viewpoint on the Potential Influence of Angiotensin-Converting Enzyme Inhibitors/Angiotensin Receptor Blockers on Onset and Severity of Severe Acute Respiratory Syndrome Coronavirus 2 Infection. J Am Heart Assoc. Apr. 9, 2020;9(7):e0162219 in 5 pages.
Guo et al., The Serum Profile of Hypercytokinemia Factors Identified in H7N9-Infected Patients Can Predict Fatal Outcomes. Sci Rep. 2015;5(1):srep10942 in 10 pages.
Guo et al., IL-15 Superagonist-Mediated Immunotoxicity: Role of NK Cells and IFN-γ. J Immunol. Sep. 1, 2015;195(5):2353-2364.
Guo et al., IL-15 Enables Septic Shock by Maintaining NK Cell Integrity and Function. J Immunol. Feb. 1, 2017;198(3):1320-1333.
Guo et al., The Origin, Transmission and Clinical Therapies on Coronavirus Disease 2019 (COVID-19) Outbreak—An Update on the Status. Military Med Res. Dec. 2020;7(1):10 pages.
Han et al., The acute respiratory distress syndrome: from mechanism to translation. J Immunol. Feb. 1, 2015;194(3):855-860.
Han et al., Cytokine profiles as novel diagnostic markers of Epstein-Barr virus-associated hemophagocytic lymphohistiocytosis in children. J Crit Care. Jun. 1, 2017;39:72-77.
Hao et al., Mathematical Model of Sarcoidosis. PNAS. Nov. 11, 2014;111(45):16065-16070.
Harris et al.,. Reciprocal Regulation of Polarized Cytokine Production by Effector B and T Cells. Nat Immunol. Dec. 2000;1(6):475-482.
Haugen et al., Cytokine Concentrations in Plasma from Children with Severe and Non-Severe Community Acquired Pneumonia. PLoS One. Sep. 25, 2015;10(9):e0138978 in 16 pages.
Hechinger et al., Therapeutic Activity of Multiple Common γ-chain Cytokine Inhibition in acute and chronic GVHD. Blood. Jan. 15, 2015;125(3):570-580.
Hogaboam et al., Differential monocyte chemoattractant protein-1 and chemokine receptor 2 expression by murine lung fibroblasts derived from Th1- and Th2-type pulmonary granuloma models. J Immunol. Aug. 15, 1999;163(4):2193-2201.
Hondowicz et al., Interleukin-2-Dependent Allergen-Specific Tissue-Resident Memory Cells Drive Asthma. Immunity. Jan. 19, 2016;44(1):155-166.
Hornef et al., Cytokine production in a whole-blood assay after Epstein-Barr virus infection in vivo. Clin Diagn Lab Immunol. Mar. 1995;2(2):209-213.
Huang et al. Innate and Adaptive Immune Responses in Patients with Pandemic Influenza A(H1N1)pdm09. Arch Virol. Nov. 2013;158(11):2267-2272.
Huang et al., Clinical Features of Patients Infected with 2019 Novel Coronavirus in Wuhan, China. Lancet. Feb. 15, 2020;395(10223):497-506.
Hunninghake et al., Mechanisms of Hypergammaglobulinemia in Pulmonary Sarcoidosis: Site of Increased Antibody Production and Role of T Lymphocytes. J Clin Invest. Jan. 1, 1981;67(1):86-92.

(56) References Cited

OTHER PUBLICATIONS

Jabri et al., IL-15 Functions as a Danger Signal to Regulate Tissue-Resident T Cells and Tissue Destruction. Nat Rev Immunol. Dec. 2015;15(12):771-783.
Jarvis et al., Neutrophils: The Forgotten Cell in JIA Disease Pathogenesis. Pedia Rheumatol Online. Dec. 2007;5(1):1-8.
Jia et al., Detection of IL-9 Producing T Cells in the PBMCs of Allergic Asthmatic Patients. BMC immunol. Dec. 2017;18(1):1-9.
Jillella et al., Non-Hodgkins Lymphoma Presenting as Anasarca: Probably Mediated by Tumor Necrosis Factor Alpha (TNF-α). Leuk Lymph. Jan. 1, 2000;38(3-4):419-22.
Jiménez-sousa et al., IL15 Polymorphism is Associated with Advanced Fibrosis, Inflammation-Related Biomarkers and Virological Response in Human Immunodeficiency Virus/Hepatitis C Virus Coinfection. Liver Int. Jan. 2016;36:1258-1266.
Kahaleh et al., Interleukin-2 in scleroderma: Correlation of serum level with extent of skin involvement and disease duration. Ann Intern Med. Mar. 15, 1989;110(6):446-450.
Kalyan et al., Human Peripheral Gammadelta T Cells Potentiate the Early Proinflammatory Cytokine Response to Staphylococcal Toxic Shock Syndrome toxin-1. J Infect Dis. May 15, 2004;189(10):1892-1896.
Kappler et al., V Beta-Specific Stimulation of Human T Cells by Staphylococcal Toxins. Science. May 19, 1989;244(4906):811-813.
Khan et al., IL-2 Regulates SEB Induced Toxic Shock Syndrome in BALB/c Mice. PLoS One. Dec. 29, 2009;4(12):e8473 in 6 pages.
Kim et al., Targeting the IL-15 Receptor with an Antagonist IL-15 Mutant/Fcγ2a Protein Blocks Delayed-Type Hypersensitivity. J Immunol. Jun. 15, 1998;160(12):5742-5748.
Kimber et al., Toxic Shock Syndrome: Characterization of Human Immune Responses to TSST-1 and Evidence for Sensitivity Thresholds. Toxicol Sci. Jul. 1, 2013;134(1):49-63.
Kimura et al., The Postoperative Serum Interleukin-15 Concentration Correlates with Organ Dysfunction and the Prognosis of Septic Patients Following Emergency Gastrointestinal Surgery. J Surg Res. Jun. 15, 2012;175(2):e83-88.
Klingström et al., Innate and Adaptive Immune Responses against Human Puumala Virus Infection: Immunopathogenesis and Suggestions for Novel Treatment Strategies for Severe Hantavirus-Associated Syndromes. J Intern Med. May 2019; 285(5):510-523.
Koh et al., Levels of Interleukin-2, Interferon-gamma, and Interleukin-4 in Bronchoalveolar Lavage Fluid from Patients with Mycoplasma Pneumonia: Implication of Tendency Toward Increased Immunoglobulin E Production. Pediatrics. Mar. 1, 2001;107(3):E39-E45.
Krakauer T., Immune Response to Staphylococcal Superantigens. Immunol Res. Dec. 1999;20(3):163-173.
Krieg et al., Improved IL-2 immunotherapy by selective stimulation of IL-2 receptors on lymphocytes and endothelial cells. PNAS. Jun. 29, 2010;107(26):11906-11911.
Kurane et al., Activation of T Lymphocytes in Dengue Virus Infections. High Levels of Soluble Interleukin 2 Receptor, Soluble CD4, Soluble CD8, Interleukin 2, and Interferon-Gamma in Sera of Children with Dengue. J Clin Invest. Nov. 1, 1991;88(5):1473-1480.
Kushner et al., Immune Biomarker Differences and Changes Comparing HCV Mono-Infected, HIV/HCV Co-Infected, and HCV Spontaneously Cleared Patients. PLoS One. Apr. 4, 2013;8(4):e60387 in 17 pages.
Lamparello et al., Severely Injured Trauma Patients with High Circulating IL-15 Levels Display Worse Outcomes and Distinct Inflammatory Profiles, Suggesting a Role for Natural Killer Cell Activation. J Am Coll Surg. Oct. 1, 2019;229(4):S310.
Lashine et al., Correcting the Expression of MiRNA-155 Represses PP2Ac and Enhances the Release of IL-2 in PBMCs of Juvenile SLE Patients. Lupus. Mar. 2, 2015;24(3):240-247.
Leahy et al., Interleukin-15 Is Associated with Disease Severity in Viral Bronchiolitis. Eur Resp J. Jan. 1, 2015;47(1):212-222.
Lee et al. Regulation of CAR T Cell-Mediated Cytokine Release Syndrome-like Toxicity Using Low Molecular Weight Adapters. Nat Commun. Jun. 18, 2019;10(1):1-11.
Lentsch et al., Mechanisms of Leukocyte-Mediated Tissue Injury Induced by Interleukin-2. Cancer Immunol Immunother. Jan. 1999;47(5):243-248.
Lesur et al., Interleukin-2 Involvement in Early Acute Respiratory Distress Syndrome: Relationship with Polymorphonuclear Neutrophil Apoptosis and Patient Survival. Crit Care Med. Dec. 1, 2000;28(12):3814-3822.
Li et al., Structure-Function Studies of T-Cell Receptor-Superantigen Interactions. Immunol Rev. Jun. 1998;163(1):177-186.
Li et al., CD3 bispecific antibody-induced cytokine release is dispensable for cytotoxic T cell activity. Sci Transl Med. Sep. 4, 2019;11(508):eaax8861 in 13 pages.
Li et al., IL-9 Deficiency Promotes Pulmonary Th17 Response in Murine Model of Pneumocystis Infection. Front Immunol. May 25, 2018;9:Art1118 in 16 pages.
Li et al., Coronavirus Neurovirulence Correlates with the Ability of the Virus to Induce Proinflammatory Cytokine Signals from Astrocytes and Microglia. J Virol. Apr. 1, 2004;78(7):3398-3406.
Lin et al., Expression and regulation of interleukin-9 in chronic rhinosinusitis. Am J Rhinol Allergy. Jan. 2015;29(1):e18-e23.
Lin et al., Temporal Characterization of Marburg Virus Angola Infection Following Aerosol Challenge in Rhesus Macaques. J Virol. Oct. 1, 2015;89(19):9875-9885.
Linde et al., Serum levels of lymphokines and soluble cellular receptors in primary Epstein-Barr virus infection and in patients with chronic fatigue syndrome. J Infect Dis. Jun. 1, 1992;165(6):994-1000.
Link et al., Anti-CD3-based Bispecific Antibody Designed for Therapy of Human B-cell Malignancy can Induce T-cell Activation by Antigen-Dependent and Antigen-Independent Mechanisms. Int J Cancer. Jul. 1, 19987;77(2):251-256.
Lisi et al., Sjögrens Syndrome Autoantibodies Provoke Changes in Gene Expression Profiles of Inflammatory Cytokines Triggering a Pathway Involving TACE/NF-κB. Lab Invest. Apr. 2012;92(4):615-624.
Liu et al., Differences in Inflammatory Marker Patterns for Adult Community-Acquired Pneumonia Patients Induced by Different Pathogens. Clin Respir J. Mar. 2018;12(3):974-985.
Liu et al., Overlapping and Discrete Aspects of the Pathology and Pathogenesis of the Emerging Human Pathogenic Coronaviruses SARS-CoV, MERS-CoV, and 2019-NCOV. J Med Virol. May 2020; 92(5):491-494.
Liu et al., Longitudinal Characteristics of Lymphocyte Responses and Cytokine Profiles in the Peripheral Blood of SARS-CoV-2 Infected Patients. EBioMedicine. May 1, 2020;55:102763 in 17 pages.
Logan et al., Increased disease activity in a patient with sarcoidosis after high dose interleukin 2 treatment for metastatic renal cancer. Thorax. Jul. 1, 2005;60(7):610-611.
Lotz et al., Release of lymphokines after Epstein Barr virus infection in vitro. I. Sources of and kinetics of production of interferons and interleukins in normal humans. J Immunol. May 15, 1986;136(10):3636- 3642.
Lourdes et al., Systemic Capillary Leak Syndrome as an Initial Presentation of ALK-Negative Anaplastic Large Cell Lymphoma. Case Rep Hematol. Mar. 26, 2012;2012:Article ID 954201 in 4 pages.
Macaubas et al., Oligoarticular and Polyarticular JIA: Epidemiology and Pathogenesis. Nat Rev Rheumatol. Nov. 2009;5(11):616-626.
Mahallawi et al., MERS-CoV Infection in Humans Is Associated with a pro-Inflammatory Th1 and Th17 Cytokine Profile. Cytokine. Apr. 1, 2018;104:8-13.
Makarevich et al., Interleukin-2 (IL-2) and Interferon-γ (IFN-γ) in Identifying Severe Community-Acquired Pneumonia (SCAP) Clinical Outcomes and Complications. Eur Resp J. 2011;38:1474;Abstract.
Maleki et al., Serum Markers Associated with Severity and Outcome of Hantavirus Pulmonary Syndrome. J Infect Dis. May 5, 2019;219(11):1832-1840.

(56) References Cited

OTHER PUBLICATIONS

Massoud et al., Common γ-chain 1,9, 15 blocking peptide reduces in vitro immune activation markers in HTLV-1-associated myelopathy/tropical spastic paraparesis. PNAS. Sep. 1, 2015;112(35):11030-11035.

McElroy et al., Ebola Hemorrhagic Fever: Novel Biomarker Correlates of Clinical Outcome. J Infect Dis. Aug. 15, 2014;210(4):558-566.

McElroy et al., Human Ebola Virus Infection Results in Substantial Immune Activation. PNAS. Apr. 14, 2015;112(15):4719-4724.

McKinstry et al., Memory CD4 T Cell-Derived IL-2 Synergizes with Viral Infection to Exacerbate Lung Inflammation. PLoS Pathog. Aug. 14, 2019;15(8):e1007989 in 24 pages.

Mehta et al., COVID-19: Consider Cytokine Storm Syndromes and Immunosuppression. Lancet. Mar. 28, 2020;395(10229):1033-1034.

Mo et al., Induction of Cytokines in Mice with Parainfluenza Pneumonia. J Virol. Feb. 1995;69(2):1288- 1291.

Moretti et al., A Mast Cell-ILC2-Th9 Pathway Promotes Lung Inflammation in Cystic Fibrosis. Nat Commun. Jan. 16, 2017;8(1):14017 in 13 pages.

Mori et al., High Levels of Cytokine-Producing Cells in the Lung Tissues of Patients with Fatal Hantavirus Pulmonary Syndrome. J Infect Dis. Feb. 1, 1999;179(2):295-302.

Muro et al., Expression of IL-15 in Inflammatory Pulmonary Diseases. J Allergy Clin Immunol. Dec. 1, 2001;108(6):970-975.

Nakamura et al., Interleukin-15 Is Critical in the Pathogenesis of Influenza A Virus-Induced Acute Lung Injury. J Virol. Jun. 1, 2010;84(11):5574-5582.

Needleman et al., Interleukin-1, interleukin-2, interleukin-4, interleukin-6, tumor necrosis factor α, and interferon-γ levels in sera from patients with scleroderma. Arthritis Rheum. Jan. 1992;35(1):67-72.

Nordberg et al., Cytotoxic mechanisms may play a role in the local immune response in the central nervous system in neuroborreliosis. J Neuroimmunol. Mar. 1, 2011;232(1-2):186-193.

Notarnicola et al., Correlation between serum levels of IL-15 and IL-17 in patients with idiopathic inflammatory myopathies. Scand J Rheumatol. May 4, 2015;44(3):224-228.

Okamoto et al., Interleukin 18 (IL-18) in Synergy with IL-2 Induces Lethal Lung Injury in Mice: A Potential Role for Cytokines, Chemokines, and Natural Killer Cells in the Pathogenesis of Interstitial Pneumonia. Blood Feb. 15, 2002;99(4):1289-1298.

Olcott et al., Interleukin-9 and interleukin-17C in chronic rhinosinusitis. Int Forum Allergy Rhinol. Aug. 2016:6(8):841-847.

Orucevic et al., Role of nitric oxide in IL-2 therapy-induced capillary leak syndrome. Cancer Metastasis Rev. Mar. 1998; 17(1):127-142.

Outinen et al., Thrombocytopenia Associates with the Severity of Inflammation and Variables Reflecting Capillary Leakage in Puumala Hantavirus Infection, an Analysis of 546 Finnish Patients. Infect Dis (Lond) Sep. 1, 2016;48(9):682-687.

Ozsurekci et al., Can the Mild Clinical Course of Crimean-Congo Hemorrhagic Fever in Children Be Explained by Cytokine Responses? J Med Virol. Nov. 2013; 85(11):1955-1959.

Panupattanapong et al., New spectrum of COVID-19 manifestations in children: Kawasaki-like syndrome and hyperinflammatory response. Cleve Clin J Med. Dec. 31, 2020; in 7 pages.

Papa et al., Emergence of Crimean-Congo Haemorrhagic Fever in Greece. Clin Microbiol Infection. Jul. 1, 2009;16(7):843-847.

Papa et al., Cytokines as Biomarkers of Crimean-Congo Hemorrhagic Fever. J Med Virol. Jan. 2016;88(1):21-27.

Parsonnet et al., Mediators in the Pathogenesis of Toxic Shock Syndrome: Overview. Rev Infect Dis. Jan. 1, 1989;S263-S269.

Patro et al., Cytokine Signature Associated with Disease Severity in Dengue. Viruses. Jan. 8, 2019;11(1):34 in 12 pages.

Pattanaik et al., Pathogenesis of Systemic Sclerosis. Front Immunol. Jun. 8, 2015;6:272 in 40 pages.

Pietikäinen et al., Cerebrospinal fluid cytokines in Lyme neuroborreliosis. J Neuroinflam. Dec. 2016;13(1):273 in 10 pages.

Poust et al., Management of Toxicities Associated with High-Dose Interleukin-2 and Biochemotherapy. Anticancer Drugs. Jan. 1, 2013;24(1):1-13.

Prasse et al., Th1 Cytokine Pattern in Sarcoidosis Is Expressed by Bronchoalveolar CD4 and CD8 T Cells. Clin Exp Immunol. Nov. 2000; 122(2):241-248.

Prior et al., Increased Levels of Serum Interferon-Gamma in Pulmonary Sarcoidosis and Relationship with Response to Corticosteroid Therapy. Am Rev Respir Dis. Jan. 1, 1991;143(1):53-60.

Rafi et al.,Evidence for the Involvement of Fas Ligand and Perforin in the Induction of Vascular Leak Syndrome. J Immunol. Sep. 15, 1998;161(6):3077-3086.

Rai et al., Serum Cytokine Profile in Patients with Chronic Rhinosinusitis with Nasal Polyposis Infected by Aspergillus flavus. Ann Lab Med. Mar. 28, 2018;38(2):125-131.

Ramos-Casals et al., Adult Haemophagocytic Syndrome. Lancet. Apr. 26, 2014;383(9927):1503-1516.

Rauer et al., Lyme Neuroborreliosis. Dtsch Arztebl Int 2018 ;115:751-756.

Robinson et al., Gamma Interferon Is Spontaneously Released by Alveolar Macrophages and Lung T Lymphocytes in Patients with Pulmonary Sarcoidosis. J Clin Invest May 1, 1985;75(5):1488-1495.

Roediger et al., IL-2 Is a Critical Regulator of Group 2 Innate Lymphoid Cell Function during Pulmonary Inflammation. J Allergy Clin Immunol. Dec. 1, 2015;136(6):1653-1663.

Ruiz et al., Animal Models of Human Viral Diseases. In Animal Models for the Study of Human Disease. 2013; Chapter 38: 927-970.

Ruprecht et al., Coexpression of CD25 and CD27 Identifies FoxP3+ Regulatory T Cells in Inflamed Synovia. J Exp Med. Jun. 6, 2005;201(11):1793-1803.

Russier et al., The Exonuclease Domain of Lassa Virus Nucleoprotein Is Involved in Antigen- Presenting-Cell-Mediated NK Cell Responses. J Virol. Dec. 1, 2014;88(23):13811-13820.

Sadeghi et al., Cytokine Expression during Early and Late Phase of Acute Puumala Hantavirus Infection. BMC Immunol. Dec. 2011; 12(1):65 in 10 pages.

Sambatakou et al., Cytokine Profiling of Pulmonary Aspergillosis. Int J Immunogenet. Aug. 2006;33(4):297-302.

Sarawar et al., Cytokine Profiles of Bronchoalveolar Lavage Cells from Mice with Influenza Pneumonia: Consequences of CD4+ and CD8+ T Cell Depletion. Reg Immunol. May 1993;5(3-4):142- 150.

Sarawar et al., Concurrent Production of Interleukin-2, Interleukin-10, and γ Interferon in the Regional Lymph Nodes of Mice with Influenza Pneumonia. J Virol. May 1994;68(5):3112-3119.

Schaeffer et al., Lassa Virus Activates Myeloid Dendritic Cells but Suppresses Their Ability to Stimulate T Cells. PLoS Pathog. Nov. 12, 2018;14(11):e1007430 in 25 pages.

Schaeffer et al., Non-Pathogenic Mopeia Virus Induces More Robust Activation of Plasmacytoid Dendritic Cells than Lassa Virus. Viruses. Mar. 21, 2019;11(3):287 in 9 pages.

Schlosser et al., Mucous Cytokine Levels in Chronic Rhinosinusitis—Associated Olfactory Loss. JAMA Otolaryngol Head Neck Surg. Aug. 1, 2016;142(8):731-737.

Schulert et al., Macrophage Activation Syndrome and Cytokine-Directed Therapies. Best Pract Res Clin Rheumatol. Apr. 1, 2014;28(2):277-292.

Segawa et al., Inhibition of Transforming Growth Factor-β Signalling Attenuates Interleukin (IL)-18 plus IL-2-Induced Interstitial Lung Disease in Mice. Clin Exp Immunol. 2010;160:394-402.

Semenzato et al., Immune Mechanisms in Interstitial Lung Diseases. Allergy. Dec. 2000;55(12):1103- 1120.

Shaw et al., Weathering a Cytokine Storm: A Case of EBV-Induced Hemophagocytic Lymphohistiocytosis. J Invest Med High Impact Case Rep. Apr. 28, 2016;4(2):1-5.

Shimbara et al., IL-9 and Its Receptor in Allergic and Nonallergic Lung Disease: Increased Expression in Asthma. J Allergy Clin Immunol. Jan. 1, 2000;105(1):108-115.

Silversides et al., Staphylococcal Toxic Shock Syndrome: Mechanisms and Management. Curr Infect Dis Rep. Sep. 2010;12(5):392-400.

(56) References Cited

OTHER PUBLICATIONS

Singer et al., The Third International Consensus Definitions for Sepsis and Septic Shock (Sepsis-3). JAMA. Feb. 23, 2016;315(8):801-810.
Sisto et al., Interleukin-15 as a Potential New Target in Sjögrens Syndrome-Associated Inflammation. Pathology. Oct. 1, 2016;48(6):602-607.
Sisto et al., TLR2 Signals via NF-κB to Drive IL-15 Production in Salivary Gland Epithelial Cells Derived from Patients with Primary Sjögren's Syndrome. Clin Exp Med. Aug. 2017;17(3):341-350.
Smith et al., Persistent Crimean-Congo Hemorrhagic Fever Virus Infection in the Testes and within Granulomas of Non-Human Primates with Latent Tuberculosis. PLoS Pathog. Sep. 26, 2019;15(9):e1008050 in 22 pages.
Smith et al., A Prominent Role for the IL1 Pathway and IL15 in Susceptibility to Chronic Cavitary Pulmonary Aspergillosis. Clin Microbiol Infect. Aug. 1, 2014;20(8):O480-O488.
Smith et al., Clinical Implications of Interferon -. Genetic and Epigenetic Variants. Immunology. Dec. 2014;143(4):499-511.
Smolewska et al., Regulation of Peripheral Blood and Synovial Fluid Lymphocyte Apoptosis in Juvenile Idiopathic Arthritis. Scand J Rheumatol. Jan. 1, 2004;33(1):7-12.
Soussi-Gounni et al., Role of IL-9 in the Pathophysiology of Allergic Diseases. J Allergy Clin Immunol. Apr. 1, 2001;107(4):575-582.
Stern et al., Stevens-Johnson Syndrome and Toxic Epidermal Necrolysis: Associations, Outcomes, and Pathobiology—Thirty Years of Progress but Still Much to be Done. J Invest Dermatol. May 1, 2017;137(5):1004-1008.
Streckfus et al., Cytokine Concentrations in Stimulated Whole Saliva among Patients with Primary Sjogren's Syndrome, Secondary Sjögrens Syndrome, and Patients with Primary Sjögrens Syndrome Receiving Varying Doses of Interferon for Symptomatic Treatment of the Condition: A Preliminary Study. Clin Oral Investig. Jun. 2001;5(2):133-135.
Strengell et al., IL-21 in Synergy with IL-15 or IL-18 Enhances IFN-γ Production in Human NK and T Cells. J Immunol. Jun. 1, 2003;170(11):5464-5469.
Su et al., Interleukin-15 Is Associated with Severity and Mortality in Stevens-Johnson Syndrome/Toxic Epidermal Necrolysis. J Invest Dermatol. May 1, 2017;137(5):1065-1073.
Sugimoto et. al., IL-9 Blockade Suppresses Silica-Induced Lung Inflammation and Fibrosis in Mice. Am J Respir Cell Mol Biol. Feb. 2019;60(2):232-243.
Sullivan et al., Ebola Virus Pathogenesis: Implications for Vaccines and Therapies. J Virol. Sep. 15, 2003;77(18):9733-9737.
Suntharalingam et al., Cytokine storm in a phase 1 trial of the anti-CD28 monoclonal antibody TGN1412. N Engl J Med. Sep. 7, 2006;355(10):1018-1028.
Tan et al., Acute Myocarditis Following High-Dose Interleukin-2 Treatment. J Cardiol Cases. Jan. 1, 2016;15(1):28-31.
Temann et al., Pulmonary Overexpression of IL-9 Induces Th2 Cytokine Expression, Leading to Immune Pathology. J Clin Invest. Jan. 1, 2002;109(1):29-39.
Temann et al., IL9 Leads to Airway Inflammation by Inducing IL13 Expression in Airway Epithelial Cells. Int Immunol. Jan. 1, 2007;19(1):1-10.
Thiant et al., Plasma Levels of IL-7 and IL-15 in the First Month after Myeloablative BMT Are Predictive Biomarkers of Both Acute GVHD and Relapse. Bone Marrow Trans. Oct. 2010;45(10):1546-1552.
Tisoncik et al., Into the eye of the cytokine storm. Microbiol Mol Biol Rev. Mar. 2012;76(1):16-32.
Tokman et. al., The Pathogenesis of Experimental Toxic Shock Syndrome: The Role of Interleukin-2 in the Induction of Hypotension and Release of Cytokines. Shock Feb. 1, 1995;3(2):145-151.
Tourkova et al., Restoration by IL-15 of MHC Class I Antigen-Processing Machinery in Human Dendritic Cells Inhibited by Tumor-Derived Gangliosides. J Immunol. Sep. 1, 2005;175(5):3045-3052.
Trottestam et. al., Chemoimmunotherapy for Hemophagocytic Lymphohistiocytosis: Long-Term Results of the HLH-94 Treatment Protocol. Blood. Oct. 27, 2011;118(17):4577-4584.
Tsoutsou et al., Cytokine Levels in the Sera of Patients with Idiopathic Pulmonary Fibrosis. Respir Med. May 1, 2006;100(5):938-945.
Uchiyama et al., Study of the Biological Activities of Toxic Shock Syndrome Toxin-1. Proliferative Response and Interleukin 2 Production by T Cells Stimulated with the Toxin. Microbiol Immunol. May 1986;30(5):469-483.
Ueda et al., Serum Interleukin-15 Level Is a Useful Predictor of the Complications and Mortality in Severe Acute Pancreatitis. Surgery. Sep. 1, 2007;142(3):319-326.
Van Den Brûle et al., Profibrotic Effect of IL-9 Overexpression in a Model of Airway Remodeling. Am J Respir Cell Mol Biol. Aug. 2007;37(2):202-209.
Veenhuis et al., Systemic Elevation of Proinflammatory Interleukin 18 in HIV/HCV Coinfection versus HIV or HCV Monoinfection. Clin Infect Dis. Mar. 2017;64(5):589-596.
Via et al. Kinetics of T Cell Activation in Acute and Chronic Forms of Murine Graft-versus-Host Disease. J Immunol. Apr. 15, 1991;146(8):2603-2609.
Via et al., Critical Role of Interleukin-2 in the Development of Acute Graft-versus-Host Disease. Int Immunol. Jun. 1, 1993;5(6):565-572.
Villinger et al., Markedly Elevated Levels of Interferon (IFN)-γ, IFN-α, Interleukin (IL)-2, IL-10, and Tumor Necrosis Factor-αAssociated with Fatal Ebola Virus Infection. J Infect Dis. 1999;179:S188-S191.
Vissinga et al. TCR Expression and Clonality Analysis in Pulmonary Sarcoidosis. Hum Immunol. Jun. 1, 1996;48(1-2):98-106.
Waldmann et al., The Multifaceted Regulation of Interleukin-15 Expression and the Role of this Cytokine in Nk Cell Differentiation and Host Response to Intracellular Pathogens. Annu Rev Immunol. 1999;17:19-49.
Wang et al., Biomarkers of Cytokine Release Syndrome and Neurotoxicity Related to CAR-T Cell Therapy. Biomark Res. Dec. 2018;6(1):4 in 10 pages.
Wang et al., "IL-2 and IL-15 blockade by BNZ-1, an inhibitor of selective [gamma]-chain cytokines, decreases leukemic T-cell viability". Leukemia. May 2019;33(5):1243-1255.
Watanabe et al., Pro-inflammatory and anti-inflammatory T cells in giant cell arteritis. Jt Bone Spine. Jul. 1, 2017;84(4):421-426.
Wauquier et al., Human Fatal Zaire Ebola Virus Infection is Associated with an Aberrant Innate Immunity and with Massive Lymphocyte Apoptosis. PLoS Negl Trop Dis. Oct. 5, 2010;4(10):e837 in 10 pages.
Wei et al., Activation of Tumor Necrosis Factor-Alpha Production from Human Neutrophils by IL-2 via IL-2-Rβ. J Immunol. Mar. 1, 1993;150:1979-1987.
Welbourn et al., Involvement of Thromboxane and Neutrophils in Multiple-System Organ Edema with Interleukin-2. Ann Surg. Dec. 1990;212(6):728-733.
Welbourn et al., Interleukin-2 Induces Early Multisystem Organ Edema Mediated by Neutrophils. Ann Surg. Aug. 1991;214(2):181-186.
Welch et al., Fluorescent Crimean-Congo Hemorrhagic Fever Virus Illuminates Tissue Tropism Patterns and Identifies Early Mononuclear Phagocytic Cell Targets in Ifnar-/- Mice. PLoS Pathog. Dec. 2, 2019;15(12):e1008183 in 23 pages.
Weyand et al., Disease patterns and tissue cytokine profiles in giant cell arteritis. Arthritis Rheum. Jan. 1997;40(1):19-26.
White et al. Cardiopulmonary Toxicity of Treatment with High Dose Interleukin-2 in 199 Consecutive Patients with Metastatic Melanoma or Renal Cell Carcinoma. Cancer. Dec. 15, 1994;74(12):3212-3222.
Williams et al., The Mercurial Nature of Neutrophils: Still an Enigma in ARDS? Am J Physiol Lung Cell Mol Physiol. Feb. 1, 2014;306(3):L217-L230.
Winn et al., Selective Effects of Interleukin (IL)-15 on Antifungal Activity and IL-8 Release by Polymorphonuclear Leukocytes in Response to Hyphae of *Aspergillus* Species. J Infect Dis. Aug. 15, 2003;188(4):585-590.

(56) References Cited

OTHER PUBLICATIONS

Wuttge et al., Serum IL-15 in patients with early systemic sclerosis: a potential novel marker of lung disease. Arthritis Res Ther. Oct. 2007;9(5):1-9.

Xie et al., Inflammatory Markers of the Systemic Capillary Leak Syndrome (Clarkson Disease). J Clin Cell Immunol. 2014;5:1000213 in 15 pages.

Xu et al., IL-9 Blockade Attenuates Inflammation in a Murine Model of Methicillin-Resistant *Staphylococcus aureus* Pneumonia. Acta Biochim Biophys Sin. Feb. 2020;52(2):133-140.

Yang et al., Interleukin-2 and Lymphocyte-Induced Eosinophil Proliferation and Survival in Asthmatic Patients. J Allergy Clin Immunol. Mar. 1, 1993;91(3):792-801.

Yang et al., Epstein-Barr virus (EBV)-encoded RNA promotes growth of EBV-infected T cells through interleukin-9 induction. Cancer Res. Aug. 1, 2004;64(15):5332-5337.

Yang et al., TCR Engagement Negatively Affects CD8 but Not CD4 Car T Cell Expansion and Leukemic Clearance. Sci Transl Med. Nov. 22, 2017;9(417):eaag1209 in 23 pages.

Yarkoni et al., IL-2-targeted therapy ameliorates the severity of graft-versus host disease: Ex vivo selective depletion of host-reactive T cells and in vivo therapy. Biol Blood Marrow Transplant. Apr. 1, 2012;18(4);523-535.

Youinou et al., Disturbance of Cytokine Networks in Sjogren's Syndrome. Arthritis Res Ther. Aug. 2011;13(4):227 in 10 pages.

Younan et al., Ebola Virus Binding to Tim-1 on T Lymphocytes Induces a Cytokine Storm. MBio. Sep. 26, 2017;8(5):00847-17.

Younan et al., Ebola Virus-Mediated T-Lymphocyte Depletion Is the Result of an Abortive Infection. PLoS Pathog. Oct. 24, 2019;15(10):e1008068 in 25 pages.

Yuki et al., COVID-19 pathophysiology: A review. Clin Immunol. Jun. 1, 2020;215:108427 in 7 pages.

Zhang et al., Potent and Selective Stimulation of Memory-Phenotype CD8 T Cells In Vivo by IL-15. Immunity. May 1, 1998;8(5):591-599.

Zhou et al., Th2 cytokines and asthma. Interleukin-9 as a therapeutic target for asthma. Respir Res. Apr. 2001;2(2):80-84.

Zinter et al. Calming the Storm in HLH. Blood Jul. 11, 2019;134:103-104.

Lerkvaleekul et al., Macrophage Activation Syndrome: Early Diagnosis Is Key. Open Access Rheumatol. 2018;10:117-128.

\* cited by examiner

Alignment of the D-helix region sequence of human γc-family cytokines

| SEQ ID NO: | | | | | | | | | | | | | | | | | | | | | | | |
|---|---|---|---|---|---|---|---|---|---|---|---|---|---|---|---|---|---|---|---|---|---|---|---|
| 3 | IL-15 | I | K | E | F | L | Q | S | F | V | H | I | V | Q | M | F | I | N | T | S | stop | | | |
| 4 | IL-2 | I | V | E | F | L | N | R | W | I | T | F | C | Q | S | I | I | S | T | L | T | stop | | |
| 5 | IL-21 | P | K | E | F | L | E | R | F | K | S | L | L | Q | K | M | I | H | Q | H | L | S | | |
| 6 | IL-4 | L | E | N | F | L | E | R | L | K | T | I | M | R | E | K | Y | S | K | C | S | S | | |
| 7 | IL-9 | A | L | T | F | L | E | S | L | L | E | L | F | Q | K | E | K | M | R | G | M | R | | |
| 8 | IL-7 | D | L | C | F | L | K | R | L | - | - | L | - | Q | E | I | K | T | C | W | N | K | I | L |

FIG. 1A

The consensus sequence for the γc- and the IL-2/IL-15-box.

| | | D/E | F | L | Polar E QN | Polar S/R | Non-polar | Non-polar I,K | | Aliphatic L/I | Non-polar | Q | Charged | | I/K | | T | S | SEQ ID NO: |
|---|---|---|---|---|---|---|---|---|---|---|---|---|---|---|---|---|---|---|---|
| γc-Box | | | | | | | | | | | | | | | | | | | 9 |
| IL-2/IL-15 box | | | | | | | | | | | | Q | | | I | | T | S | 10 |
| 1 | 2 | 3 | 4 | 5 | 6 | 7 | 8 | 9 | 10 | 11 | 12 | 13 | 14 | 15 | 16 | 17 | 18 | 19 | |

FIG. 1B

COMPOSITIONS AND METHODS FOR MODULATING γ-C-CYTOKINE ACTIVITY

PRIORITY AND CROSS REFERENCE TO RELATED APPLICATIONS

This application is a Continuation Application of U.S. application Ser. No. 15/474,312, filed Mar. 30, 2017, which is a Continuation Application of U.S. application Ser. No. 14/852,240, filed Sep. 11, 2015, and issued as U.S. Pat. No. 9,675,672 on Jun. 13, 2017, which is a Continuation Application of U.S. application Ser. No. 13/868,725, filed Apr. 23, 2013, and issued as U.S. Pat. No. 9,133,243 on Sep. 15, 2015, which is a Continuation Application of U.S. application Ser. No. 13/589,017, filed Aug. 17, 2012, and issued as U.S. Pat. No. 8,455,449 on Jun. 4, 2013, which is a Continuation Application of International Application No. PCT/US2012/021566, filed Jan. 17, 2012, in the English language, which claims the benefit of U.S. Provisional Patent Application No. 61/433,890, filed Jan. 18, 2011, and U.S. Provisional Patent Application No. 61/527,049, filed Aug. 24, 2011, the contents of each of which are incorporated herein by reference in their entirety. The U.S. application Ser. No. 14/852,240, filed Sep. 11, 2015, is also a Continuation Application of U.S. application Ser. No. 13/980,305, filed Jul. 17, 2013, and issued as U.S. Pat. No. 9,133,244 on Sep. 15, 2015, which is the U.S. National Phase Entry Application under 35 U.S.C. § 371 of International Application No. PCT/US2012/021566, filed Jan. 17, 2012 (supra), the contents of each of which are incorporated herein by reference in their entirety.

SEQUENCE LISTING IN ELECTRONIC FORMAT

The present application is being filed along with an Electronic Sequence Listing as an ASCII text file via EFS-Web. The Electronic Sequence Listing is provided as a file entitled BION001C5SEQLIST.txt, created on Mar. 3, 3019, and last modified on Mar. 6, 2019, which is 6,036 bytes in size. The information in the Electronic Sequence Listing is incorporated herein by reference in its entirety.

BACKGROUND

Field

The present embodiments relate to of design of peptide and/or peptide derivative antagonists of γc-family cytokines, a group of mammalian cytokines that are mainly produced by epithelial, stromal and immune cells and control the normal and pathological activation of a diverse array of lymphocytes. The present embodiments also relate to the therapeutic uses of such of design of peptide and/or peptide derivative antagonists for the treatment of certain human diseases. The present embodiments also relate to the cosmeceutical applications of such of design of peptide and/or peptide derivative antagonists. Description of target diseases, cosmeceutical applications, as well as methods of administration, production, and commercialization of the peptides are disclosed.

Description of the Related Art

Cytokines are a diverse group of soluble factors that mediate various cell functions, such as, growth, functional differentiation, and promotion or prevention of programmed cell death (apoptotic cell death). Cytokines, unlike hormones, are not produced by specialized glandular tissues, but can be produced by a wide variety of cell types, such as epithelial, stromal or immune cells.

SUMMARY

In some embodiments, a method of designing a peptide or peptide derivative to modulate γc-cytokine activity is provided. In some embodiments, the method comprises the steps of obtaining a sequence comprising a partial sequence of a γc-box D-helix region of each of at least two interleukin (IL) proteins, and assembling the peptide or peptide derivative comprising the sequence comprising the partial sequences of the γc-box D-helix regions of the at least two IL proteins, wherein the sequence comprises 11 to 50 amino acids, wherein the peptide or peptide derivative modulates the activity of one or more γc-cytokines.

In some embodiments of the method, the sequence comprises consecutive blocks of 1-5 amino acids of the at least two IL protein γc-box D-helix regions. In some embodiments of the method, the sequence comprises consecutive blocks of 1-10 amino acids of the at least two IL protein γc-box D-helix regions. In some embodiments of the method, the at least two IL protein γc-box D-helix regions are from IL proteins selected from the group consisting of IL-15, IL-2, IL-21, IL-4, IL-9, and IL-7. In some embodiments of the method, the peptide or peptide derivative further comprises a conjugate at the N-termini, C-termini, side residues, or a combination thereof. In some embodiments of the method, the peptide or peptide derivative further comprises a signal peptide.

In some embodiments of the method, the peptide comprises the amino acid sequence D/E-F-L-E/Q/N-S/R-X-I/K-X-L/I-X-Q (SEQ ID NO: 2), wherein X denotes any amino acid. In some embodiments of the method, the peptide derivative shares at least about 50% identity with a peptide of SEQ ID NO: 2. In some embodiments of the method, the peptide derivative shares at least about 90% identity with a peptide of SEQ ID NO: 2. In some embodiments of the method, the peptide derivative shares at least about 95% identity with a peptide of SEQ ID NO: 2. In some embodiments of the method, the peptide and the peptide derivative have similar physico-chemical properties but distinct biological activities.

In some embodiments of the method, the peptide comprises the amino acid sequence I-K-E-F-L-Q-R-F-I-H-I-V-Q-S-I-I-N-T-S (SEQ ID NO: 1) (BNZ-γ). In some embodiments of the method, the peptide derivative shares at least about 50% identity with a peptide of SEQ ID NO: 1. In some embodiments of the method, the peptide derivative shares at least about 90% identity with a peptide of SEQ ID NO: 1. In some embodiments of the method, the peptide derivative shares at least about 95% identity with a peptide of SEQ ID NO: 1. In some embodiments of the method, the peptide and the peptide derivative have similar physico-chemical properties but distinct biological activities. In some embodiments of the method, the peptide or peptide derivative inhibits the activity of one or more γc-cytokines. In some embodiments of the method, the one or more γc-cytokines are selected from the group consisting of IL-2, IL-4, IL-7, IL-9, IL-15 and IL-21. In some embodiments of the method, the peptide or peptide derivative inhibits the activity of IL-2, IL-15 and IL-9. In some embodiments of the method, the peptide or peptide derivative inhibits the activity of IL-15 and IL-9.

In some embodiments of the method, the peptide or peptide derivative is used to ameliorate and/or treat a disease selected from the group consisting of a γc-cytokine-mediated disease, an HTLV-1-associated myelopathy (HAM)/tropical spastic paraparesis (TSP) associated disease, and an inflammatory respiratory disease. In some embodiments of the method, the γc-cytokine-mediated disease is selected from the group consisting of CD4-leukemia, CD8-leukemia, LGL-leukemia, systemic lupus erythematosus, Sjögren's syndrome, Wegener's granulomatosis, Celiac disease, Hashimoto's thyroiditis, rheumatoid arthritis, inflammatory bowel disease, diabetes mellitus, psoriasis, multiple sclerosis, uveitis, inflammation of the eye, and graft-versus-host disease (GvHD). In some embodiments of the method, the HAM/TSP associated disease is selected from the group consisting of Adult T-cell Leukemia (ATL), HTLV-associated Myelopathy/Tropical Spastic Paraparesis (HAM/TSP), and other non-neoplastic inflammatory diseases associated with HTLV. In some embodiments of the method, the inflammatory respiratory disease is selected from the group consisting of asthma, sinusitis, hay fever, bronchitis, chronic obstructive pulmonary disease (COPD), allergic rhinitis, acute and chronic otitis, and lung fibrosis. In some embodiments of the method, the peptide or peptide derivative is used for a cosmetic purpose. In some embodiments of the method, the cosmetic purpose is selected from the group consisting of treatment of acne, treatment of hair loss, treatment of sunburn, nail maintenance, and reduction in the appearance of aging.

BRIEF DESCRIPTION OF THE DRAWINGS

FIG. 1A shows an alignment of the D-helix region of human γc-cytokine family members.

FIG. 1B depicts the γc-box and IL-2/IL-15 box motifs which give rise to the consensus sequence around the D-helix region of the γc-cytokines.

DETAILED DESCRIPTION

Overview

Figure 2:
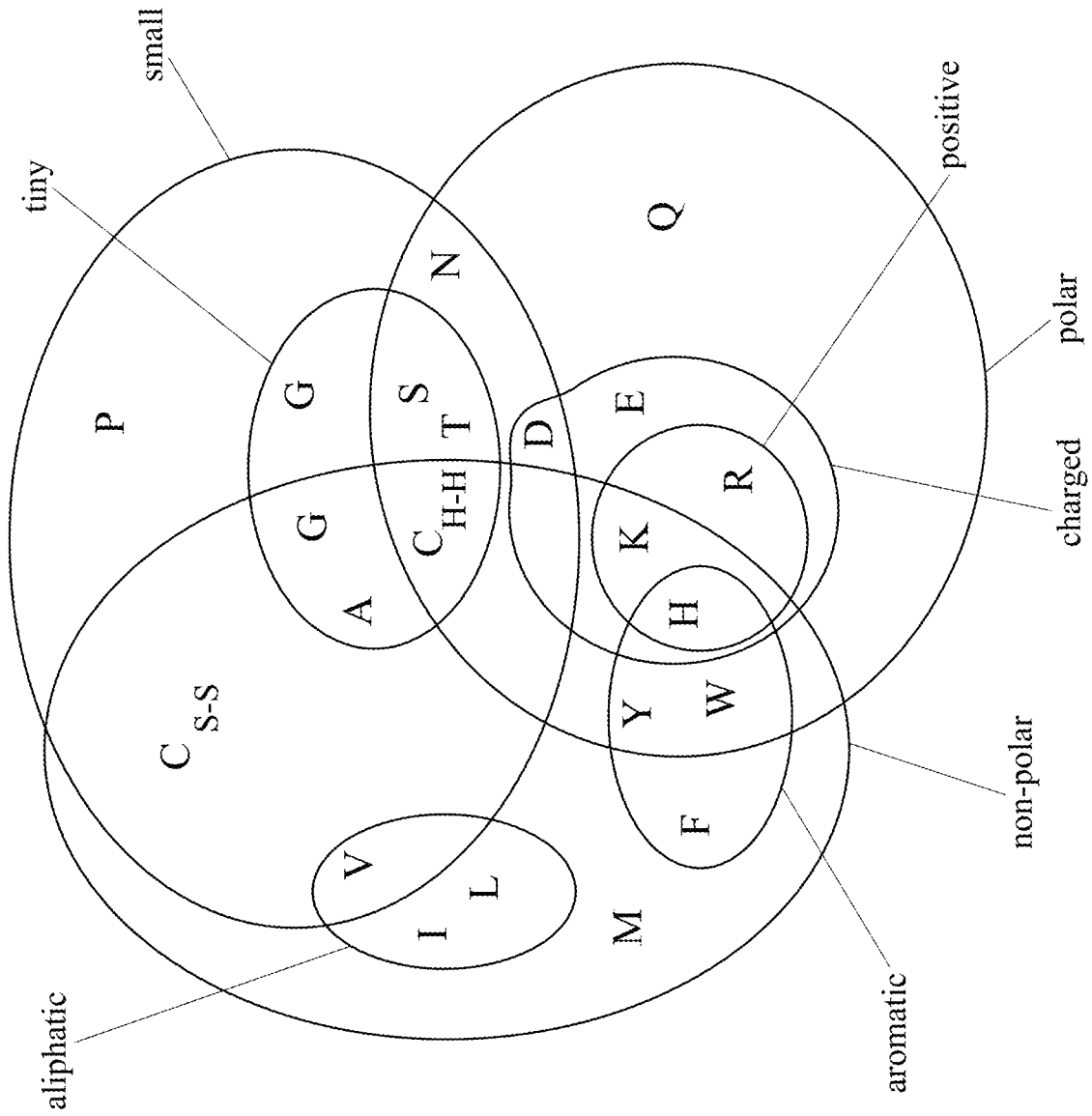
FIG. 2 depicts a diagramed representation of the biochemical properties of amino acids.

More than 100 cytokines have been identified so far and are considered to have developed by means of gene duplications from a pool of primordial genes (See Bazan, J. F. 1990, Immunol. Today 11:350-354). In support of this view, it is common for a group of cytokines to share a component in their multi-subunit receptor system. The most well-documented shared cytokine subunit in T cells is the common γ subunit (γc-subunit).

The γc-subunit is shared by 6 known cytokines (Interleukin-2 (IL-2), Interleukin-4 (IL-4), Interleukin-7 (IL-7), Interleukin-9 (IL-9), Interleukin-15 (IL-15), and Interleukin-21 (IL-21), collectively called the "γc-cytokines" or "γc-family cytokines") and plays an indispensable role in transducing cell activation signals for all these cytokines. Additionally, for each of the γc-cytokines, there are one or two private cytokine-specific receptor subunits that when complexed with the γc-subunit, give rise to a fully functional receptor. (See Rochman et al., 2009, Nat Rev Immunol. 9: 480-90.)

The γc-cytokines are important players in the development of the lymphoid cells that constitute the immune system, particularly T, B, and NK cells. Further, γc-cytokines have been implicated in various human diseases. Thus, factors that inhibit γc-cytokine activity would provide useful tools to elucidate the developmental mechanism of subsets of lymphocytes and to treat immune disorders and γc-cytokine-mediated diseases.

The γc-family cytokines are a group of mammalian cytokines that are mainly produced by epithelial, stromal and immune cells and control the normal and pathological activation of a diverse array of lymphocytes. These cytokines are critically required for the early development of T cells in the thymus as well as their homeostasis in the periphery. For example, in the absence of the γc-subunit, T, B and NK cells do not develop in mice. (See Sugamura et al., 1996, Annu. Rev. Immunol. 14:179-205).

Germ line depletion of the genes encoding the γc-subunit in mice or mutations of γc-subunit in humans are known to cause severe combine immunodeficiency (SCID) by disrupting the normal appearance or function of NK, T, and B cells. The importance of the γc-subunit in the signal transduction of the γc-cytokines, IL-2, -4, -7, -9, 15, -21, is indicated in studies demonstrating the a of response of lymphocytes from these mice and human patients to the γc-cytokines (reviewed in Sugamura et al., 1995 Adv. Immunol. 59:225-277). This indicates that disruption of the interaction between the γc-subunit and a γc-cytokine would efficiently block the intracellular signaling events by the γc-cytokine family members. Therefore antagonist peptides according to the present embodiments are expected to effectively block the pathogenic changes in humans suffering from the diseases mediated by misregulation of the γc-cytokine family members.

As an alternative to antibody-mediated approaches for modulating the activity of individual γc-cytokines, Applicants have devised novel, low molecular weight compounds herein referred to as "Simul-Block", which suppress the activity of multiple γc-cytokines. These low molecular weight compounds, which include both chemicals and peptides, are less immunogenic than antibodies. These properties distinguish Simul-Block as a more efficient strategy for mediating γc-cytokine activity in clinical interventions.

Pathologies Associated with the γc-Cytokines

Recent studies have indicated that dysregulation of expression and dysfunction of the γc-cytokines could lead to a wide variety of human immunologic and hematopoietic diseases.

IL-2

While IL-2 was historically considered a prototype T cell growth factor, the generation of a knockout mouse lacking IL-2 expression revealed that IL-2 is not critical for the growth or developmental of conventional T cells in vivo.

Over-expression of IL-2, however, leads to a preferential expansion of a subset of T-cells; the regulatory T cells (T-regs). (See Antony et al., 2006, J. Immunol. 176:5255-66.) T-regs suppress the immune responses of other cells and thus act to maintain peripheral tolerance (reviewed in Sakaguchi et al., 2008, Cell 133:775-87). Breakdown of peripheral tolerance is thought to cause autoimmune diseases in humans. Thus, the immunosuppressive function of T-regs is thought to prevent the development of autoimmune diseases (See Sakaguchi et al., 2008, Cell 133:775-87). T-regs have also been implicated in cancer, where solid tumors and hematologic malignancies have been associated with elevated numbers of T-regs (See De Rezende et al., 2010, Arch. Immunol. Ther. Exp. 58:179-190).

IL-4

IL-4 is a non-redundant cytokine involved in the differentiation of T helper cells into the Th2 (T-helper type 2) subset, which promotes the differentiation of premature B cells into IgE producing plasma cells. IgE levels are elevated in allergic asthma. Thus, IL-4 is implicated in the development of allergic Asthma. Antibodies targeting IL-4 can be used to treat or even prevent the onset of allergic asthma. (See Le Buanec et al., 2007, Vaccine 25:7206-16.)

IL-7

IL-7 is essential for B cell development and the early development of T cells in the thymus. In mice, the abnormal expression of IL-7 causes T-cell-associated leukemia. (See Fisher et al., 1993, Leukemia 2:S66-68.) However, in humans, misregulation of IL-7 does not appear to cause T-cell-associated leukemia. In humans, up-regulation of IL-7 either alone or in combination with another γc-cytokine family member, IL-15, has been implicated in Large Granular Lymphocyte (LGL) leukemia.

IL-9

The role of IL-9 is still rather uncharacterized compared to other γc-cytokine family members. Mice depleted of the IL-9 gene appear normal and do not lack any subsets of cells in the lymphoid and hematopoietic compartments. Recent studies, however, reveal an in vivo role for IL-9 in the generation of Th17 (T-helper induced by interleukin-17) cells (See Littman et al., 2010, Cell 140(6):845-58; and Nowak et al., 2009, J. Exp. Med. 206: 1653-60).

IL-15

IL-15 is critically involved in the development of NK cells, NK-T cells, some subsets of intraepithelial lymphocytes (IELs), γδ-T cells, and memory-phenotype CD8 T-cells (See Waldmann, 2007, J. Clin. Immunol. 27:1-18; and Tagaya et al., 1996, EMBO J. 15:4928-39.) Overexpression of IL-15 in mice leads to the development of NK-T cell and CD8 cell type T cell leukemia (See Fehniger et al., 2001, J. Exp. Med. 193:219-31; Sato et al. 2011 Blood in press). These experimentally induced leukemias appear similar to LGL (large-granular lymphocyte) leukemia in humans, since in both instances the leukemic cells express CD8 antigen.

It is also suspected that IL-15-mediated autocrine mechanisms may be involved in the leukemic transformation of CD4 T lymphocytes. (See Azimi et al., 1998, Proc. Natl. Acad. Sci. 95:2452-7; Azimi et al., 1999, J. Immunol. 163:4064-72; Azimi et al., 2000, AIDS Res. Hum. Retroviruses 16:1717-22; and Azimi et al., 2001, Proc. Natl. Acad. Sci. 98:14559-64). For example, CD4-tropic HTLV-I, which causes Adult T cell leukemia in humans, induces autocrine growth of virus-transformed T cells through the production of IL-15 and IL-15Rα (Azimi et al., 1998, Proc. Natl. Acad. Sci. 95:2452-7).

In addition to leukemic transformation, recent studies implicate IL-15 in the pathological development of Celiac disease (CD), an autoimmune disease. IL-15 is known to stimulate the differentiation of NK, CD8 and intestinal intraepithelial lymphocyte (IEL) cells into lymphokine-activated killer (LAK) cells by inducing the expression of cytolytic enzymes (i.e., Granzyme and Perforin) as well as interferon-γ. Celiac Disease (denoted CD from herein) is an immune-mediated enteropathy that is triggered by the consumption of gluten-containing food in individuals that express specific HLA-DQ alleles. The prevalence of this disease is 1% in the western population. The only current treatment for CD is the complete elimination of gluten from the patient's diet. The pathology of CD is mainly caused by extensive damage to the intestinal mucosa, which is caused by activated CD8 T cells that have infiltrated to the intestinal lamina propria. These CD8 T cells appear to be activated through mechanisms involving IL-15. One recent publication demonstrated in mice that ectopic over-expression of IL-15 by enterocytes leads to the development of enteropathy, which closely resembles the lesions in CD patients. Neutralization of IL-15 activity dramatically diminished the pathological changes. Thus, an intervention blocking the activation of CD8 T cells by IL-15 appears to provide an alternative strategy in managing CD to the conventional gluten-free diet.

IL-21

IL-21 is the most recently discovered member of the γc-family. Unlike other family members, IL-21 does not appear to have potent growth-promoting effects. Instead, IL-21 is thought to function more as a differentiation factor than a factor controlling cellular proliferation (See Tagaya, 2010, J. Leuk. Biol. 87:13-15).

Current Strategies for Treating γc-Cytokine-Mediated Disorders

Because the γc-cytokines are thought to be involved in numerous human diseases, several methods of treating γc-cytokine-implicated diseases by inhibiting γc-cytokine family activities have been proposed. These methods include the use of cytokine-specific monoclonal antibodies to neutralize the targeted cytokine's activity in vivo; use of monoclonal antibodies targeting the private cytokine-specific receptor subunits (subunits other than the shared γc-subunit) to selectively inhibit cytokine activity; and use of chemical inhibitors that block the downstream intracellular cytokine signal transduction pathway. While cytokine-specific antibodies are often the first choice in designing therapeutics, cytokines that share receptor components display overlapping functions (See Paul, W. E., 1989, Cell 57:521-24) and more than one cytokine can co-operate to cause a disease (See Examples described below). Thus, approaches involving neutralization of a single cytokine may not be effective in the treatment of cytokine-implicated human diseases.

Strategies for designing therapeutics that inhibit the function of multiple cytokines via antibodies which recognize a shared receptor component have also been proposed. However, the multi-subunit nature of cytokine receptor systems and the fact that functional receptors for a single cytokine can assume different configurations makes this approach difficult. For example, a functional IL-15 receptor can be either IL-15Rβ/γc or IL-15Rα/β/γc. (See Dubois et al., 2002, Immunity 17:537-47.) An antibody against the IL-15Rβ receptor (TMβ1), is an efficient inhibitor of the IL-15 function, but only when the IL-15Rα molecule is absent from the receptor complex. (See Tanaka et al., 1991, J. Immunol. 147:2222-28.) Thus, the effectiveness of a monoclonal anti-receptor antibody, whether raised against a shared or a private subunit, can be context-dependent and is unpredictable in vivo.

Although clinical use of monoclonal antibodies against biologically active factors or receptors associated with the pathogenesis of diseases is an established practice, there are few demonstrations of successful outcomes. Moreover, establishment of a clinically-suited monoclonal antibody treatment is a long and difficult process, with the successful generation of a neutralizing antibody largely a matter of luck. For example, due to the critical importance of the γc-subunit in mediating signaling by γc-family cytokines, many attempts to generate polyclonal and monoclonal antibodies against the γc-subunit have been made and there exist many commercial antibodies recognizing the γc-subunit in mice and in humans. Curiously, however, none of these anti-γc-subunit antibodies block the function of the γc-cytokines.

Another problem with the therapeutic use of monoclonal antibodies is that monoclonal antibodies are usually generated by immunizing rodents with human proteins, so the generated antibody is a foreign protein and thus highly immunogenic. To circumvent this problem, the amino acid sequence of the monoclonal antibody is molecularly modified so that the antibody molecule is recognized as a human immunoglobulin (a process called humanization), but this process requires time and expense.

Targeting JAK3, as an Existing Alternative Example for the Inhibition of Multiple γc-Cytokines The interaction between the γc-subunit and a γc-cytokine leads to the activation of an intracellular protein tyrosine kinase called Janus kinase 3 (Jak3). Jak3, in turn, phosphorylates multiple signaling molecules including STAT5, and PI3 kinase. The interaction of the γc-subunit and Jak3 is very specific. In fact, there is no other receptor molecule that recruits Jak3 for signal transduction. (See O'Shea, 2004, Ann. Rheum. Dis. 63:(suppl. II):ii67-7.) Thus, the inhibition of cytokine signaling through the γc-subunit can be accomplished by blocking the activity of Jak3 kinase. Accordingly, multiple chemical inhibitors that target the kinase activity of Jak3 have been introduced to the market. (See Pesu et al., 2008, Immunol. Rev. 223:132-142.) One such example is CP690,550.

The major shortcoming of these protein kinase inhibitors is the lack of specificity to Jak3 kinase. These drugs intercept the binding of ATP (adenosine-triphosphate) molecules to Jak3 kinase, a common biochemical reaction for many protein kinases, and thus tend to block the action of multiple intracellular protein kinases that are unrelated to Jak3 kinase whose actions are critically needed for the well-being of normal cells in various tissues. Thus, more specific inhibitors of signaling through the γc-subunit are needed.

There is therefore a great need for an alternative strategy for treating γc-cytokine-implicated diseases.

Discovery of the γc-Box

The C-terminus (the D-helix) of the γc-cytokines contains the proposed site for interacting with the common γc-subunit of the multi-unit cytokine receptors. (Bernard et al., 2004 J. Biol. Chem. 279:24313-21.) Comparison of the biochemical properties of the amino acids of all γc-cytokines identified in mice and humans revealed that the chemical nature of the amino acids, for example, hydrophobicity, hydrophilicity, base/acidic nature, are conserved, if not identical, at many positions in the D-helix across the members of the γc-cytokine family. In contrast, the sequence of IL-13, which is related to the γc-cytokine, IL-4, but does not bind to the γc-subunit, does not exhibit significant homology in the D-helix region to the γc-cytokines, suggesting that the sequence homology in the D-helix region is correlated with binding to the γc-subunit. As shown in FIG. 1, alignment of the amino acid sequences of the D-helix region of γc-cytokine family members in humans reveals a motif of moderate sequence homology in these cytokines referred to herein as "the γc-box".

The γc-box comprises 19 amino acids where out of the 19 positions, positions 4, 5, and 13 are fully conserved as Phenylalanine, Leucine, and Glutamine, respectively. Less conservation is observed at positions 6, 7 and 11 of the γc-box where the amino acid is one of two or three related amino acids that share physico-chemical properties: position 6 may be occupied by the polar amino acids Glutamate, Asparagine or Glutamine; non-polar amino acids Serine or Arginine can occupy position 7; and position 11 is occupied by either of the non-polar aliphatic amino acids Leucine or Isoleucine. Positions 9 and 16 may be occupied by the either the non-polar amino acid Isoleucine or the polar amino acid Lysine. See FIG. 1B. Some differences in the amino acid composition of the γc-box are observed at positions 9 and 16 amongst subfamilies of the γc-cytokines. Comparison of the γc-cytokines across species indicates that Isoleucine is often present at the 9 and 16 positions in the IL-2/15 subfamily, whereas the other γc-family members often possess Lysine in these positions. Not wishing to be bound by a particular theory, Isoleucine and Lysine are biochemically different and thus may impart specific conformational differences between the IL-2/15 subfamily and other γc-cytokines.

Conservation of the γc-box motif between γc-cytokines is supported by findings that an Glutamine (Gln, Q) residue located in the D-helix region is critical for the binding of the γc-cytokines to the γc-subunit. (Bernard et al., 2004 J. Biol. Chem. 279: 24313-21.)

Peptide Inhibitors of γc-Cytokine Activity

The activity of γc-family cytokines may be blocked by disrupting the interaction between the γc-cytokine and the γc-subunit, for example by introducing a competitive inhibitor which can interact with the γc-subunit without stimulating signaling through the multi-subunit cytokine receptors. Not to be bound by a particular theory, the conserved γc-box motif, which participates in binding of the γc-family cytokines to the γc-subunit, presents a core base amino acid sequence which can be utilized to design peptide inhibitors of γc-cytokine signaling.

The core γc-box amino acid sequence comprises: D/E-F-L-E/Q/N-S/R-X-I/K-X-L/I-X-Q (SEQ ID NO: 2) (where X denotes any amino acid). Embodiments described herein relate to custom peptide derivatives of the core γc-box amino acid sequence which can inhibit the activity of one or more γc-cytokines. Custom peptide derivatives include any peptide whose partial amino acid sequence shows approximately 50%, 50-60%, 60-70%, 70-80%, 80%, 90%, 95%, 97%, 98%, 99% or 99.8% identity to the core γc-box amino acid sequence. Custom peptide derivatives further include any peptide wherein a partial amino acid sequence of that peptide derivative comprises amino acids with similar physico-chemical properties to the amino acids of the core γc-box. For example, amino acids with similar physico-chemical properties would include Phenylalanine, Tyrosine, Tryptophan, and Histidine, which are aromatic amino acids. FIG. 2 shows a diagrammed representation of amino acids with similar physico-chemical properties which may be may be substituted for the amino acids comprising the core γc-box. Peptide derivatives of the core γc-box may be 11, 12, 13, 14, 15, 16, 17, 18, 19, 20, 21, 22, 24, 25-30, 30-35, 35-40, 40-45, 45-50, or more than 50 amino acids in length.

In some embodiments, the custom peptide derivatives may be conjugated to the N-termini, C-termini and/or to the side residues of existing biological proteins/peptides.

Based on the identification of the conserved γc-box motif in cytokines which bind to the γc-subunit, Applicants have devised a novel, 19-mer custom derivative peptide which is an artificial composite peptide combining the amino acid sequence of the human IL-2 and IL-15 γc-box. The 19-mer peptide, herein referred to as BNZ-γ, consists of the amino acid sequence: I-K-E-F-L-Q-R-F-I-H-I-V-Q-S-I-I-N-T-S (SEQ ID NO: 1), where the amino acids depicted by bold characters are conserved between IL-2 and IL-15 and the underlined amino acids represent positions where the physico-chemical properties of the amino acids are conserved.

Applicants discovered that the 19-mer BNZ-γ, suppresses IL-15 and IL-9 induced cellular proliferation, but not IL-3 or IL-4 induced cellular proliferation. See FIG. 3A and EXAMPLE 2. Applicants further demonstrated that BNZ-γ inhibits IL-15 mediated phosphorylation of the intracellular cytokine signal transduction molecule, STAT-5. See FIG. 3C and EXAMPLE 5. These results demonstrate that custom peptide derivatives of the conserved γc-box motif can inhibit the activity of multiple γc-cytokines.

Several embodiments relate to custom derivative peptides of the 19-mer BNZ-γ amino acid sequence, I-K-E-F-L-Q-R-F-I-H-I-V-Q-S-I-I-N-T-S (SEQ ID NO: 1), which can inhibit the activity of one or more γc-cytokines. Custom peptide derivatives of the 19-mer BNZ-γ amino acid sequence include any peptide whose partial amino acid sequence shows approximately 50%, 50-60%, 60-70%, 70-80%, 80%, 90%, 95%, 97%, 98%, 99% or 99.8% identity to amino acid sequence: I-K-E-F-L-Q-R-F-I-H-I-V-Q-S-I-I-N-T-S (SEQ ID NO: 1). Custom peptide derivatives further include any peptide wherein a partial amino acid sequence of that peptide derivative comprises amino acids with similar physico-chemical properties to the amino acids of sequence: I-K-E-F-L-Q-R-F-I-H-I-V-Q-S-I-I-N-T-S (SEQ ID NO: 1). In several embodiments, the amino acid residues of the custom derivative peptides retain similar physico-chemical properties with the amino acid residues of BNZ-γ, but exhibit different biological inhibition specificity to the 6 γc-cytokine family members from that of the original 19-mer peptide. Peptide derivatives of BNZ-γ may be 19, 20, 21, 22, 24, 25-30, 30-35, 35-40, 40-45, 45-50, or more than 50 amino acids in length. In some embodiments, the custom peptide derivatives may be conjugated to the N-termini, C-termini and/or to the side residues of existing biological proteins/peptides.

Several embodiments relate to custom peptide derivatives of the γc-box motifs of IL-15, IL-2, IL-21, IL-4, IL-9, or IL-7, which are depicted in FIG. 1A. Other embodiments relate to custom derivative peptides which are artificial composite peptides combining the amino acid sequence of two or more of the human IL-15, IL-2, IL-21, IL-4, IL-9, and IL-7 γc-box motifs. Several embodiments relate to custom peptide derivatives of the of the γc-box motifs of IL-15, IL-2, IL-21, IL-4, IL-9, or IL-7 having a partial amino acid sequence that shows approximately 50%, 50-60%, 60-70%, 70-80%, 80%, 90%, 95%, 97%, 98%, 99% or 99.8% identity to amino acid sequences of the of the γc-box motifs of IL-15, IL-2, IL-21, IL-4, IL-9, or IL-7. Custom peptide derivatives of the of the γc-box motifs of IL-15, IL-2, IL-21, IL-4, IL-9, or IL-7 further include any peptide wherein a partial amino acid sequence of that peptide derivative comprises amino acids with similar physico-chemical properties to the amino acids of sequence of the γc-box motifs of IL-15, IL-2, IL-21, IL-4, IL-9, or IL-7.

Several embodiments relate to custom peptide derivatives that would inhibit the function of one, all, or selective members of the γc-cytokines. In some embodiments, the custom peptide derivatives selectively target individual γc-cytokine family members. For example, a custom peptide derivative can selectively inhibit the function of IL-2, IL-4, IL-7, IL-9, IL-15, or IL-21. In other embodiments, a custom peptide derivative can inhibit 2 or more γc-cytokine family members. For example, the custom peptide derivatives of the present embodiments can selectively inhibit the function of IL-2 in combination with one or more of IL-4, IL-7, IL-9, IL-15, and IL-21; IL-4 in combination with one or more of IL-7, IL-9, IL-15, and IL-21; IL-7 in combination with one or more of IL-9, IL-15, and IL-21; IL-9 in combination with one or more of IL-2, IL-4, IL-7, IL-15, and IL-21; IL-15 in combination with one or more of IL-2, IL-4, IL-7, IL-9, and IL-21; or IL-21 in combination with one or more of IL-2, IL-4, IL-7, IL-9, and IL-15. In other embodiments, custom peptide derivatives can comprehensively target all γc-cytokine family members. Not wishing to be bound by a particular theory, the custom peptide derivatives can inhibit the function of all or selective members of the γc-cytokines by diminishing the binding of γc-cytokines to the γc-subunit, for example, as a competitive inhibitor. Such custom peptide derivatives may be used in diverse applications, including as a clinical drug.

The terms "oligopeptide," "polypeptide," "peptide," and "protein" can be used interchangeably when referring to the custom peptide derivatives provided in accordance with the present embodiments and can be used to designate a series of amino acid residues of any length. Peptides according to the present embodiments may also contain non-natural amino acids. Linker elements can be joined to the peptides of the present embodiments through peptide bonds or via chemical bonds. The peptides of the present embodiments may be linear or cyclic, and may include (D) as well as (L) amino acids. Peptides of the present embodiments may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylamino), with or without any of a wide variety of side chain modifications and/or substitutions (e.g., methylation, benzylation, t-butylation, tosylation, alkoxycarbonylamino, and the like). Residues other than common amino acids that may be present include, but are not limited to, penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid, and diaminopropionic acid.

Peptides of the present embodiments can be produced and obtained by various methods known to those skilled in the art. For example, the peptide may be produced by genetic engineering, based on the nucleotide sequence coding for the peptide of the present embodiments, or chemically synthesized by means of peptide solid-phase synthesis and the like, or produced and obtained in their combination. One skilled in the art can synthesize the custom peptide derivatives based on the present disclosure of the conserved γc-box motif and knowledge of the biochemical properties of amino acids as described in FIG. 2. Some embodiments also relate to polynucleotides comprising nucleotide sequences encoding the peptides of the present invention. "Nucleotide sequence," "polynucleotide," or "nucleic acid" can be used interchangeably, and are understood to mean either double-stranded DNA, a single-stranded DNA or products of transcription of the said DNAs (e.g., RNA molecules). Polynucleotides can be administered to cells or subjects and expressed by the cells or subjects, rather than administering the peptides themselves. Several embodiments also relate to genetic constructs comprising a polynucleotide sequence encoding the peptides of the present invention. Genetic constructs can also contain additional regulatory elements such as promoters and enhancers and, optionally, selectable markers.

Methods of Treating γc-Cytokine Mediated Diseases

Several embodiments relate to the use of γc-antagonist peptides in the treatment of γc-cytokine mediated diseases. Use of custom peptide derivative according to the present embodiments allows for flexibility in the design of the therapeutic agent (custom design of the peptide) and enables more comprehensive outcomes, which would not be accomplished by conventional strategies employing anti-cytokine or anti-cytokine receptor antibodies.

Described herein is a novel method of blocking the action of γc-family cytokines. Such manipulations can yield effective methods of clinical interventions in treating diseases related to the dysregulation or dysfunction of γc-cytokines. Examples of disease that may be treated by disrupting the interaction between the γc-cytokine and the γc-subunit include autoimmune diseases such as systemic lupus erythematosus, Sjögren's syndrome, Wegener's granulomatosis Celiac disease, Hashimoto's or auto-immune thyroiditis; collagen diseases including rheumatoid arthritis, inflammatory bowel disease, diabetes mellitus, autoimmune diseases of the skin such as psoriasis; degenerative neuronal diseases such as multiple sclerosis, uveitis or inflammation of the eye and sympathetic ophthalmia, graft-versus-host disease (GvHD) and myasthenia gravis.

In some embodiments, the γc-antagonist peptides described herein may be used in the treatment of 1-Human T-cell Lymphotropic type I and II (HTLV-I and HTLV-II)-associated diseases including Adult T-cell Leukemia (ATL), HTLV-associated Myelopathy/Tropical Spastic Paraparesis (HAM/TSP), and other non-neoplastic inflammatory diseases associated with HTLV such as uveitis (HU), arthropathy, pneumopathy, dermatitis, exocrinopathy and myositis. In some embodiments, the γc-antagonist peptides described herein may be used in the treatment of other viral diseases such as influenza, AIDS, HBV and Herpes or parasitic diseases.

In several embodiments, the γc-antagonist peptides may be administered before, during, and or after transplantation of various organs as an immunosuppressant agent.

In some embodiments, the γc-antagonist peptides described herein may be used in the treatment of immune-mediated diseases such as asthma and other inflammatory respiratory diseases, such as, but not limited to sinusitis, hay fever, bronchitis, chronic obstructive pulmonary disease (COPD), allergic rhinitis, acute and chronic otitis, lung fibrosis. In some embodiments, γc-antagonist peptides may be administered to treat or prevent allergic reactions due to exposure to allergens, chemical agents or other common causes of acute respiratory disease. In some embodiments, γc-antagonist peptides may be administered to treat or prevent inflammatory responses caused by viruses, bacteria, chemical reagents, and biochemical reagents.

In several embodiments, the γc-antagonist peptides may be administered to treat some types of malignancies such as LGL-leukemia, Intraepithelial lymphoma and leukemia in Refractory Celiac Disease, NK leukemia/lymphoma and NK-T leukemia/lymphoma In some embodiments, custom peptide derivatives according to the embodiments described herein can be used for cosmetic purposes, such as the treatment of acne, hair loss, sunburn and nail maintenance, included to ointment as anti-aging component because of the anti-inflammatory nature of them.

Several embodiments relate to therapeutic antagonist peptides that would inhibit the function of all or selective members of the γc-cytokines. In some embodiments, therapeutic antagonist peptides selectively inhibit individual γc-cytokine family members (custom peptides). In other embodiments, therapeutic antagonist peptides can comprehensively inhibit all γc-cytokine family members (SimulBlock). In some embodiments, therapeutic antagonist peptides selectively inhibit subsets of the γc-cytokines. Not wishing to be bound by a particular theory, the peptide antagonists can inhibit the function of all or selective members of the γc-cytokines by diminishing the binding of γc-cytokines to the γc-subunit, for example, as a competitive inhibitor.

Several members of the γc-cytokine family, IL-2, IL-7, and IL-15, but not IL-4 have been implicated as being involved in graft versus host disease (GvHD) in an experimental mouse model. (Miyagawa et al., 2008 J. Immunol. 181:1109-19.) One embodiment relates to the use of therapeutic antagonist peptides that selectively inhibit IL-2, IL-7, and IL-15 activity for the treatment of GvHD in humans, allowing survival of the grafted tissues or bone marrow cells. Other embodiments relate to the use of therapeutic antagonist peptides that selectively inhibit a combination of IL-2 and IL-7, IL-2, and IL-15, or IL-7 and IL-15 to treat GvHD. Other embodiments relate to the use of a combination of therapeutic antagonist peptides that selectively inhibit IL-2, IL-7, or IL-15.

Some embodiments relate to the use of therapeutic antagonist peptides that selectively inhibit IL-2 function for the treatment of autoimmune disorders where T-regs have been implicated as playing a role. In some embodiments, peptide-mediated inhibition of T-regs can enhance the natural anti-cancer immunity in humans, providing a novel means of anti-cancer therapy.

Several embodiments relate to the use of therapeutic antagonist peptides that selectively inhibit IL-4 to treat asthma.

Some embodiments relate to the use of therapeutic antagonist peptides that selectively inhibit IL-7 either alone or in combination with therapeutic antagonist peptides that selectively inhibit the γc-cytokine family member, IL-15, as a therapeutic agent for LGL leukemia. In some embodiments therapeutic antagonist peptides that selectively inhibit both IL-7 and IL-15 activity can be used to treat LGL leukemia. Several embodiments relate to the use of BNZ-γ to treat LGL leukemia. In some embodiments, specific γc-antagonist peptides that selectively IL-15 alone or specific γc-antagonist peptides that selectively IL-15 and IL-7 are used as a therapeutic agent for CD4/CD8 T lymphocyte-associated leukemia including that caused by the HTLV-I.

Several embodiments relate to the use of γc-antagonist peptides that selectively inhibit the activity of IL-9, either alone or in combination with the other γc-cytokine family members, as a therapeutic agent for human diseases that involve the abnormal development of Th17 cells.

Several embodiments relate to the use of therapeutic antagonist peptides that selectively inhibit IL-15 activity as a therapeutic agent for treating CD. One recent publication suggested that IL-21, in addition to IL-15, may play a role in CD pathogenesis. (See Bodd et al., 2010, Mucosal Immunol. 3:594-601.) This suggests that optimum treatment of CD by conventional anti-cytokine or cytokine-receptor antibodies would benefit from a combination of at least two antibodies recognizing component that belong to the IL-15 and IL-21 systems. In some embodiments, custom derivative antagonist peptides that selectively inhibit both IL-15 and IL-21 activity are used as a therapeutic agent for treating CD.

In addition to having therapeutic applications, γc-antagonist peptides have applications in consumer products as well. Several embodiments relate to the use of γc-antagonist peptides in skin care products such as anti-aging, anti-inflammatory, anti-acne, and other related applications. Some embodiments relate to the use of γc-antagonist peptides in hair products as anti-hair loss ingredient to treat hair loss caused by autoimmune disorders.

Another embodiment relates to the development of chemical compounds (non-peptide, non-protein) that have a spatial structure which resembles the 19-mer amino acid sequence I-K-E-F-L-Q-R-F-I-H-I-V-Q-S-I-I-N-T-S (SEQ ID NO: 1) and can fit into the pocket of the γc-subunit to structurally hinder the access of a γc-cytokine to the γc-subunit for binding. Some embodiments relate to the use of structurally similar chemical compounds as inhibitors of γc-cytokine activity. Such molecular mimicry strategy to further refine the development of synthetic compounds resembling in structure to existing biological peptide/proteins is described in Orzaez et al., 2009 Chem. Med. Chem. 4:146-160. Another embodiment relates to administration of chemical compounds (non-peptide, non-protein) that have a resembling 3D structure as the 19-mer amino acids sequence I-K-E-F-L-Q-R-F-I-H-I-V-Q-S-I-I-N-T-S (SEQ ID NO: 1) to treat γc-cytokine-mediated diseases.

Several embodiments relates to the administration of a peptide of amino acid sequence I-K-E-F-L-Q-R-F-I-H-I-V-Q-S-I-I-N-T-S (SEQ ID NO: 1) to treat γc-cytokine-mediated diseases. Another embodiment relates to the administration of derivative peptides of amino acid sequence I-K-E-F-L-Q-R-F-I-H-I-V-Q-S-I-I-N-T-S (SEQ ID NO: 1), wherein the amino acid sequence of the derivative peptide has similar physico-chemical properties as a peptide of the amino acid sequence I-K-E-F-L-Q-R-F-I-H-I-V-Q-S-I-I-N-T-S (SEQ ID NO: 1), but has distinct biological activity, to treat γc-cytokine-mediated diseases. Another embodiment relates to administration of a peptide of amino acid sequence I-K-E-F-L-Q-R-F-I-H-I-V-Q-S-I-I-N-T-S (SEQ ID NO: 1) conjugated to the N- and C-termini or to the side residues of existing biological proteins/peptides into patients to treat γc-cytokine-mediated diseases.

Several embodiments relate to administration of polyclonal and monoclonal antibodies raised against a peptide comprising of amino acid sequence I-K-E-F-L-Q-R-F-I-H-I-V-Q-S-I-I-N-T-S (SEQ ID NO: 1) into patients as an immunogen to treat γc-cytokine-mediated diseases. Another embodiment relates to administration of polyclonal and monoclonal antibodies that were raised against derivative peptides of amino acid sequence I-K-E-F-L-Q-R-F-I-H-I-V-Q-S-I-I-N-T-S (SEQ ID NO: 1) wherein the amino acid sequence of the derivative peptide has similar physico-chemical properties as a peptide of the amino acid sequence I-K-E-F-L-Q-R-F-I-H-I-V-Q-S-I-I-N-T-S (SEQ ID NO: 1), but has distinct biological activity, into patients as an immunogen to treat γc-cytokine-mediated diseases.

Administration of γc-Antagonist Peptides

The present embodiments also encompass the use of γc-antagonist peptides for the manufacture of a medicament for the treatment of a disease. The present embodiments also encompass a pharmaceutical composition that includes γc-antagonist peptides in combination with a pharmaceutically acceptable carrier. The pharmaceutical composition can include a pharmaceutically acceptable carrier and a non-toxic therapeutically effective amount of γc-antagonist peptides, or other compositions of the present embodiments.

The present embodiments provide methods of using pharmaceutical compositions comprising an effective amount of antagonists for γc-cytokines in a suitable diluent or carrier. A γc-antagonist of the present embodiments can be formulated according to known methods used to prepare pharmaceutically useful compositions. A γc-antagonist can be combined in admixture, either as the sole active material or with other known active materials, with pharmaceutically suitable diluents (e.g., phosphate, acetate, Tris-HCl), preservatives (e.g., thimerosal, benzyl alcohol, parabens), emulsifying compounds, solubilizers, adjuvants, and/or carriers such as bovine serum albumin. Suitable carriers and their formulations are described in Remington's Pharmaceutical Sciences, 16$^{th}$ ed. 1980 Mack Publishing CO. Additionally, such compositions can contain a γc-antagonist complexed with polyethylene glycol (PEG), metal ions, or incorporated into polymeric compounds such as polyacetic acid, polyglycolic acid, hydrogels etc., or incorporated into liposomes, microemulsions, micelles, unilamellar or multilamellar vesicles, erythrocyte ghosts, or spheroblasts. Such compositions will influence the physical state, solubility, stability, rate of in vivo release, and rate of in vivo clearance or a γc-antagonist. A γc-antagonist can be conjugated to antibodies against cell-specific antigens, receptors, ligands, or coupled to ligands for tissue-specific receptors.

Methods of administrating γc-antagonists of the present embodiments may be selected as appropriate, depending on factors, such as the type of diseases, the condition of subjects, and/or the site to be targeted. The γc-antagonists can be administered topically, orally, parenterally, rectally, or by inhalation. The term "parenteral" includes subcutaneous injections, intravenous, intramuscular, intraperitoneal, intracisternal injection, or infusion techniques. These compositions will typically include an effective amount of a γc-antagonist, alone or in combination with an effective amount of any other active material. The amount of the peptide contained in pharmaceutical compositions of the present embodiments, dosage form of the pharmaceutical compositions, frequency of administration, and the like may be selected as appropriate, depending on factors, such as the type of diseases, the condition of subjects, and/or the site to be targeted. Such dosages and desired drug concentrations contained in the compositions may vary affected by many parameters, including the intended use, patient's body weight and age, and the route of administration. Pilot studies will first be conducted using animal studies and the scaling to human administration will be performed according to art-accepted practice.

In one embodiment, host cells that have been genetically modified with a polynucleotide encoding at least one γc-antagonist peptide are administered to a subject to treat a proliferation disorder and/or to reduce the growth of malignant cells. The polynucleotide is expressed by the host cells, thereby producing the peptides within the subject. Preferably, the host cells are allogeneic or autogeneic to the subject.

In a further aspect, γc-antagonist peptides can be used in combination with other therapies, for example, therapies inhibiting cancer cell proliferation and growth. The phrase "combination therapy" embraces the administration of γc-antagonist peptides and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected).

A combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by an appropriate route including, but not limited to, oral routes, intravenous routes, intramuscular routes, and direct absorption through mucous membrane tissues. There therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporarily removed from the administration of the therapeutic agents, perhaps by days or even weeks.

In certain embodiments, γc-antagonist peptides can be administered in combination with at least one anti-proliferative agent selected from the group consisting of chemotherapeutic agent, an antimetabolite, and antitumorgenic agent, and antimitotic agent, and antiviral agent, and antineoplastic agent, an immunotherapeutic agent, and a radiotherapeutic agent.

In certain embodiments, γc-antagonist peptides can be administered in combination with at least one anti-inflammatory agent selected from the group consisting of steroids, corticosteroids, and nonsteroidal anti-inflammatory drugs.

Also provided are kits for performing any of the above methods. Kits may include a γc-antagonist according to the present embodiments. In some embodiments, the kit may include instructions. Instructions may be in written or pictograph form, or may be on recorded media including audio tape, audio CD, video tape, DVD, CD-ROM, or the like. The kits may comprise packaging.

Definitions

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer, and primates. The most preferred animal is human.

As used herein, the term "treat" or any variation thereof (e.g., treatment, treating, etc.), refers to any treatment of a patient diagnosed with a biological condition, such as CD4-, CD8-, and LGL-leukemia, an autoimmune disease, systemic lupus erythematosus, Sjögren's syndrome, Wegener's granulomatosis, Celiac disease, Hashimoto's thyroiditis, a collagen disease, rheumatoid arthritis, inflammatory bowel disease, diabetes mellitus, psoriasis, a degenerative neuronal disease, multiple sclerosis, uveitis, inflammation of the eye, graft-versus-host disease (GvHD), myasthenia gravis, 1-Human T-cell Lymphotropic type I and II (HTLV-I and HTLV-II)-associated diseases, Adult T-cell Leukemia (ATL), HTLV-associated Myelopathy/Tropical Spastic Paraparesis (HAM/TSP), uveitis (HU), arthropathy, pneumopathy, dermatitis, exocrinopathy, myositis, influenza, AIDS, HBV, Herpes, asthma, sinusitis, hay fever, bronchitis, chronic obstructive pulmonary disease (COPD), allergic rhinitis, acute and chronic otitis, lung fibrosis, NK leukemia/lymphoma and NK-T leukemia/lymphoma. The term treat, as used herein, includes: (i) preventing or delaying the presentation of symptoms associated with the biological condition of interest in an at-risk patient who has yet to display symptoms associated with the biological condition; (ii) ameliorating the symptoms associated with the biological condition of interest in a patient diagnosed with the biological condition; (iii) preventing, delaying, or ameliorating the presentation of symptoms associated with complications, conditions, or diseases associated with the biological condition of interest in either an at-risk patient or a patient diagnosed with the biological condition; (iv) slowing, delaying or halting the progression of the biological condition; and/or (v) preventing, delaying, slowing, halting or ameliorating the cellular events of inflammation.

The term "symptom(s)" as used herein, refers to common signs or indications that a patient is suffering from a specific condition or disease.

The term "effective amount," as used herein, refers to the amount necessary to elicit the desired biological response. In accordance with the present embodiments, an effective amount of a γc-antagonist is the amount necessary to provide an observable effect in at least one biological factor for use in treating a biological condition.

"Recombinant DNA technology" or "recombinant" refers to the use of techniques and processes for producing specific polypeptides from microbial (e.g., bacterial, yeast), invertebrate (insect), mammalian cells or organisms (e.g., transgenic animals or plants) that have been transformed or transfected with cloned or synthetic DNA sequences to enable biosynthesis of heterologous peptides. Native glycosylation pattern will only be achieved with mammalian cell expression system. Prokaryotic expression systems lack the ability to add glycosylation to the synthesized proteins. Yeast and insect cells provide a unique glycosylation pattern that may be different from the native pattern.

A "Nucleotide sequence" refers to a polynucleotide in the form of a separate fragment or as a component of a larger DNA construct that has been derived from DNA or RNA isolated at least once in substantially pure form, free of contaminating endogenous materials and in a quantity or concentration enabling identification, manipulation, and recovery of its component nucleotide sequences by standard molecular biology methods (as outlined in Current Protocols in Molecular Biology).

"Recombinant expression vector" refers to a plasmid comprising a transcriptional unit containing an assembly of (1) a genetic element or elements that have a regulatory role in gene expression including promoters and enhances, (2) a structure or coding sequence that encodes the polypeptide according to the present embodiments, and (3) appropriate transcription and translation initiation sequence and, if desired, termination sequences. Structural elements intended for use in yeast and mammalian system preferably include a signal sequence enabling extracellular secretion of translated polypeptides by yeast or mammalian host cells.

"Recombinant microbial expression system" refers to a substantially homogenous monoculture of suitable hot microorganisms, for example, bacteria such as E. coli, or yeast such as S. cerevisiae, that have stably integrated a recombinant transcriptional unit into chromosomal DNA or carry the recombinant transcriptional unit as a component of a residual plasmid. Generally, host cells constituting a recombinant microbial expression system are the progeny of a single ancestral transformed cell. Recombinant microbial expression systems will express heterologous polypeptides upon induction of the regulatory elements linked to a structural nucleotide sequence to be expressed.

The following Examples are presented for the purposes of illustration and should not be construed as limitations.

EXAMPLES

Example 1—Method for Assessing the Inhibitory Activity of γc-Antagonist Peptide

The capacity of any custom derivative peptide prepared according to the present embodiments for inhibiting the action of one γc-cytokine family member is determined using mammalian cellular assays to measure their proliferative response to the γc-cytokine family member.

For each of the six γc-cytokines, indicator cell lines: CTLL-2, a murine CD8 T cells line available from American Type Culture Collection, and PT-18, a murine mast cell line and its subclone PT-18β, is transfected with human IL-2β gene to make the cells responsive to IL-2 and IL-15 (Tagaya et al., 1996, EMBO J. 15:4928-39), and is used to quantitatively determine the γc-cytokine's growth-promoting activity (See Current protocols in Immunology from Wiley and Sons for a methodological reference). The indicator cells demonstrate semi-linear dose-dependent response when measured by a colorimetric WST-1 assay over a range of concentrations (See Clontech PT3946-1 and associated user manual, incorporated herein by reference, for a detailed description of the reagents and methods). Once the appropriate doses of the cytokine that yield the 50% and 95% maximum response from the indicator cell line is determined, various concentrations (ranging from 1 pM to 10 µM) of the purified or synthesized custom derivative peptide is added to each well containing the cytokine and indicator cells. The reduction in light absorbance at 450 nm is used as an indicator of inhibition of cytokine-stimulated cellular proliferation. Typically, the cells are stimulated by the cytokines such that the absorbance of the well containing indicator cell line and the cytokine is between 2.0 and 3.0, which is reduced to a range of 0.1 to 0.5 by the addition of inhibitory peptides.

Example 2—BNZ-γ Peptide Specifically Inhibits the Growth-Promoting Activities of IL-9 and IL-15

Figure 3A:
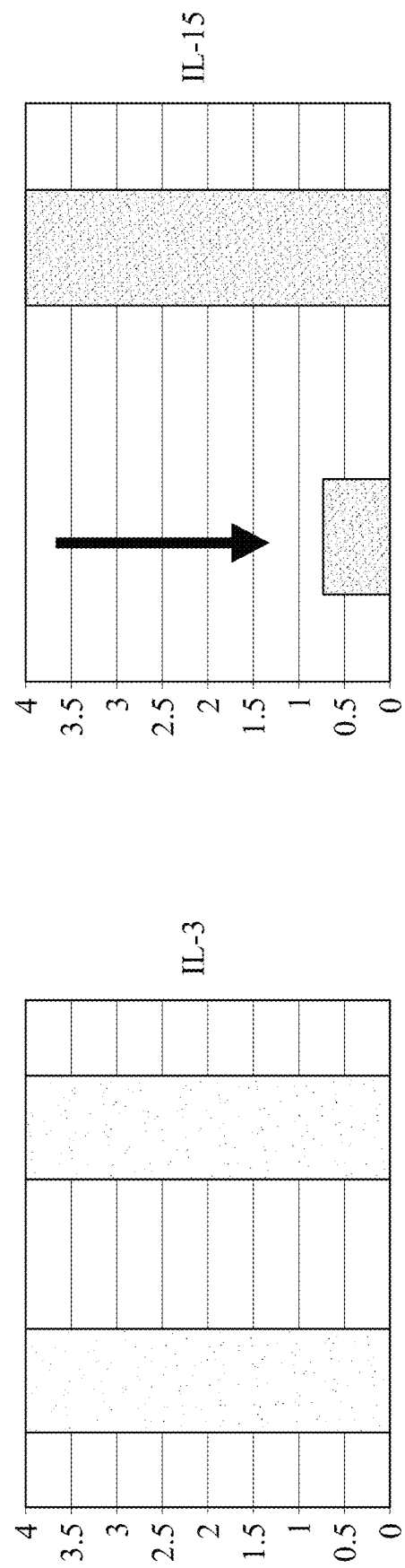
FIG. 3A shows inhibition of IL-15, and IL-9 activity by BNZ-γ in a PT-18 proliferation assay.
Figure 3A:
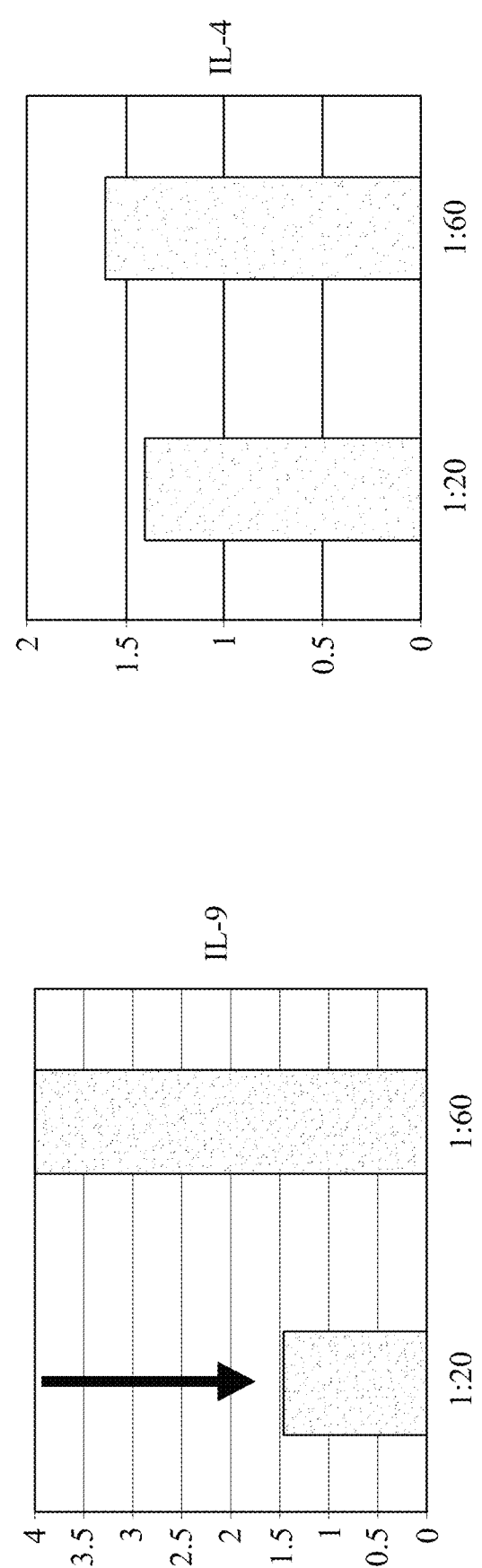

Using PT-18β cells as described above, the ability of the BNZ-γ peptide to specifically inhibit the growth-promoting activity of select γc-cytokines was determined (FIG. 3A). IL-3, a non-γc-cytokine that supports the growth of PT-1813 cells, was used as a negative control. Briefly, PT-18β cells were incubated either with two different dilutions of BNZ-γ peptide produced by HEK293T cells (1:20 or 1:50 dilution of the original supernatant of HEK293T cells transfected with a BNZ-γ expression construct) or without BNZ-γ peptide in the presence of IL-3, IL-9, IL-15, or IL-4 (1 nM of each cytokine in the culture). The growth-responses of the cells were determined 2 days after the introduction of BNZ-γ peptide and the cytokine using the WST-1 assay. The growth-promoting activity of IL-3 (a non γc-cytokine) was not inhibited by BNZ-γ. In contrast, the activity of IL-15 and IL-9 were significantly ($p<0.01$ Student's T test) reduced by the BNZ-γ peptide. Cellular proliferation stimulated by IL-4, another γc-cytokine, was not affected by the by the addition of BNZ-γ peptide. Results for IL-3, IL-9, IL-15, and IL-4 are shown at FIG. 3A.

Figure 3B:
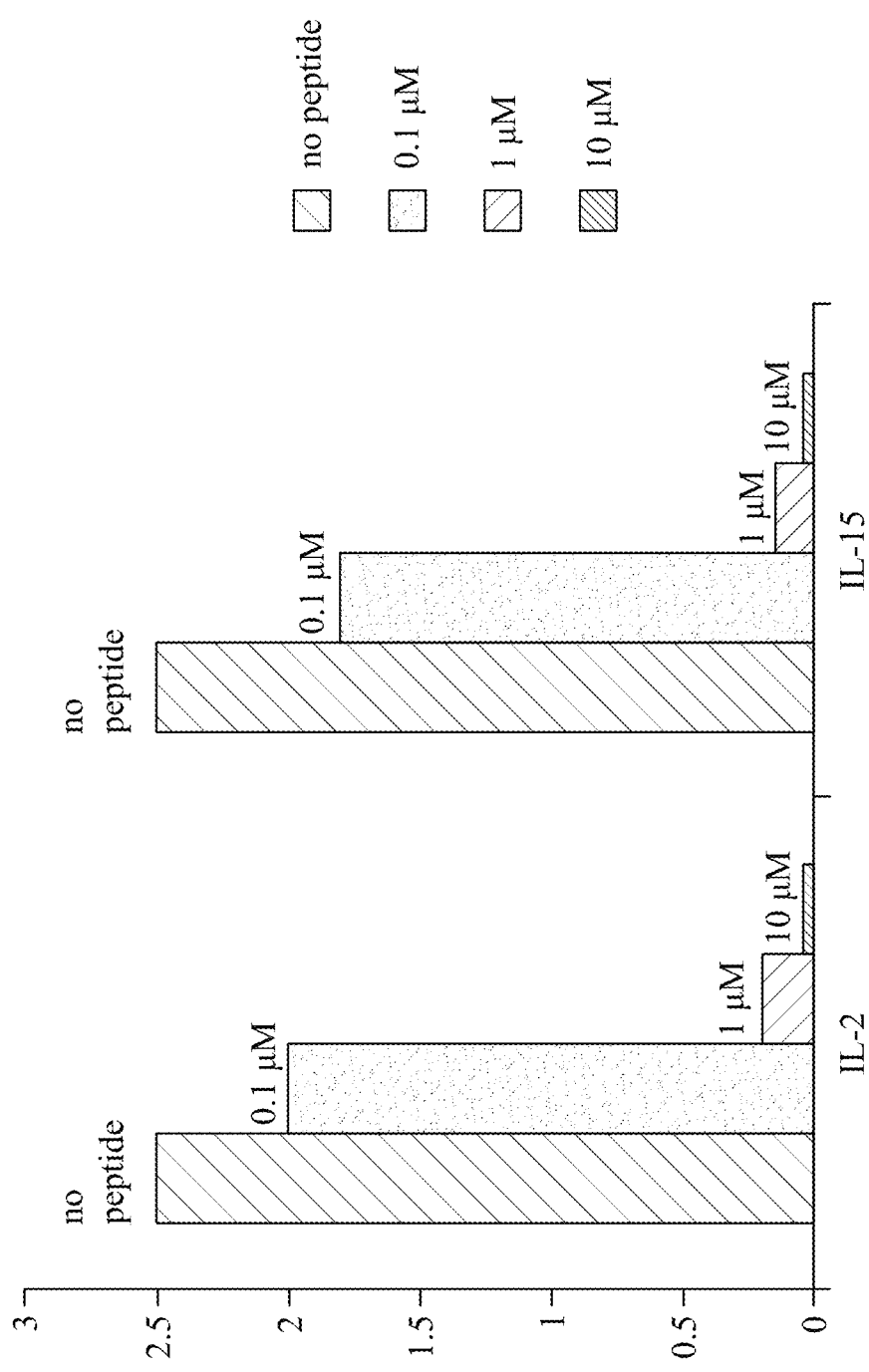
FIG. 3B shows a proliferation assay of CTTL2 cells grown in the presence of IL-2 or IL-15 and 0, 0.1, 1 or 10 μM BNZ-γ.

In a similar assay, the murine cell line CTTL2 was used. In this assay the cells were cultured with 0.5 nM of recombinant IL-2 in RPMI 10% fetal Calf Serum. To set up the proliferation assay, cells were washed from the cytokines 3 times. Cells were seeded at 1×10(5) cells per well of a 96-well plate with final concentration of 50 pM of IL-2 or IL-15. Various concentration of BNZ-γ peptide (0.1, 1, and 10 µg/ml) was added to each well. Cells were cultured for 20 hours and in the last 4 hours, $^3$H-thymidine was added to the plates. Cells were harvested using a plate reader. The data is shown in FIG. 3B.

Example 3—Method for Measuring Inhibition γc-Cytokine Activity by Assaying 3H-Thymidine Incorporation of as a Marker of Cellular Proliferation Inhibition of γc-cytokine-induced proliferation of an indicator cell population by antagonist custom derivative peptides is measured by the 3H-thymidine incorporation assay. Briefly, radiolabeled thymidine (1 microCi) is given to 20-50,000 cells undergoing proliferation in the presence of cytokines. The cell-incorporated radioactivity is measured by trapping cell-bound radioactivity to a glass-fiber filter using a conventional harvester machines (Example, Filtermate Universal Harvester from Perkin-Elmer), after which the radioactivity is measured using a b-counter (Example 1450, Trilux microplate scintillation counter).

Example 4—Method for Measuring Inhibition γc-Cytokine Activity by Assaying Incorporation of a Cell-Tracker Dye as a Marker of Cellular Proliferation Indicator cells are incubated in the presence of a selected γc-cytokine or in the presence of a selected γc-cytokine and a selected custom derivative peptide. The cell population is then labeled in vitro using a cell-tracker dye, for example, CMFDA, C2925 from Invitrogen, and the decay of cellular green fluorescence at each cellular division is monitored using a flow-cytometer (for example, Beckton-Dickinson FACScalibur). Typically, in response to γc-cytokine stimulation 7-10 different peaks corresponding to the number of divisions that the cells have undergone will appear on the green fluorescence channel. Incubation of the cells with the selected γc-cytokine and antagonist custom derivative peptide reduces the number of peaks to only 1 to 3, depending on the degree of the inhibition.

Figure 3C:
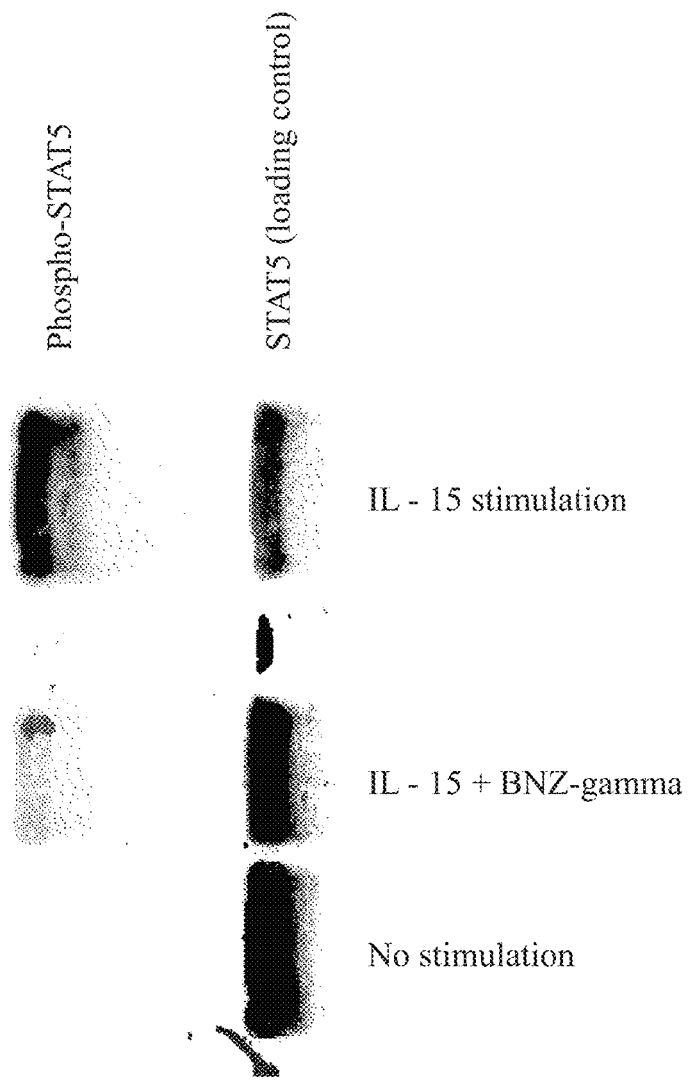
FIG. 3C shows inhibition of IL-15-mediated tyrosine-phosphorylation of STAT5 by BNZ-γ.

Example 5—Inhibition of Intracellular Signaling by BNZ-γ and its Derivative Antagonists In addition to stimulating cellular proliferation, binding of the γc-cytokines to their receptors causes a diverse array of intracellular events. (Rochman et al. 2009 Nat. Rev. Immunol. 9:480-90, Pesu et al. 2005 Immunol. Rev. 203:127-142.) Immediately after the cytokine binds to its receptor, a tyrosine kinase called Jak3 (Janus-kinase 3) is recruited to the receptor at the plasma membrane. This kinase phosphorylates the tyrosine residues of multiple proteins including the γc-subunit, STAT5 (Signal Transducer and Activator of Transcription 5) and subunits of the PI3 (Phosphatidylinositol 3) kinase. Among these, the phosphorylation of STAT5 has been implicated in many studies as being linked to the proliferation of cells initiated by the γc-cytokine. (Reviewed in Hennighausen and Robinson, 2008 Genes Dev. 22:711-21.) In accordance with these published data, whether or not the BNZ-γ peptide inhibits the tyrosine phosphorylation of STAT5 molecule in PT-18β cells stimulated by IL-15 was examined (results shown in FIG. 3C).

PT-18β cells were stimulated by IL-15 in the presence or absence of BNZ-γ peptide. Cytoplasmic proteins were extracted from the cells according to a conventional method as described in Tagaya et al. 1996 EMBO J. 15:4928-39. The extracted cytoplasmic proteins were resolved using a standard SDS-PAGE (Sodium Dodecyl-Sulfate PolyAcrylamide Gel Electrophoresis) and the phorphorylation status was confirmed by an anti-phospho-STAT5 antibody (Cell Signaling Technology, Catalog #9354, Danvers MA) using immunoblotting (See FIG. 3C, top panel). To confirm that each lane represented a similar total protein load, the membrane was then stripped, and re-probed with an anti-STAT5 antibody (Cell Signaling Technology, Catalog #9358) (See FIG. 3C, bottom panel).

These results demonstrated that tyrosine phosphorylation of STAT5, a marker of signal transduction, was induced by IL-15 in PT-18β cells, and tyrosine phosphorylation of STAT5 was markedly reduced by the BNZ-γ peptide.

Example 6—Rational Design for BNZ-γ Derivative Antagonistic Peptides

Derivative peptides are prepared based from the core sequence D/E-F-L-E/Q/N-S/R-X-I/K-X-L/I-X-Q (SEQ ID NO: 2) (where X denotes any amino acid) by substituting the defined amino acids of the core sequence with amino acids having identical physico-chemical properties as designated in FIG. 2.

Example 7—Method of Identifying the Inhibitory Specificity of Antagonistic Custom Derivative Peptides The γc-cytokine inhibitory specificity of antagonistic custom derivative peptides is determined by assaying the ability of a custom derivative peptide to inhibit the proliferative response of a cytokine-responsive cell line to each of the 6 γc-cytokines. For example, a mouse cell line, CTLL-2, is used to determine if a candidate peptide inhibits the function of IL-2 and IL-15. PT-18(β) cells are used to determine if a candidate peptide inhibits the function of IL-4 and IL-9. PT-18 (7α) cells are used to determine if a candidate peptide inhibits the function of IL-7, and PT-18(21α) cells are used to determine if a candidate peptide inhibits the function of IL-21. PT-18(β) denotes a subclone of PT-18 cells that exogenously express human IL-2Rβ by gene transfection (See Tagaya et al. 1996), PT-18(7α) denotes a subclone that expresses human IL-7Rα by gene transfection and PT-18 (21Rα) cells express human IL-21Rα.

Another alternative is to use other cell lines that respond to an array of cytokines. An example of this cell line in a human NK cell line NK92 that is commercially available by ATCC (catalog #CRL-2407). This cell line is an IL-2 dependent cell line that responds to other cytokines including IL-9, IL-7, IL-15, IL-12, IL-18, IL-21 (Gong et al. 1994 Leukemia 8: 652-658, Kingemann et al., 1996, Biol Blood Marrow Transplant 2:68; 75, Hodge D L et al., 2002 J. Immunol. 168:9090-8)

Example 8—Preparation of γc-Antagonist Peptides

Custom derivative γc-antagonist peptides are synthesized chemically by manual and automated processes.

Manual synthesis: Classical liquid-phase synthesis is employed, which involves coupling the carboxyl group or C-terminus of one amino acid to the amino group or N-terminus of another. Alternatively, solid-phase peptide synthesis (SPPS) is utilized.

Automated synthesis: Many commercial companies provide automated peptide synthesis for a cost. These companies use various commercial peptide synthesizers, including synthesizers provided by Applied Biosystems (ABI). Custom derivative γc-antagonist peptides are synthesized by automated peptide synthesizers.

Example 9—Biological Production of Custom Derivative γc-Antagonist Peptides Using Recombinant Technology A custom derivative γc-antagonist peptides is synthesized biologically as a pro-peptide that consists of an appropriate tagging peptide, a signal peptide, or a peptide derived from a known human protein that enhances or stabilizes the structure of the BNZ-γ peptide and improves its biological activity. If desired, an appropriate enzyme-cleavage sequence proceeding to the N-terminus of the peptide shall be designed to remove the tag or any part of the peptide from the final protein.

A nucleotide sequence encoding the custom derivative peptide with a stop codon at the 3' end is inserted into a commercial vector with a tag portion derived from thioredoxin of *E. coli* and a special peptide sequence that is recognized and digested by an appropriate proteolytic enzyme (for example, enterokinase) intervening between the tag portion and the nucleotide sequence encoding the custom derivative peptide and stop codon. One example of a suitable vector is the pThioHis plasmid available from Invitrogen, CA Other expression vectors may be used.

Example 10—Conjugation of the BNZ-γ and Derivative to Carrier Proteins for Immunization Purposes and Generation of Anti-BNZ-γ Antibody BNZ-γ and other custom derivative peptides are used to immunize animals to obtain polyclonal and monoclonal antibodies. Peptides are conjugated to the N- or the C-terminus of appropriate carrier proteins (for example, bovine serum albumin, Keyhold Limpet Hemocyanin (KLH), etc.) by conventional methods using Glutaraldehyde or m-Maleimidobenzoyl-N-Hydroxysuccinimide Ester. The conjugated peptides in conjunction with an appropriate adjuvant are then used to immunize animals such as rabbits, rodents, or donkeys. The resultant antibodies are examined for specificity using conventional methods. If the resultant antibodies react with the immunogenic peptide, they are then tested for the ability to inhibit individual γc-cytokine activity according to the cellular proliferation assays described in Examples 1-3. Due to the composite nature of the derivative peptides it is possible to generate a single antibody that recognizes two different cytokines simultaneously, because of the composite nature of these peptides.

Example 11—Method for Large Scale Production of Custom Derivative γc-Antagonist Peptides Recombinant proteins are produced in large scale by the use of cell-free system as described elsewhere. (See Takai et al., 2010 Curr. Pharm. Biotechnol. 11(3):272-8.) Briefly, cDNAs encoding the γc-antagonist peptide and a tag are subcloned into an appropriate vector (See Takai et al., 2010 Curr. Pharm. Biotechnol. 11(3):272-8), which is subjected to in vitro transcription, followed immediately by an in vitro translation to produce the tagged peptide. The pro-polypeptide is then purified using an immobilized antibody recognizing the tagged epitope, treated by the proteolytic enzyme and the eluate (which mostly contains the custom derivative peptide of interest) is tested for purity using conventional 18% Tricine-SDS-PAGE (Invitrogen) and conventional comassie staining. Should the desired purity of the peptide not be met (>98%), the mixture is subjected to conventional HPLC (high-performance liquid chromatography) for further purification.

Example 12—Use of Custom Derivative γc-Antagonist Peptides to Block Cytokine Function in HAM/TSP HTLV-1-associated myelopathy (HAM)/tropical spastic paraparesis (TSP) is a chronic progressive myelopathy seen in some people infected with Human T-Lymphotropic Virus Type I (HTLV-I). Infiltration of lymphocytes in the spinal cord is associated with the immune response to HTLV-I and results in the release of certain cytokines. Some of these cytokines may also damage nerves.

Patients with HAM/TSP show an elevated state of the immune system that is similar to that observed in autoimmune diseases (Oh et al. 2008 Neurol Clin. 26:781-785). This elevated state is demonstrated by the ability of HAM/TSP patient's T-cells to undergo spontaneous proliferation in an ex vivo culture for about a week in the absence of exogenously added cytokines. The spontaneous proliferation of T-cells in HAM/TSP patients is attributed, at least partly, to autocrine/paracrine loops of IL-2, IL-9, and IL-15. It has been shown that adding blocking antibody against the IL-2 or IL-15 receptors can inhibit spontaneous T-cell proliferation in a HAM/TSP ex vivo culture system. These observations, along with other data derived from ex vivo studies, have provided the rationale for taking two monoclonal antibodies (an anti-IL-2 receptor alpha or anti-Tac and an anti-IL-15 receptor beta chain) into the clinic for treatment of HAM/TSP (Azimi et al. 2001 Proc. Natl. Acad. Sci. 98:14559-64., Azimi et al., 1999 J. Immunol 163:4064-72). Anti-cytokine receptor antagonists according to the embodiments described herein, would not only be valuable as a therapeutic immuno-modulatory agent for treatment of HAM/TSP, but modulation of immune response in HAM/TSP by anti-cytokine receptor antagonists according to the present embodiments acts proof-of-concept for the use of the anti-cytokine receptor antagonists according to the present embodiments in the treatment of other auto-immune diseases.

To demonstrate the efficacy of custom derivative γc-antagonist peptides according to the embodiments described herein, we tested the ability of BNZ-γ peptide to block immune response to HTLV-I in a spontaneous T-cell proliferation assay using a HAM/TSP ex vivo culture system. Proliferation assays were performed on HAM/TSP patient blood samples with and without the addition of BNZ-γ. These assays evaluated the ability of BNZ-γ to block the function of cytokines, such as IL-2 and IL-15, present in the ex vivo HAM/TSP patient blood culture and prevent spontaneous T-cell proliferation in these samples.

Figure 4A:
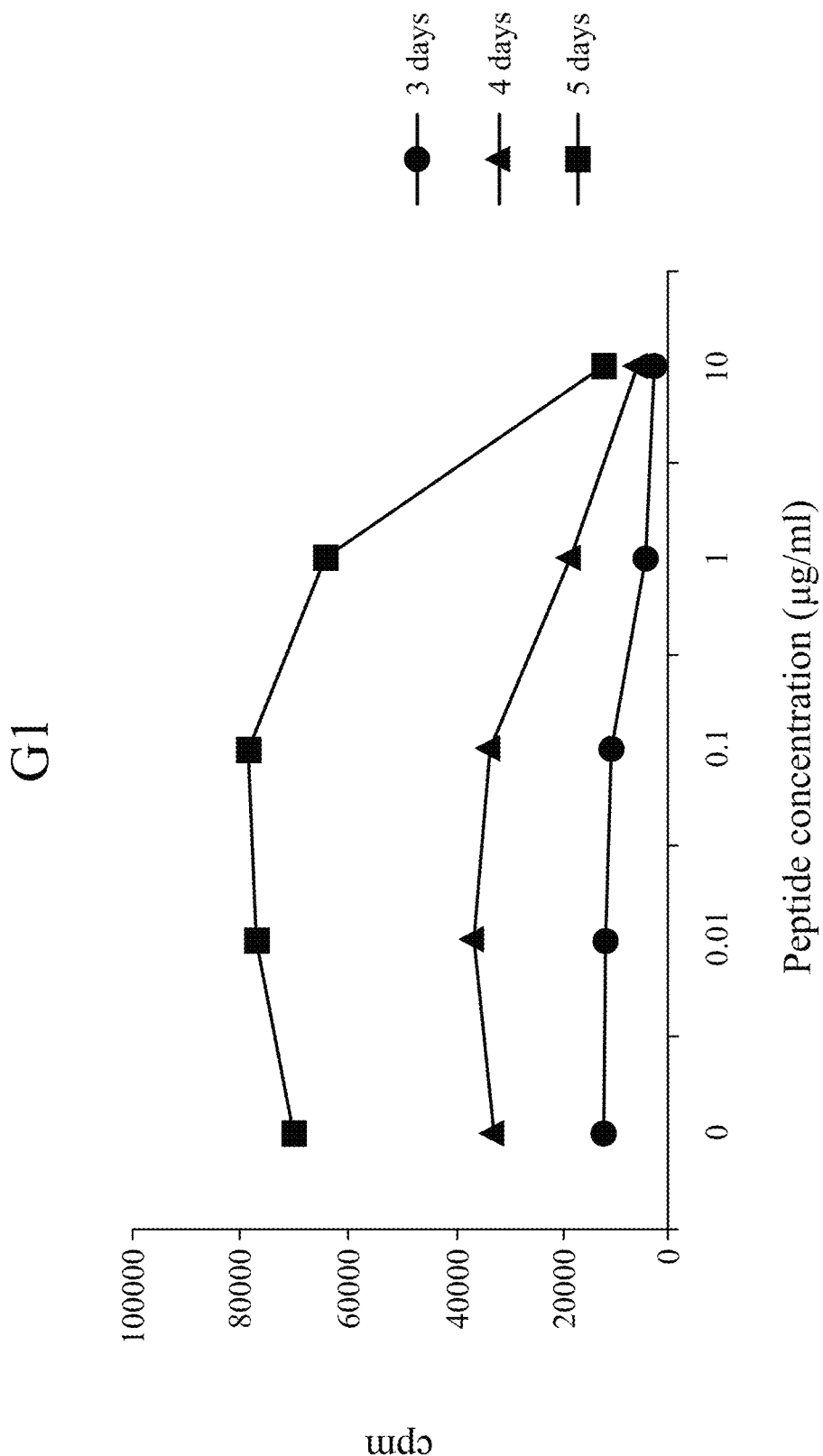
FIG. 4A shows an ex vivo T-cell proliferation assay using HAM/TSP peripheral blood. T-cell proliferation is inhibited by addition of BNZ-γ.
Figure 4B:
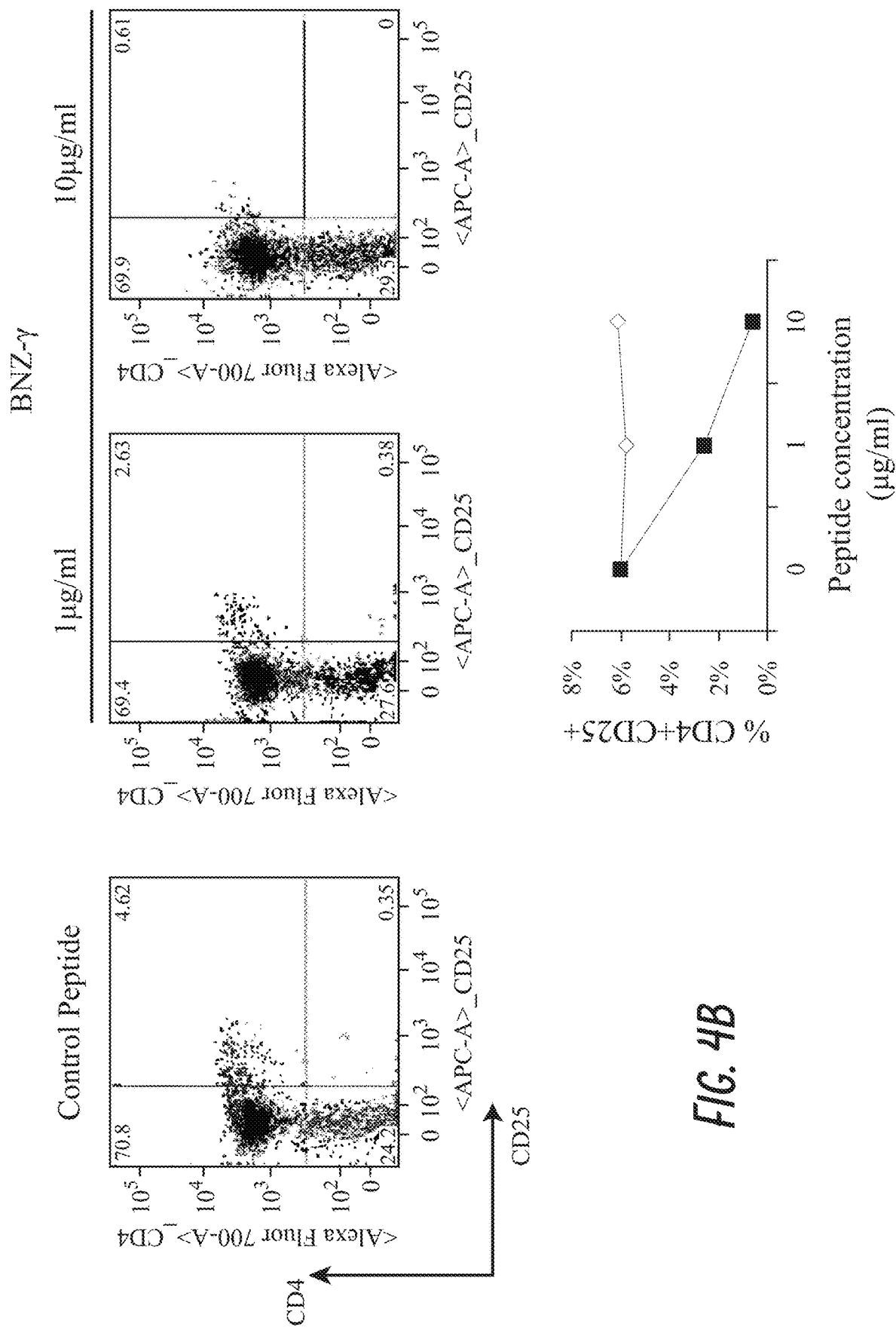
FIG. 4B shows the population of CD4+CD25+ cells in an ex vivo T-cell proliferation assay using HAM/TSP peripheral blood is diminished after adding BNZ-γ to the culture.
Figure 4C:
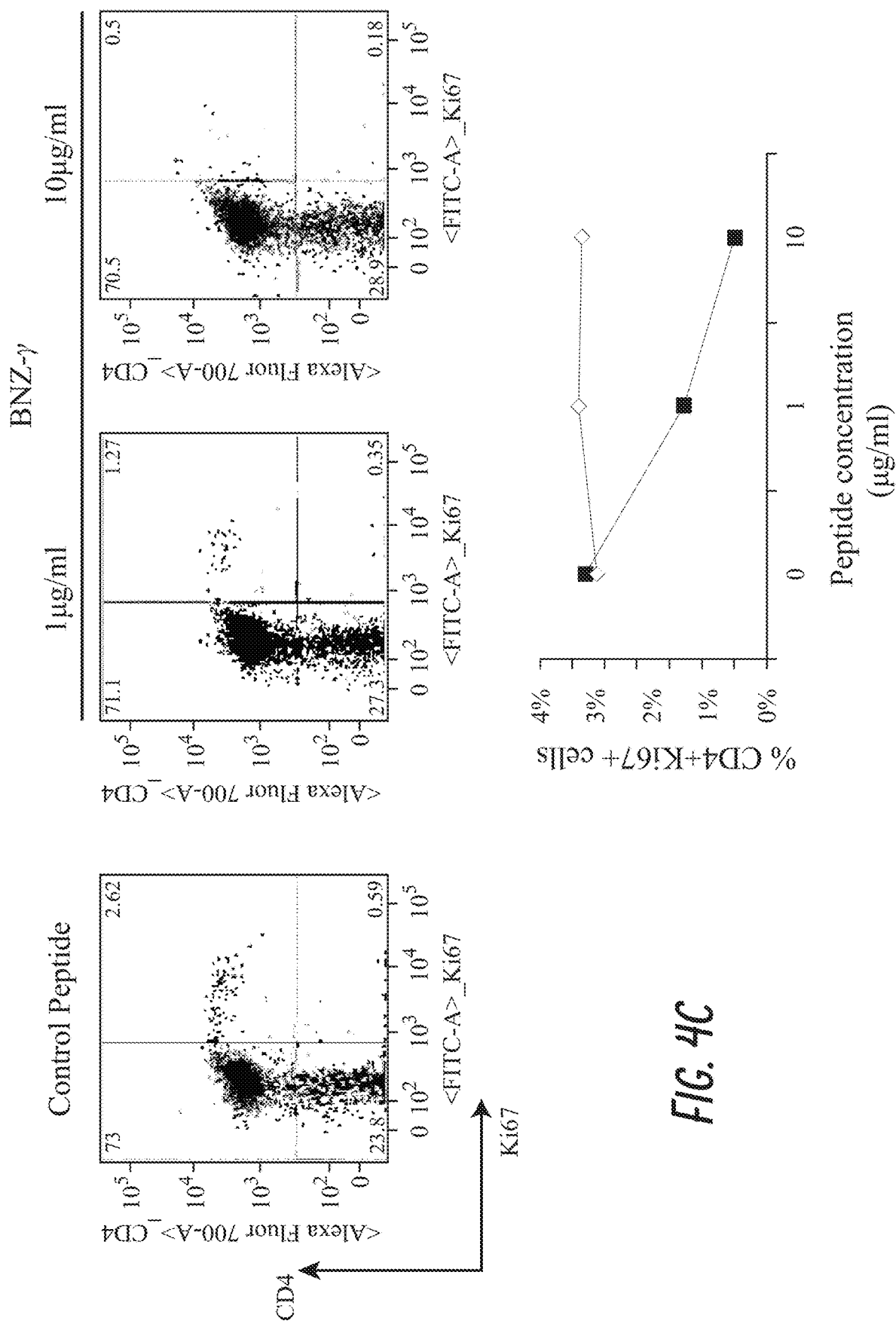
FIG. 4C shows the population of CD4+Ki67 cells in an ex vivo T-cell proliferation assay using HAM/TSP peripheral blood is reduced after adding BNZ-γ to the culture.
Figure 4D:
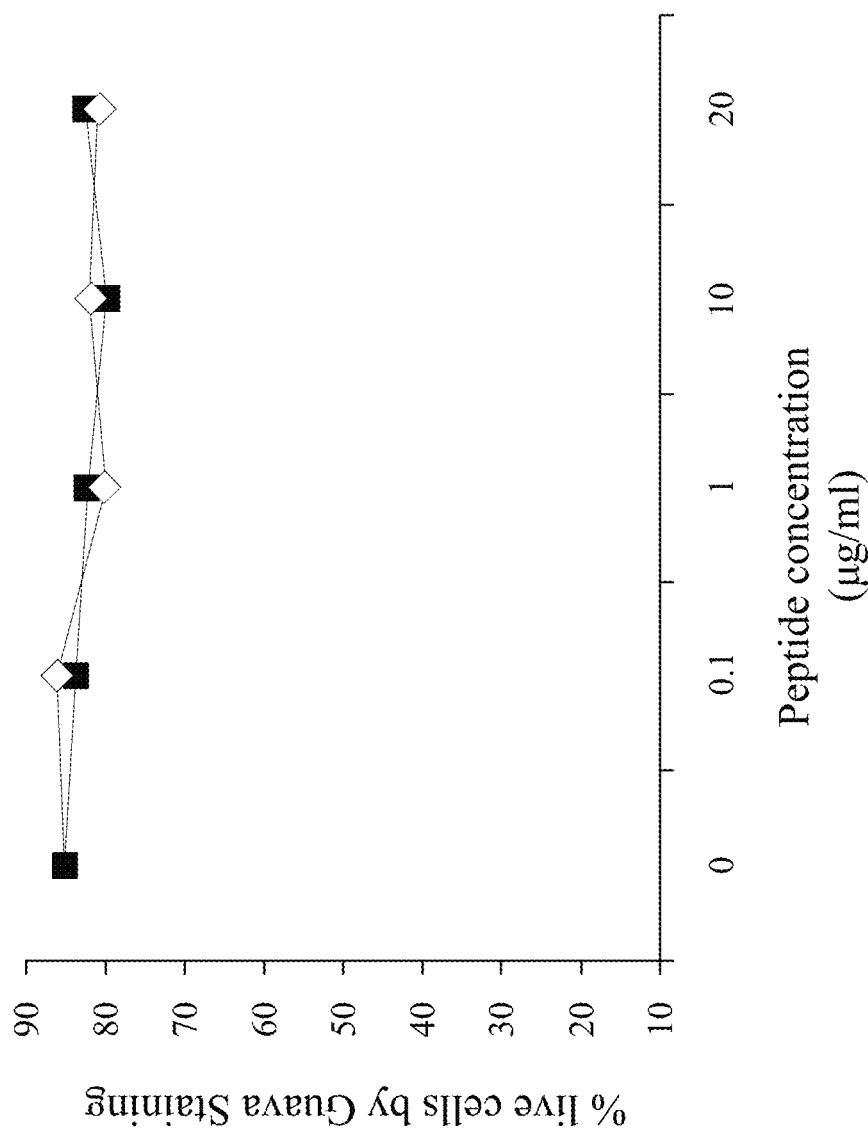
FIG. 4D shows the percent of live cells by Guava staining in an ex vivo T-cell proliferation assay using HAM/TSP peripheral blood is not impacted after adding BNZ-γ to the culture.

In an ex vivo spontaneous T-cell proliferation assay, PBMC from HAM/TSP patient was cultured at 1×10(6) cells per well of a 96 well plate in RPMI-10% FCS. Increasing concentrations of BNZ-γ peptide were added to each well. As a control, an irrelevant peptide was used in similar fashion. The cells were incubated in a 37° C. CO2 incubator for 3, 4, and 6 days. The amount of 1 μCi of $^3$H-thymidine was added to the cells. After an additional 6 hour incubation, cells were harvested their proliferation rate was measured. The data for a representative HAM/TSP patient is shown in FIG. 4A-4D. As indicated in FIG. 4A, BNZ-γ peptide inhibits the spontaneous proliferation of T-cells in HAM/TSP culture at a concentration of about 1 μg/ml.

Other immunological markers were additionally measured in this assay. The percentage of the viral specific CD8 cells was measured during the ex vivo culture using viral protein tetramers. The population of CD4+CD25+ cells, a marker of T-cell activation, as well as Ki67 staining, a marker of T-cell proliferation, was monitored in a flow cytometry assay.

Other forms of the conjugated BNZ-γ peptide derivative can be used in a similar future assay. They include albumin, BSA, PEG that can be conjugated to the peptide after chemical synthesis. Other biological forms of the BNZ-γ peptide conjugate may include regions of known protein entities (including but not limited to Fc region of human IgG) that are fused to the BNZ-γ peptide derivative.

Example 13—Method of Treating Adult T-Cell Leukemia (ATL) in a Human Patient by Administration of Custom Derivative γc-Antagonist Peptide A human patient suffering from Adult T-cell Leukemia is identified. An effective dose, as determined by the physician, of custom derivative γc-antagonist peptide, for example, BNZ-γ is administered to the patient for a period of time determined by the physician. Treatment is determined to be effective if patient enters remission.

Example 14—Method of Treating HAM/TSP in a Human Patient by Administration of Custom Derivative γc-Antagonist Peptide A human patient suffering from HAM/TSP is identified. An effective dose, as determined by the physician, of custom derivative γc-antagonist peptide, for example, BNZ-γ is administered to the patient for a period of time determined by the physician. Treatment is determined to be effective if patient's symptoms improve or if the progression of the disease has been stopped or slowed down.

REFERENCES

All references cited in this disclosure are incorporated herein by reference in their entireties.

Antony, P. A., Paulos, C. M., Ahmadzadeh, M., Akpinarli, A., Palmer, D. C., Sato, N., Kaiser A., Heinrichs, C. S., Klebanoff, C. A., Tagaya, Y., and Restifo, N P., Interleukin-2-dependent mechanisms of tolerance and immunity in vivo. 2006 J. Immunol. 176:5255-66.

Azimi, N., Nagai, M., Jacobson, S., Waldmann, T. A., IL-15 plays a major role in the persistence of Tax-specific CD8 cells in HAM/TSP patients. 2001 Proc. Natl. Acad. Sci. 98:14559-64.

Azimi, N., Mariner J., Jacobson S., Waldmann T. A., How does interleukin 15 contribute to the pathogenesis of HTLV type-1 associated myelopathy/tropical spastic paraparesis? 2000 AIDS Res. Hum. Retroviruses 16:1717-22.

Azimi, N., Jacobson, S., Leist, T., Waldmann, T. A., Involvement of IL-15 in the pathogenesis of human T lymphotropic virus type-I-associated myelopathy/tropical spastic paraparesis: implications for therapy with a monoclonal antibody directed to the IL-2/15R beta receptor. 1999 J. Immunol. 163:4064-72.

Azimi, N., Brown, K., Bamford, R. N., Tagaya, Y., Siebenlist, U., Waldmann, T. A., Human T cell lymphotropic virus type I Tax protein trans-activates interleukin 15 gene transcription through an N F-kappaB site. 1998 Proc. Natl. Acad. Sci. USA 95:2452-7.

Bazan, J. F., Hematopoietic receptors and helical cytokines. 1990 Immunol. Today 11:350-354.

Bettini, M., and Vignali, D. A., Regulatory T cells and inhibitory cytokines in autoimmunity. 2009 Curr. Opin. Immunol. 21:612-8.

Bodd, M., Raki, M., Tollefsen, S., Fallang, L. E., Bergseng, E., Lundin, K. E., Sollid, L. M., HLA-DQ2-restricted gluten-reactive T cells produce IL-21 but not IL-17 or IL-22. 2010 Mucosal Immunol. 3:594-601.

De Rezende, L. C., Silva I. V., Rangel, L. B., Guimaraes, M. C., Regulatory T cells as a target for cancer therapy. 2010 Arch. Immunol. Ther. Exp. 58:179-90.

Dubois, S., Mariner, J., Waldmann, T. A., Tagaya, Y., IL-15Ralpha recycles and presents IL-15 In trans to neighboring cells. 2002 Immunity 17:537-47.

Dodge D L. Et al., IL-2 and IL-12 alter N K cell responsiveness to IFN-gamma-inducible protein 10 by down-regulating CXCR3 expression. J. Immun. 168:6090-8.

Fehniger, T. A., Suzuki, K., Ponnappan, A., VanDeusen, J. B., Cooper, M. A., Florea, S. M., Freud, A. G., Robinson, M. L., Durbin, J., Caligiuri, M. A., Fatal leukemia in interleukin 15 transgenic mice follows early expansions in natural killer and memory phenotype CD8+ T cells. 2001 J. Exp. Med. 193:219-31.

Fisher, A. G., Burdet, C., LeMeur, M., Haasner, D., Gerber, P., Cerediq, R., Lymphoproliferative disorders in an IL-7 transgenic mouse line. 1993 Leukemia 2:S66-68.

Gong J H, et al. Characterization of a human cell line (NK-92) with phenotypical and functional characteristics of activated natural killer cells. Leukemia 8: 652-658, 1994.

Hennighausen, L., Robinson, G. W., Interpretation of cytokine signaling through the transcription factors STAT5A and STAT5B. 2008 Genes Dev. 22:711-21.

Kiingemann H G, et al. A cytotoxic N K-cell line (NK-92) for ex vivo purging of leukemia from blood. Biol. Blood Marrow Transplant. 2: 68-75, 1996.

Krause, C. D. and Pestka, S., Evolution of the Class 2 cytokines and receptors, and discovery of new friends and relatives. 2005 Pharmacol. and Therapeutics 106:299-346.

Kundig, T. M., Schorle, H., Bachmann, M. F., Hengartener, H., Zinkernagel, R. M., Horak, I., Immune Responses of the interleukin-2-deficient mice. 1993 Science 262:1059-61.

Le Buanec, H., Paturance, S., Couillin, I., Schnyder-Candrian, S., Larcier, P., Ryffel, B., Bizzini, B., Bensussan, A., Burny, A., Gallo, R., Zagury, D., Peltre, G., Control of allergic reactions in mice by an active anti-murine IL-4 immunization. 2007 Vaccine 25:7206-16.

Littman, D. R., Rudensky, A Y., Th17 and regulatory T cells in mediating and restraining inflammation. 2010 Cell 140(6):845-58.

Miyagawa, F., Tagaya, Y., Kim, B. S., Patel, H. J., Ishida, K., Ohteki, T., Waldmann, T. A., Katz, S. I., IL-15 serves as a costimulator in determining the activity of autoreactive CD8 T cells in an experimental mouse model of graft-versus-host-like disease. 2008 J. Immunol. 181:1109-19.

Noguchi, M., Yi, H., Rosenblatt, H. M., Filipovich, A. H., Adelstein, S., Modi, W. S., McBride, O. W., Leonard, W. J., Interleukin 2 receptor gamma chain mutation results in X-linked severe combined immunodeficiency in humans. 1993 Cell 73:147-157.

O H, U., Jacobson S., Treatment of HTLV-I-Associated Myelopathy/Tropical Spastic Paraparesis: Towards Rational Targeted Therapy 2008 Neurol Clin. 2008 26: 781-785.

Orzaez, M., Gortat, A., Mondragon, L., Perez-Paya, E., Peptides and Peptide Mimics as Modulators of Apototic Pathways. 2009 Chem. Med. Chem. 4:146-160.

O'Shea, J. J., Targeting the Jak/STAT pathway for immunosuppression. 2004 Ann. Rheum. Dis. 63:(suppl II):ii67-71.

Paul, W. E., Pleiotropy and redundancy: T cell-derived lymphokines in the immune response. 1989 Cell 57:521-4.

Pesu M, Candotti F, Husa M, Hofmann S R, Notarangelo L D, and O'Shea J J. Jak3, severe combined immunodeficiency, and a new class of immunosuppressive drugs. 2005 Immunol. Rev. 203:127-142.

Pesu, M., Laurence, A., Kishore, N., Zwillich, S., Chan, G., O'Shea, J. J., Therapeutic targeting of Janus kinases. Immunol. 2008 Rev. 223:132-142.

Rochman, Y., Spolski, R., Leonard, W. J., New Insights into the regulation of T cells by gamma c family cytokines. 2009 Nat. Rev. Immunol. 9:480-90.

Sakaguchi, S., Yamaguchi, T., Nomura, T., Ono, M., Regulatory T cells and immune tolerance. 2008 Cell 133: 775-87.

Sato, N., Sabzevari, H., Fu, S., Ju, W., Bamford, R. N., Waldmann, T. A., and Tagaya, Y., Development of an IL-15-Autocrine CD8 T-cell Leukemia in IL-15 Transgenic mice requires the cis-expression of IL-15R apha. Blood 2011 in press.

Sugamura, K., Asao, H., Kondo, M., Tanaka, N., Ishii, N., Nakamura, M., Takeshita, T., The common gamma-chain for multiple cytokine receptors. 1995 Adv. Immunol. 59: 225-277.

Sugamura, K., Asao, H., Kondo, M., Tanaka, N., Ishii, N., Ohbo, K., Nakamura, M., Takeshita, T., The interleukin-2 receptor gamma chain: its role in the multiple cytokine receptor complexes and T cell development in XSCID. 1996 Annu. Rev. Immunol. 14:179-205.

Tagaya, Y., Burton, J. D., Miyamoto, Y., Waldmann, T A., Identification of a novel receptor/signal transduction pathway for IL-15/T in mast cells. 1996 EMBO J. 15:4928-39.

Tagaya, Y., Memory CD8 T cells now join "Club 21". 2010 J. Leuk. Biol. 87:13-15.

Takai, K., Sawasaki, T., and Endo. Y. The Wheat-Germ Cell-Free Expression System, 2010 Curr. Pharm. Biotechnol. 11:272-8.

Tanaka, T., et al., A novel monoclonal antibody against murine IL-2 receptor beta-chain. Characterization of receptor expression in normal lymphoid cells and EL-4 cells. 1991 J. Immunol. 147:2222-28.

Takeshita, T., Asao, H., Ohtani, K., Ishii, N., Kumaki, S., Tanaka, N., Manukata, H., Nakamura, M., Sugamura, K., Cloning of the Gamma chain of the Human IL2 receptor. 1992 Science 257:379-382.

Waldmann, T. A., Anti-Tac (daclizumab, Zenapax) in the treatment of leukemia, autoimmune diseases, and in the prevention of allograft rejection: a 25-year personal odyssey. 2007 J. Clin. Immunol. 27: 1-18.

What is claimed is:
1. A nucleotide sequence encoding a composite peptide that comprises amino acid sequences of at least two interleukin (IL) protein gamma-c-box D-helix regions, wherein the composite peptide comprises an amino acid sequence Xaa Phe Leu Xaa Xaa Xaa Xaa Xaa Xaa Xaa Gln (SEQ ID NO: 2), wherein the Xaa at position 1 is D or E, the Xaa at position 4 is E, Q, or N, the Xaa at position 5 is S or R, the Xaa at position 6 is any amino acid, the Xaa at position 7 is I or K, the Xaa at position 8 is any amino acid, the Xaa at position 9 is L or I, the Xaa at position 10 is any amino acid.

2. The nucleotide sequence of claim 1, wherein the composite peptide inhibits the activity of two or more γc-cytokines selected from the group consisting of IL-2, IL-4, IL-7, IL-9, IL-15, and IL-21.

3. The nucleotide sequence of claim 1, wherein the nucleotide sequence is selected from the group consisting of dsDNA, ssDNA, dsRNA, and ssRNA.

4. The nucleotide sequence of claim 1, wherein the composite peptide comprises the amino acid sequence I-K-E-F-L-Q-R-F-I-H-I-V-Q-S-I-I-N-T-S(SEQ ID NO: 1) (BNZ-γ).

5. A pharmaceutical composition comprising:
a nucleotide sequence encoding a peptide conjugate; and
a pharmaceutically acceptable carrier, diluent, excipient or combination thereof;
wherein the peptide conjugate inhibits the activity of two or more γc-cytokines selected from the group consisting of IL-2, IL-4, IL-7, IL-9, IL-15, and IL-21;
wherein the peptide conjugate thereof comprises an amino acid sequence Xaa Phe Leu Xaa Xaa Xaa Xaa Xaa Xaa Xaa Gln (SEQ ID NO: 2), wherein the Xaa at position 1 is D or E, the Xaa at position 4 is E, Q, or N, the Xaa at position 5 is S or R, the Xaa at position 6 is any amino acid, the Xaa at position 7 is I or K, the Xaa at position 8 is any amino acid, the Xaa at position 9 is L or I, the Xaa at position 10 is any amino acid.

6. The pharmaceutical composition of claim 5, wherein the nucleotide sequence further comprises a sequence encoding a signal peptide.

7. The pharmaceutical composition of claim 5, wherein the nucleotide sequence is selected from the group consisting of dsDNA, ssDNA, dsRNA, and ssRNA.

8. The pharmaceutical composition of claim 5, wherein the peptide conjugate comprises the amino acid sequence I-K-E-F-L-Q-R-F-I-H-I-V-Q-S-I-I-N-T-S(SEQ ID NO: 1) (BNZ-γ).

9. A method for blocking signaling by two or more γc-cytokine family members, comprising contacting a cell with the pharmaceutical composition of claim 5.

10. A method of inhibiting γc-cytokine binding to a γc-subunit comprising contacting a γc-subunit of a cell with the pharmaceutical composition of claim 5.

11. A method of treating a γc-cytokine-mediated disease, the method comprising administering the pharmaceutical composition of claim 5 to a subject in need thereof, wherein the γc-cytokine-mediated disease is selected from the group consisting of myasthenia gravis, inflammatory bowel disease, CD4-leukemia, CD8-leukemia, LGL-leukemia, systemic lupus erythematosis, Sjögren's syndrome, Wegener's granulomatosis, Celiac disease, Hashimoto's thyroiditis, rheumatoid arthritis, diabetes mellitus, psoriasis, multiple sclerosis, uvietis, inflammation of the eye, and graft-versus-host disease (GvHD).

12. A method of treating an HTLV-1-associated myelopathy (HAM)/tropical spastic paraparesis (TSP) associated disease, the method comprising administering the pharmaceutical composition of claim 5 to a subject in need thereof, wherein the HAM/TSP associated disease is selected from the group consisting of Adult T-cell Leukemia (ATL), HTLV-associated Myelopathy/Tropical Spastic Paraparesis (HAM/TSP), and other non-neeoplastic inflammatory diseases associated with HTLV such as uveitis (HU), arthropathy, pneumopathy, dermatitis, exocrinopathy, and myositis.

13. A method of treating an inflammatory respiratory disease, the method comprising administering the pharmaceutical composition of claim 5 to a subject in need thereof, wherein the inflammatory respiratory disease is selected from the group consisting of asthma, sinusitis, hay fever, bronchitis, chronic obstructive pulmonary disease (COPD), allergic rhinitis, acute and chronic otitis, and lung fibrosis.

14. A method of treating a cosmetic condition, the method comprising administering the pharmaceutical composition of claim 5 to a subject in need thereof, wherein the cosmetic disease is selected from the group consisting of acne, hair loss, sunburn, nail maintenance, and appearance of aging.

15. A genetic construct comprising:
a nucleotide sequence encoding a composite peptide; and
at least one regulatory element, wherein the at least one regulatory element is configured to regulate an expression of the composite peptide,
wherein the composite peptide, when expressed, can inhibit the activity of two or more γc-cytokines selected from the group consisting of IL-2, IL-4, IL-7, IL-9, IL-15, and IL-21;
wherein the composite peptide comprises an amino acid sequence Xaa Phe Leu Xaa Xaa Xaa Xaa Xaa Xaa Xaa Gln (SEQ ID NO: 2), wherein the Xaa at position 1 is D or E, the Xaa at position 4 is E, Q, or N, the Xaa at position 5 is S or R, the Xaa at position 6 is any amino acid, the Xaa at position 7 is I or K, the Xaa at position 8 is any amino acid, the Xaa at position 9 is L or I, the Xaa at position 10 is any amino acid.

16. The genetic construct of claim 15, wherein the genetic construct is a DNA.

17. The genetic construct of claim 15, wherein the genetic construct is an RNA.

18. The genetic construct of claim 15, wherein the composite peptide comprises the amino acid sequence I-K-E-F-L-Q-R-F-I-H-I-V-Q-S-I-I-N-T-S(SEQ ID NO: 1) (BNZ-γ).

* * * * *

SEQUENCE LISTING

```
<160> NUMBER OF SEQ ID NOS: 10

<210> SEQ ID NO 1
<211> LENGTH: 19
<212> TYPE: PRT
<213> ORGANISM: Artificial
<220> FEATURE:
<223> OTHER INFORMATION: Synthetic

<400> SEQUENCE: 1

Ile Lys Glu Phe Leu Gln Arg Phe Ile His Ile Val Gln Ser Ile Ile
1               5                   10                  15

Asn Thr Ser

<210> SEQ ID NO 2
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = D or E
<220> FEATURE:
<221> NAME/KEY: MISC_FEATURE
<222> LOCATION: (4)..(4)
<223> OTHER INFORMATION: X = E or Q or N
<220> FEATURE:
<221> NAME/KEY: MISC_FEATURE
<222> LOCATION: (5)..(5)
<223> OTHER INFORMATION: X = S or R
<220> FEATURE:
<221> NAME/KEY: MISC_FEATURE
<222> LOCATION: (6)..(6)
<223> OTHER INFORMATION: X = Any amino acid
<220> FEATURE:
<221> NAME/KEY: MISC_FEATURE
<222> LOCATION: (7)..(7)
<223> OTHER INFORMATION: X = I or K
<220> FEATURE:
<221> NAME/KEY: MISC_FEATURE
<222> LOCATION: (8)..(8)
<223> OTHER INFORMATION: X = Any amino acid
<220> FEATURE:
<221> NAME/KEY: MISC_FEATURE
<222> LOCATION: (9)..(9)
<223> OTHER INFORMATION: X = L or I
<220> FEATURE:
<221> NAME/KEY: MISC_FEATURE
<222> LOCATION: (10)..(10)
<223> OTHER INFORMATION: X = Any amino acid

<400> SEQUENCE: 2

Xaa Phe Leu Xaa Xaa Xaa Xaa Xaa Xaa Xaa Gln
1               5                   10

<210> SEQ ID NO 3
<211> LENGTH: 19
<212> TYPE: PRT
```

```
<213> ORGANISM: Artificial
<220> FEATURE:
<223> OTHER INFORMATION: Synthetic

<400> SEQUENCE: 3

Ile Lys Glu Phe Leu Gln Ser Phe Val His Ile Val Gln Met Phe Ile
1               5                   10                  15

Asn Thr Ser

<210> SEQ ID NO 4
<211> LENGTH: 20
<212> TYPE: PRT
<213> ORGANISM: Artificial
<220> FEATURE:
<223> OTHER INFORMATION: Synthetic

<400> SEQUENCE: 4

Ile Val Glu Phe Leu Asn Arg Trp Ile Thr Phe Cys Gln Ser Ile Ile
1               5                   10                  15

Ser Thr Leu Thr
            20

<210> SEQ ID NO 5
<211> LENGTH: 21
<212> TYPE: PRT
<213> ORGANISM: Artificial
<220> FEATURE:
<223> OTHER INFORMATION: Synthetic

<400> SEQUENCE: 5

Pro Lys Glu Phe Leu Glu Arg Phe Lys Ser Leu Leu Gln Lys Met Ile
1               5                   10                  15

His Gln His Leu Ser
            20

<210> SEQ ID NO 6
<211> LENGTH: 21
<212> TYPE: PRT
<213> ORGANISM: Artificial
<220> FEATURE:
<223> OTHER INFORMATION: Synthetic

<400> SEQUENCE: 6

Leu Glu Asn Phe Leu Glu Arg Leu Lys Thr Ile Met Arg Glu Lys Tyr
1               5                   10                  15

Ser Lys Cys Ser Ser
            20

<210> SEQ ID NO 7
<211> LENGTH: 21
<212> TYPE: PRT
<213> ORGANISM: Artificial
<220> FEATURE:
<223> OTHER INFORMATION: Synthetic

<400> SEQUENCE: 7

Ala Leu Thr Phe Leu Glu Ser Leu Leu Glu Leu Phe Gln Lys Glu Lys
1               5                   10                  15

Met Arg Gly Met Arg
            20

<210> SEQ ID NO 8
<211> LENGTH: 20
<212> TYPE: PRT
```

<213> ORGANISM: Artificial
<220> FEATURE:
<223> OTHER INFORMATION: Synthetic

<400> SEQUENCE: 8

Asp Leu Cys Phe Leu Lys Arg Leu Leu Gln Glu Ile Lys Thr Cys Trp
1               5                   10                  15

Asn Lys Ile Leu
            20

<210> SEQ ID NO 9
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = Any amino acid
<220> FEATURE:
<221> NAME/KEY: MISC_FEATURE
<222> LOCATION: (2)..(2)
<223> OTHER INFORMATION: X = Any amino acid
<220> FEATURE:
<221> NAME/KEY: MISC_FEATURE
<222> LOCATION: (3)..(3)
<223> OTHER INFORMATION: X = D or E
<220> FEATURE:
<221> NAME/KEY: MISC_FEATURE
<222> LOCATION: (6)..(6)
<223> OTHER INFORMATION: X = E or Q or N or polar amino acid
<220> FEATURE:
<221> NAME/KEY: MISC_FEATURE
<222> LOCATION: (7)..(7)
<223> OTHER INFORMATION: X = S or R or polar amino acid
<220> FEATURE:
<221> NAME/KEY: MISC_FEATURE
<222> LOCATION: (8)..(8)
<223> OTHER INFORMATION: X = Non-polar amino acid
<220> FEATURE:
<221> NAME/KEY: MISC_FEATURE
<222> LOCATION: (9)..(9)
<223> OTHER INFORMATION: X = I or K or non-polar amino acid
<220> FEATURE:
<221> NAME/KEY: MISC_FEATURE
<222> LOCATION: (10)..(10)
<223> OTHER INFORMATION: X = Any amino acid
<220> FEATURE:
<221> NAME/KEY: MISC_FEATURE
<222> LOCATION: (11)..(11)
<223> OTHER INFORMATION: X = L or I or aliphatic amino acid
<220> FEATURE:
<221> NAME/KEY: MISC_FEATURE
<222> LOCATION: (12)..(12)
<223> OTHER INFORMATION: X = Non-polar amino acid
<220> FEATURE:
<221> NAME/KEY: MISC_FEATURE
<222> LOCATION: (14)..(14)
<223> OTHER INFORMATION: X = Charged amino acid
<220> FEATURE:
<221> NAME/KEY: MISC_FEATURE
<222> LOCATION: (15)..(15)
<223> OTHER INFORMATION: X = Any amino acid
<220> FEATURE:
<221> NAME/KEY: MISC_FEATURE
<222> LOCATION: (16)..(16)
<223> OTHER INFORMATION: X = I or K
<220> FEATURE:
<221> NAME/KEY: MISC_FEATURE
<222> LOCATION: (17)..(17)
<223> OTHER INFORMATION: X = Any amino acid
<220> FEATURE:
<221> NAME/KEY: MISC_FEATURE
<222> LOCATION: (18)..(18)
<223> OTHER INFORMATION: X = Any amino acid

```
<220> FEATURE:
<221> NAME/KEY: MISC_FEATURE
<222> LOCATION: (19)..(19)
<223> OTHER INFORMATION: X = Any amino acid

<400> SEQUENCE: 9

Xaa Xaa Xaa Phe Leu Xaa Xaa Xaa Xaa Xaa Xaa Xaa Gln Xaa Xaa Xaa
1               5                   10                  15

Xaa Xaa Xaa

<210> SEQ ID NO 10
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = Any amino acid
<220> FEATURE:
<221> NAME/KEY: MISC_FEATURE
<222> LOCATION: (2)..(2)
<223> OTHER INFORMATION: X = Any amino acid
<220> FEATURE:
<221> NAME/KEY: MISC_FEATURE
<222> LOCATION: (3)..(3)
<223> OTHER INFORMATION: X = D or E
<220> FEATURE:
<221> NAME/KEY: MISC_FEATURE
<222> LOCATION: (6)..(6)
<223> OTHER INFORMATION: X = E or Q or N or polar amino acid
<220> FEATURE:
<221> NAME/KEY: MISC_FEATURE
<222> LOCATION: (7)..(7)
<223> OTHER INFORMATION: X = S or R or polar amino acid
<220> FEATURE:
<221> NAME/KEY: MISC_FEATURE
<222> LOCATION: (8)..(8)
<223> OTHER INFORMATION: X = Non-polar amino acid
<220> FEATURE:
<221> NAME/KEY: MISC_FEATURE
<222> LOCATION: (9)..(9)
<223> OTHER INFORMATION: X = I or K or non-polar amino acid
<220> FEATURE:
<221> NAME/KEY: MISC_FEATURE
<222> LOCATION: (10)..(10)
<223> OTHER INFORMATION: X = Any amino acid
<220> FEATURE:
<221> NAME/KEY: MISC_FEATURE
<222> LOCATION: (11)..(11)
<223> OTHER INFORMATION: X = L or I or aliphatic amino acid
<220> FEATURE:
<221> NAME/KEY: MISC_FEATURE
<222> LOCATION: (12)..(12)
<223> OTHER INFORMATION: X = Non-polar amino acid
<220> FEATURE:
<221> NAME/KEY: MISC_FEATURE
<222> LOCATION: (14)..(14)
<223> OTHER INFORMATION: X = Charged amino acid
<220> FEATURE:
<221> NAME/KEY: MISC_FEATURE
<222> LOCATION: (15)..(15)
<223> OTHER INFORMATION: X = Any amino acid
<220> FEATURE:
<221> NAME/KEY: MISC_FEATURE
<222> LOCATION: (17)..(17)
<223> OTHER INFORMATION: X = Any amino acid

<400> SEQUENCE: 10

Xaa Xaa Xaa Phe Leu Xaa Xaa Xaa Xaa Xaa Xaa Xaa Gln Xaa Xaa Ile
1               5                   10                  15

Xaa Thr Ser
```